US012570707B2

(12) United States Patent
Joel

(10) Patent No.: US 12,570,707 B2
(45) Date of Patent: Mar. 10, 2026

(54) CODON-OPTIMISED COMPLEMENT FACTOR I

(71) Applicant: NOVARTIS PHARMACEUTICALS UK LIMITED, London (GB)

(72) Inventor: Josephine Heather Lucienne Joel, Stevenage (GB)

(73) Assignee: NOVARTIS PHARMACEUTICALS UK LIMITED, London (GB)

( * ) Notice: Subject to any disclaimer, the term of this patent is extended or adjusted under 35 U.S.C. 154(b) by 1251 days.

(21) Appl. No.: 17/415,852

(22) PCT Filed: Dec. 20, 2019

(86) PCT No.: PCT/GB2019/053668
§ 371 (c)(1),
(2) Date: Jun. 18, 2021

(87) PCT Pub. No.: WO2020/128516
PCT Pub. Date: Jun. 25, 2020

(65) Prior Publication Data
US 2022/0073576 A1 Mar. 10, 2022

(30) Foreign Application Priority Data

Dec. 21, 2018 (GB) ..................................... 1821089

(51) Int. Cl.
C07K 14/47 (2006.01)
A61K 48/00 (2006.01)

(52) U.S. Cl.
CPC ............ C07K 14/472 (2013.01); A61K 48/00 (2013.01)

(58) Field of Classification Search
CPC ...... C07K 14/472; C07K 14/47; A61K 48/00; A61K 38/00; C12N 2750/14143; C12N 2800/22; C12N 9/64; C12N 15/86; C12N 2830/48; C12N 2830/50; A61P 27/02
See application file for complete search history.

(56) References Cited

U.S. PATENT DOCUMENTS

| | | | | |
|---|---|---|---|---|
| 7,745,389 | B2 * | 6/2010 | Hageman | ................ A61P 17/00 435/7.1 |
| 9,066,941 | B2 | 6/2015 | Lachmann | |
| 9,782,460 | B2 | 10/2017 | Lachmann | |
| 10,940,186 | B2 | 3/2021 | Lachmann | |
| 2013/0302409 | A1 | 11/2013 | Fuchs et al. | |
| 2014/0271603 | A1 | 9/2014 | Abache | |
| 2017/0190753 | A1 | 7/2017 | Abache | |
| 2019/0255193 | A1 | 8/2019 | Groendahl et al. | |
| 2020/0147240 | A1 | 5/2020 | Lachmann et al. | |
| 2021/0268076 | A1 | 9/2021 | Lachmann | |
| 2022/0072157 | A1 | 3/2022 | Dreismann et al. | |
| 2023/0212275 | A1 | 7/2023 | Joel et al. | |

| | | | |
|---|---|---|---|
| 2023/0212635 | A1 | 7/2023 | Marchbank et al. |
| 2023/0277689 | A1 | 9/2023 | Groendahl et al. |
| 2024/0238446 | A1 | 7/2024 | Lachmann et al. |

FOREIGN PATENT DOCUMENTS

| | | |
|---|---|---|
| CN | 101160412 A | 4/2008 |
| KR | 2009-0122465 A | 11/2009 |
| RU | 2473563 C2 | 1/2013 |
| WO | WO2006088950 A2 | 8/2006 |
| WO | 2007/149567 A2 | 12/2007 |
| WO | WO2008106644 A2 | 9/2008 |
| WO | 2008154251 A2 | 12/2008 |
| WO | 2013151665 A2 | 10/2013 |
| WO | 2013151666 A2 | 10/2013 |
| WO | WO 2015/092335 A2 | 6/2015 |
| WO | 2015/130826 A1 | 9/2015 |
| WO | WO 2016/170176 A1 | 10/2016 |
| WO | WO 2017/072515 A1 | 5/2017 |
| WO | 2017/191274 A2 | 11/2017 |
| WO | WO 2017/194912 A1 | 11/2017 |
| WO | WO 2018/170152 A1 | 9/2018 |
| WO | WO 2019/079718 A1 | 4/2019 |

OTHER PUBLICATIONS

Chin, J. X., Chung, B. K. S., & Lee, D. Y. (2014). Codon Optimization OnLine (COOL): a web-based multi-objective optimization platform for synthetic gene design. Bioinformatics, 30(15), 2210-2212. (Year: 2014).*
Jha et al., 2007, "The role of complement system in ocular diseases including uveitis and macular degeneration," Mol Immunol 44(16):3901-3908.
"Complement factor I isoform 2 preproprotein [*Homo sapiens*]," DATABASE NCBI [Online], Accession No. NP_000195, 2018, 4 pages total.
"*Homo sapiens* complement factor I (CFI), transcript variant 2, mRNA," DATABASE NCBI [Online], Accession No. NM_000204, 2018, 6 pages total.
"JP 2015516143-A/112869: Modified Polynucleotides for the Production of Proteins Associated With Human Disease," Database EMBL [Online], EBI accession No. EM PAT:LF518498, Oct. 29, 2016, XP002798767, 2 pages total.
"Therapeutic protein CFI codon optimized RNA SEQ:28198," DATABASE Genseq [Online], EBI Accession No. GS NUC:BFB51614, Apr. 5, 2018, XP002798768, 2 pages total.
"Therapeutic protein CFI codon optimized RNA SEQ:41255," DATABASE Genseq [Online],EBI accession No. GS NUC:BFB64671, Apr. 5, 2018, XP002798769, 2 pages total.
Clark et al., "Role of Factor H and Related Proteins in Regulating Complement Activation in the Macula, and Relevance to Age-Related Macular Degeneration," Journal of Clinical Medicine, vol. 4, Published Dec. 26, 2014, pp. 18-31.
Allocca et al., 2007, "Novel Adeno-Associated Virus Serotypes Efficiently Tranduce Murine Photoreceptors," J. Virol. 81:11372-80.
Altschul et al., 1990, "Basic local alignment search tool," J Mol Biol 215(3):403-410.

(Continued)

*Primary Examiner* — Jennifer Dunston
*Assistant Examiner* — Christina Tran
(74) *Attorney, Agent, or Firm* — Biospark Intellectual Property Law

(57) ABSTRACT

An isolated polynucleotide comprising a nucleotide sequence encoding a codon-optimised Complement Factor I (CFI).

6 Claims, 6 Drawing Sheets
Specification includes a Sequence Listing.

(56) References Cited

OTHER PUBLICATIONS

Ausubel et al., 1995, "Current Protocols in Molecular Biology," John Wiley & Sons.

Bainbridge et al., 2008, "Effect of Gene Therapy on Visual Function in Leber's Congenital Amaurosis," N. Engl. J. Med. 358: 2231-2239.

Booij et al., 2010, "A new strategy to identify and annotate human RPE-specific gene expression," PLOS ONE 5(5):9341.

Bressler et al., 1999, "Photodynamic Therapy of Subfoveal Choroidal Neovascularization in Age-related Macular Degeneration with Verteporfin," Arch Ophthalmol 117: 1329-1345.

Brown et al., 2006 "Ranibizumab versus Verteporfin for Neovascular Age-Related Macular Degeneration," N Engl J Med 355:1432-1444.

Cashman et al., 2015, "Adenovirus-mediated delivery of Factor H attenuates complement C3 induced pathology in the murine retina: a potential gene therapy for age-related macular degeneration," J. Gene Medicine 17:229-243.

Choi et al., 2005, "AAV Hybrid Serotypes: Improved Vectors for Gene Delivery," Current Gene Therapy 5(3):299-310.

Choi et al., 2014, "Optimization of AAV expression cassettes to improve packaging capacity and transgene expression in neurons," Molecular Brain 7:17.

Clark et al., 2015, "Role of Factor H and Related Proteins I Regulating Complement Activation in the Macula, and Relevance to Age-Related Macular Degeneration," J Clin Med 4:18-31.

Degn et al., 2011, "Disease-causing mutations in genes of the complement system," Am J Hum Genet 88:689-705.

Devereux et al., 1984, "A comprehensive set of sequence analysis programs for the VAX," Nucleic Acids Res 12(1 Part 1):387-395.

Dong et al., 1996, "Quantitative Analysis of the Packaging Capacity of Recombinant Adeno-Associated Virus," Human Gene Therapy 7(17):2101-2112.

Dos Santos and Nardi, 2007, "The state of the art of adeno-associated virus-based vectors in gene therapy," Virology Journal 4: 99.

Esumi et al., 2004, "Analysis of the VMD2 Promoter and Implication of E-box Binding Factors in Its Regulation," J. Biol. Chem. 279:19064-19073.

Gait, 1984, "Oligonucleotide Synthesis: A Practical Approach," IRL Press.

Goldberger et al., 1987, "Human Complement Factor I: Analysis of cDNA-derived Primary Structure and Assignment of its Gene to Chromosome 4," J Biol. Chem. 262(21):10065-10071.

Gragoudas et al., 2004, "Pegaptanib for Neovascular Age-Related Macular Degeneration," N Engl J Med 351: 2805-2816.

Harrison, 1996, "Purification, Assay, and Characterization of Complement Proteins from Plasma," in Herzenberg L A & Weir D M (eds), Weir's Handbook of Experimental Immunology 5(75): 36-37.

Hsiung L-M et al., 1982, "Purification of human C3b inactivator by monoclonal-antibody affinity chromatography," Biochem J. 203:293-298.

Kavanagh et al., 2015, "Rare genetic variants in the CFI gene are associated with advanced age-related macular degeneration and commonly result in reduced serum factor I levels," Human Mol Genet 24:3861-3870.

Lachmann, 2009, "The amplification loop of the complement pathways," Adv. Immunol. 104:115-149.

Lachmann & Hobart, 1978, "Handbook of Experimental Immunology," chapter 5A in "Complement Technology", 17 pages.

Laughlin et al., 1979, "Spliced adenovirus-associated virus RNA," Proc. Natl. Acad. Sci. 76(11):5567-5571.

Lilley et al., 1992, Methods in Enzymology, vol. 211, DNA Structures, Part A "Synthesis and Physical Analysis of DNA", Academic Press.

Mancuso et al., 2009, "Gene therapy for red-green colour blindness in adult primates," Nature 461(7265):784-787.

Nilsson et al., 2011, "Complement factor I in health and disease," Molecular Immunology 48:1611-1620.

Polak, 1990, "Situ Hybridization: Principles and Practice," Oxford University Press.

Roe et al., 1996, "DNA Isolation and Sequencing: Essential Techniques," John Wiley & Sons.

Roversi et al., 2011, "Structural basis for complement factor I control and its disease- associated sequence polymorphisms," Proc Nat Acad Sci 108:12839-12844.

Sambrook and Maniatis, 1989, "Molecular Cloning: A Laboratory Manual," Cold Spring Harbor Laboratory Press.

Schmidt et al., 2008, "A New Map of Glycosaminoglycan and C3b Binding Sites on Factor H," Journal of Immunology 181:2610-2619.

Seddon, 2001, "Epidemiology of age-related macular degeneration,". in Ogden, T.E., et al., eds. Ryan S.J., ed-in-chief. Retina vol. II. 3rd ed. St. Louis, Mo.: Mosby; 2001: 1039-1050.

Tatusova et al., 1999, "BLAST 2 SEQUENCES, a new tool for comparing protein and nucleotide sequences," FEMS Microbiology Letters 174(2):247-250.

Tufail et al., 2010, "Bevacizumab for neovascular age related macular degeneration (ABC Trial): multicentre randomised double masked study," BMJ 340: c2459.

"UniProtKB," Database accession No. P08603, Jan. 16, 2019.

Wu et al., 2006, "Adeno-associated virus serotypes: vector toolkit for human gene therapy," Molecular Therapy 14:316-27.

Hallam, et al, 2024, "Ocular biomarker profiling after complement factor I gene therapy in geographic atrophy secondary to age-related macular degeneration," eLife 13:RP99806.

UniProtKB—P05156 (CFAI_HUMAN), Accession No. P05616, accessed from uniprot.org/uniprotkb/P05156/entry on Dec. 20, 2024.

Ahmad et al., 2018, "P135: Reduced activity of the complement system through elevation of complement factor I using AAV mediated gene delivery to the liver," Human Gene Therapy 29(12):A67 (poster presentation abstract, 1 page).

* cited by examiner

CFI expression in ARPE19 transfected with codon optimised plasmids

FHL-1 in supernatant from ARPE19 transduced with codon optimised vectors

SEQUENCE LISTING

<160> NUMBER OF SEQ ID NOS: 35

<210> SEQ ID NO 1
<211> LENGTH: 583
<212> TYPE: PRT
<213> ORGANISM: Homo sapiens

<400> SEQUENCE: 1

```
Met Lys Leu Leu His Val Phe Leu Leu Phe Leu Cys Phe His Leu Arg
1               5                   10                  15

Phe Cys Lys Val Thr Tyr Thr Ser Gln Glu Asp Leu Val Glu Lys Lys
            20                  25                  30

Cys Leu Ala Lys Lys Tyr Thr His Leu Ser Cys Asp Lys Val Phe Cys
        35                  40                  45

Gln Pro Trp Gln Arg Cys Ile Glu Gly Thr Cys Val Cys Lys Leu Pro
    50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
            115                 120                 125

Val Lys Leu Val Asp Gln Asp Lys Thr Met Phe Ile Cys Lys Ser Ser
    130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
            195                 200                 205

Phe Ala Asp Val Val Cys Tyr Thr Gln Lys Ala Asp Ser Pro Met Asp
    210                 215                 220

Asp Phe Phe Gln Cys Val Asn Gly Lys Tyr Ile Ser Gln Met Lys Ala
225                 230                 235                 240

Cys Asp Gly Ile Asn Asp Cys Gly Asp Gln Ser Asp Glu Leu Cys Cys
            245                 250                 255

Lys Ala Cys Gln Gly Lys Gly Phe His Cys Lys Ser Gly Val Cys Ile
            260                 265                 270

Pro Ser Gln Tyr Gln Cys Asn Gly Glu Val Asp Cys Ile Thr Gly Glu
        275                 280                 285

Asp Glu Val Gly Cys Ala Gly Phe Ala Ser Val Thr Gln Glu Glu Thr
    290                 295                 300

Glu Ile Leu Thr Ala Asp Met Asp Ala Glu Arg Arg Arg Ile Lys Ser
305                 310                 315                 320

Leu Leu Pro Lys Leu Ser Cys Gly Val Lys Asn Arg Met His Ile Arg
            325                 330                 335

Arg Lys Arg Ile Val Gly Gly Lys Arg Ala Gln Leu Gly Asp Leu Pro
            340                 345                 350

Trp Gln Val Ala Ile Lys Asp Ala Ser Gly Ile Thr Cys Gly Gly Ile
        355                 360                 365
```

-continued

```
Tyr Ile Gly Gly Cys Trp Ile Leu Thr Ala Ala His Cys Leu Arg Ala
    370             375             380

Ser Lys Thr His Arg Tyr Gln Ile Trp Thr Thr Val Val Asp Trp Ile
385             390             395             400

His Pro Asp Leu Lys Arg Ile Val Ile Glu Tyr Val Asp Arg Ile Ile
            405             410             415

Phe His Glu Asn Tyr Asn Ala Gly Thr Tyr Gln Asn Asp Ile Ala Leu
            420             425             430

Ile Glu Met Lys Lys Asp Gly Asn Lys Lys Asp Cys Glu Leu Pro Arg
        435             440             445

Ser Ile Pro Ala Cys Val Pro Trp Ser Pro Tyr Leu Phe Gln Pro Asn
    450             455             460

Asp Thr Cys Ile Val Ser Gly Trp Gly Arg Glu Lys Asp Asn Glu Arg
465             470             475             480

Val Phe Ser Leu Gln Trp Gly Glu Val Lys Leu Ile Ser Asn Cys Ser
            485             490             495

Lys Phe Tyr Gly Asn Arg Phe Tyr Glu Lys Glu Met Glu Cys Ala Gly
            500             505             510

Thr Tyr Asp Gly Ser Ile Asp Ala Cys Lys Gly Asp Ser Gly Gly Pro
            515             520             525

Leu Val Cys Met Asp Ala Asn Asn Val Thr Tyr Val Trp Gly Val Val
    530             535             540

Ser Trp Gly Glu Asn Cys Gly Lys Pro Glu Phe Pro Gly Val Tyr Thr
545             550             555             560

Lys Val Ala Asn Tyr Phe Asp Trp Ile Ser Tyr His Val Gly Arg Pro
            565             570             575

Phe Ile Ser Gln Tyr Asn Val
            580
```

```
<210> SEQ ID NO 2
<211> LENGTH: 1752
<212> TYPE: DNA
<213> ORGANISM: Homo sapiens

<400> SEQUENCE: 2
atgaagcttc ttcatgtttt cctgttattt ctgtgcttcc acttaaggtt ttgcaaggtc      60
acttatacat ctcaagagga tctggtggag aaaaagtgct tagcaaaaaa atatactcac     120
ctctcctgcg ataaagtctt ctgccagcca tggcagagat gcattgaggg cacctgtgtt     180
tgtaaactac cgtatcagtg cccaaagaat ggcactgcag tgtgtgcaac taacaggaga     240
agcttcccaa catactgtca acaaaagagt ttggaatgtc ttcatccagg acaaagtttt     300
ttaaataacg aacatgcac agccgaagga agtttagtg tttccttgaa gcatggaaat      360
acagattcag agggaatagt tgaagtaaaa cttgtggacc aagataagac aatgttcata     420
tgcaaaagca gctggagcat gagggaagcc aacgtggcct gccttgacct tgggtttcaa     480
caaggtgctg atactcaaag aaggtttaag ttgtctgatc tctctataaa ttccactgaa     540
tgtctacatg tgcattgccg aggattagag accagtttgg ctgaatgtac ttttactaag     600
agaagaacta tgggttacca ggatttcgct gatgtggttt gttatacaca gaaagcagat     660
tctccaatgg atgacttctt tcagtgtgtg aatgggaaat acatttctca gatgaaagcc     720
tgtgatggta tcaatgattg tggagaccaa agtgatgaac tgtgttgtaa agcatgccaa     780
ggcaaaggct tccattgcaa atcgggtgtt tgcattccaa gccagtatca atgcaatggt     840
gaggtggact gcattacagg ggaagatgaa gttggctgtg caggctttgc atctgtggct     900
```

-continued

```
caagaagaaa cagaaatttt gactgctgac atggatgcag aaagaagacg gataaaatca   960
ttattaccta aactatcttg tggagttaaa aacagaatgc acattcgaag gaaacgaatt  1020
gtgggaggaa agcgagcaca actgggagac ctcccatggc aggtggcaat taaggatgcc  1080
agtggaatca cctgtggggg aatttatatt ggtggctgtt ggattctgac tgctgcacat  1140
tgtctcagag ccagtaaaac tcatcgttac caaatatgga caacagtagt agactggata  1200
caccccgacc ttaaacgtat agtaattgaa tacgtggata gaattatttt ccatgaaaac  1260
tacaatgcag gcacttacca aaatgacatc gctttgattg aaatgaaaaa agacggaaac  1320
aaaaaagatt gtgagctgcc tcgttccatc cctgcctgtg tccctggtc tccttaccta  1380 ttccaaccta atgatacatg catcgtttct ggctggggac gagaaaaaga taacgaaaga  1440 gtctttttcac ttcagtgggg tgaagttaaa ctaataagca actgctctaa gttttacgga  1500
aatcgtttct atgaaaaaga aatggaatgt gcaggtacat atgatggttc catcgatgcc  1560
tgtaaagggg actctggagg cccccttagtc tgtatggatg ccaacaatgt gacttatgtc  1620
tggggtgttg tgagttgggg ggaaaactgt ggaaaaccag agttcccagg tgtttacacc  1680
aaagtggcca attattttga ctggattagc taccatgtag gaaggccttt tatttctcag  1740
tacaatgtat aa                                                     1752
```

<210> SEQ ID NO 3
<211> LENGTH: 1231
<212> TYPE: PRT
<213> ORGANISM: Homo sapiens

<400> SEQUENCE: 3

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
```

-continued

```
                210               215               220

Ile Ile Tyr Lys Glu Asn Glu Arg Phe Gln Tyr Lys Cys Asn Met Gly
225               230               235               240

Tyr Glu Tyr Ser Glu Arg Gly Asp Ala Val Cys Thr Glu Ser Gly Trp
              245               250               255

Arg Pro Leu Pro Ser Cys Glu Glu Lys Ser Cys Asp Asn Pro Tyr Ile
              260               265               270

Pro Asn Gly Asp Tyr Ser Pro Leu Arg Ile Lys His Arg Thr Gly Asp
              275               280               285

Glu Ile Thr Tyr Gln Cys Arg Asn Gly Phe Tyr Pro Ala Thr Arg Gly
    290               295               300

Asn Thr Ala Lys Cys Thr Ser Thr Gly Trp Ile Pro Ala Pro Arg Cys
305               310               315               320

Thr Leu Lys Pro Cys Asp Tyr Pro Asp Ile Lys His Gly Gly Leu Tyr
              325               330               335

His Glu Asn Met Arg Arg Pro Tyr Phe Pro Val Ala Val Gly Lys Tyr
              340               345               350

Tyr Ser Tyr Tyr Cys Asp Glu His Phe Glu Thr Pro Ser Gly Ser Tyr
              355               360               365

Trp Asp His Ile His Cys Thr Gln Asp Gly Trp Ser Pro Ala Val Pro
    370               375               380

Cys Leu Arg Lys Cys Tyr Phe Pro Tyr Leu Glu Asn Gly Tyr Asn Gln
385               390               395               400

Asn Tyr Gly Arg Lys Phe Val Gln Gly Lys Ser Ile Asp Val Ala Cys
              405               410               415

His Pro Gly Tyr Ala Leu Pro Lys Ala Gln Thr Thr Val Thr Cys Met
              420               425               430

Glu Asn Gly Trp Ser Pro Thr Pro Arg Cys Ile Arg Val Lys Thr Cys
              435               440               445

Ser Lys Ser Ser Ile Asp Ile Glu Asn Gly Phe Ile Ser Glu Ser Gln
    450               455               460

Tyr Thr Tyr Ala Leu Lys Glu Lys Ala Lys Tyr Gln Cys Lys Leu Gly
465               470               475               480

Tyr Val Thr Ala Asp Gly Glu Thr Ser Gly Ser Ile Thr Cys Gly Lys
              485               490               495

Asp Gly Trp Ser Ala Gln Pro Thr Cys Ile Lys Ser Cys Asp Ile Pro
              500               505               510

Val Phe Met Asn Ala Arg Thr Lys Asn Asp Phe Thr Trp Phe Lys Leu
              515               520               525

Asn Asp Thr Leu Asp Tyr Glu Cys His Asp Gly Tyr Glu Ser Asn Thr
    530               535               540

Gly Ser Thr Thr Gly Ser Ile Val Cys Gly Tyr Asn Gly Trp Ser Asp
545               550               555               560

Leu Pro Ile Cys Tyr Glu Arg Glu Cys Glu Leu Pro Lys Ile Asp Val
              565               570               575

His Leu Val Pro Asp Arg Lys Lys Asp Gln Tyr Lys Val Gly Glu Val
              580               585               590

Leu Lys Phe Ser Cys Lys Pro Gly Phe Thr Ile Val Gly Pro Asn Ser
              595               600               605

Val Gln Cys Tyr His Phe Gly Leu Ser Pro Asp Leu Pro Ile Cys Lys
    610               615               620

Glu Gln Val Gln Ser Cys Gly Pro Pro Pro Glu Leu Leu Asn Gly Asn
625               630               635               640
```

```
Val Lys Glu Lys Thr Lys Glu Glu Tyr Gly His Ser Glu Val Val Glu
                645             650             655

Tyr Tyr Cys Asn Pro Arg Phe Leu Met Lys Gly Pro Asn Lys Ile Gln
            660             665             670

Cys Val Asp Gly Glu Trp Thr Thr Leu Pro Val Cys Ile Val Glu Glu
        675             680             685

Ser Thr Cys Gly Asp Ile Pro Glu Leu Glu His Gly Trp Ala Gln Leu
    690             695             700

Ser Ser Pro Pro Tyr Tyr Tyr Gly Asp Ser Val Glu Phe Asn Cys Ser
705             710             715             720

Glu Ser Phe Thr Met Ile Gly His Arg Ser Ile Thr Cys Ile His Gly
            725             730             735

Val Trp Thr Gln Leu Pro Gln Cys Val Ala Ile Asp Lys Leu Lys Lys
        740             745             750

Cys Lys Ser Ser Asn Leu Ile Ile Leu Glu Glu His Leu Lys Asn Lys
        755             760             765

Lys Glu Phe Asp His Asn Ser Asn Ile Arg Tyr Arg Cys Arg Gly Lys
    770             775             780

Glu Gly Trp Ile His Thr Val Cys Ile Asn Gly Arg Trp Asp Pro Glu
785             790             795             800

Val Asn Cys Ser Met Ala Gln Ile Gln Leu Cys Pro Pro Pro Gln
            805             810             815

Ile Pro Asn Ser His Asn Met Thr Thr Thr Leu Asn Tyr Arg Asp Gly
            820             825             830

Glu Lys Val Ser Val Leu Cys Gln Glu Asn Tyr Leu Ile Gln Glu Gly
            835             840             845

Glu Glu Ile Thr Cys Lys Asp Gly Arg Trp Gln Ser Ile Pro Leu Cys
    850             855             860

Val Glu Lys Ile Pro Cys Ser Gln Pro Pro Gln Ile Glu His Gly Thr
865             870             875             880

Ile Asn Ser Ser Arg Ser Ser Gln Glu Ser Tyr Ala His Gly Thr Lys
            885             890             895

Leu Ser Tyr Thr Cys Glu Gly Gly Phe Arg Ile Ser Glu Glu Asn Glu
            900             905             910

Thr Thr Cys Tyr Met Gly Lys Trp Ser Ser Pro Pro Gln Cys Glu Gly
            915             920             925

Leu Pro Cys Lys Ser Pro Pro Glu Ile Ser His Gly Val Val Ala His
    930             935             940

Met Ser Asp Ser Tyr Gln Tyr Gly Glu Glu Val Thr Tyr Lys Cys Phe
945             950             955             960

Glu Gly Phe Gly Ile Asp Gly Pro Ala Ile Ala Lys Cys Leu Gly Glu
            965             970             975

Lys Trp Ser His Pro Pro Ser Cys Ile Lys Thr Asp Cys Leu Ser Leu
            980             985             990

Pro Ser Phe Glu Asn Ala Ile Pro  Met Gly Glu Lys Lys  Asp Val Tyr
            995             1000            1005

Lys Ala  Gly Glu Gln Val Thr  Tyr Thr Cys Ala Thr  Tyr Tyr Lys
    1010            1015            1020

Met Asp  Gly Ala Ser Asn Val  Thr Cys Ile Asn Ser  Arg Trp Thr
    1025            1030            1035

Gly Arg  Pro Thr Cys Arg Asp  Thr Ser Cys Val Asn  Pro Pro Thr
    1040            1045            1050
```

-continued

```
Val Gln  Asn Ala Tyr Ile Val  Ser Arg Gln Met Ser  Lys Tyr Pro
    1055             1060               1065

Ser Gly  Glu Arg Val Arg Tyr  Gln Cys Arg Ser Pro  Tyr Glu Met
    1070             1075               1080

Phe Gly  Asp Glu Glu Val Met  Cys Leu Asn Gly Asn  Trp Thr Glu
    1085             1090               1095

Pro Pro  Gln Cys Lys Asp Ser  Thr Gly Lys Cys Gly  Pro Pro Pro
    1100             1105               1110

Pro Ile  Asp Asn Gly Asp Ile  Thr Ser Phe Pro Leu  Ser Val Tyr
    1115             1120               1125

Ala Pro  Ala Ser Ser Val Glu  Tyr Gln Cys Gln Asn  Leu Tyr Gln
    1130             1135               1140

Leu Glu  Gly Asn Lys Arg Ile  Thr Cys Arg Asn Gly  Gln Trp Ser
    1145             1150               1155

Glu Pro  Pro Lys Cys Leu His  Pro Cys Val Ile Ser  Arg Glu Ile
    1160             1165               1170

Met Glu  Asn Tyr Asn Ile Ala  Leu Arg Trp Thr Ala  Lys Gln Lys
    1175             1180               1185

Leu Tyr  Ser Arg Thr Gly Glu  Ser Val Glu Phe Val  Cys Lys Arg
    1190             1195               1200

Gly Tyr  Arg Leu Ser Ser Arg  Ser His Thr Leu Arg  Thr Thr Cys
    1205             1210               1215

Trp Asp  Gly Lys Leu Glu Tyr  Pro Thr Cys Ala Lys  Arg
    1220             1225               1230
```

```
<210> SEQ ID NO 4
<211> LENGTH: 3696
<212> TYPE: DNA
<213> ORGANISM: Homo sapiens

<400> SEQUENCE: 4
atgagacttc tagcaaagat tatttgcctt atgttatggg ctatttgtgt agcagaagat      60
tgcaatgaac ttcctccaag aagaaataca gaaattctga caggttcctg gtctgaccaa     120
acatatccag aaggcacccca ggctatctat aaatgccgcc ctggatatag atctcttgga     180
aatgtaataa tggtatgcag gaagggagaa tgggttgctc ttaatccatt aaggaaatgt     240 cagaaaggc cctgtggaca tcctggagat actccttttg gtacttttac ccttacagga     300
ggaaatgtgt ttgaatatgg tgtaaaagct gtgtatacat gtaatgaggg gtatcaattg     360
ctaggtgaga ttaattaccg tgaatgtgac acagatggat ggaccaatga tattcctata     420
tgtgaagttg tgaagtgttt accagtgaca gcaccagaga atggaaaaat tgtcagtagt     480
gcaatggaac cagatcggga ataccatttt ggacaagcag tacggtttgt atgtaactca     540
ggctacaaga ttgaaggaga tgaagaaatg cattgttcag acgatggttt ttggagtaaa     600
gagaaaccaa agtgtgtgga aatttcatgc aaatccccag atgttataaa tggatctcct     660
atatctcaga agattattta taaggagaat gaacgatttc aatataaatg taacatgggt     720
tatgaataca gtgaaagagg agatgctgta tgcactgaat ctggatggcg tccgttgcct     780
tcatgtgaag aaaaatcatg tgataatcct tatattccaa atggtgacta ctcaccttta     840
aggattaaac acagaactgg agatgaaatc acgtaccagt gtagaaatgg ttttttatcct     900 gcaacccggg gaaatacagc aaaatgcaca agtactggct ggataccctgc tccgagatgt     960 accttgaaac cttgtgatta tccagacatt aaacatggag gtctatatca tgagaatatg    1020
cgtagaccat actttccagt agctgtagga aaatattact cctattactg tgatgaacat    1080
```

-continued

```
tttgagactc cgtcaggaag ttactgggat cacattcatt gcacacaaga tggatggtcg   1140
ccagcagtac catgcctcag aaaatgttat tttccttatt tggaaaatgg atataatcaa   1200
aatcatggaa gaaagtttgt acagggtaaa tctatagacg ttgcctgcca tcctggctac   1260
gctcttccaa aagcgcagac cacagttaca tgtatggaga atggctggtc tcctactccc   1320
agatgcatcc gtgtcaaaac atgttccaaa tcaagtatag atattgagaa tgggtttatt   1380
tctgaatctc agtatacata tgccttaaaa gaaaaagcga aatatcaatg caaactagga   1440
tatgtaacag cagatggtga aacatcagga tcaattacat gtgggaaaga tggatggtca   1500
gctcaaccca cgtgcattaa atcttgtgat atcccagtat ttatgaatgc cagaactaaa   1560
aatgacttca catggtttaa gctgaatgac acattggact atgaatgcca tgatggttat   1620
gaaagcaata ctggaagcac cactggttcc atagtgtgtg gttacaatgg ttggtctgat   1680
ttacccatat gttatgaaag agaatgcgaa cttcctaaaa tagatgtaca cttagttcct   1740
gatcgcaaga aagaccagta taaagttgga gaggtgttga aattctcctg caaaccagga   1800
tttacaatag ttggacctaa ttccgttcag tgctaccact ttggattgtc tcctgacctc   1860
ccaatatgta aagagcaagt acaatcatgt ggtccacctc ctgaactcct caatgggaat   1920
gttaaggaaa aaacgaaaga agaatatgga cacagtgaag tggtggaata ttattgcaat   1980
cctagatttc taatgaaggg acctaataaa attcaatgtg ttgatggaga gtggacaact   2040
ttaccagtgt gtattgtgga ggagagtacc tgtggagata tacctgaact tgaacatggc   2100
tgggcccagc tttcttcccc tccttattac tatggagatt cagtggaatt caattgctca   2160
gaatcattta caatgattgg acacagatca attacgtgta ttcatggagt atggaccccaa   2220 cttccccagt gtgtggcaat agataaactt aagaagtgca aatcatcaaa tttaattata   2280
cttgaggaac atttaaaaaa caagaaggaa ttcgatcata attctaacat aaggtacaga   2340
tgtagaggaa aagaaggatg gatacacaca gtctgcataa atggaagatg ggatccagaa   2400
gtgaactgct caatggcaca aatacaatta tgcccacctc cacctcagat tcccaattct   2460
cacaatatga caaccacact gaattatcgg gatggagaaa aagtatctgt tctttgccaa   2520
gaaaattatc taattcagga aggagaagaa attacatgca aagatggaag atggcagtca   2580
ataccactct gtgttgaaaa aattccatgt tcacaaccac ctcagataga acacggaacc   2640
attaattcat ccaggtcttc acaagaaagt tatgcacatg ggactaaatt gagttatact   2700
tgtgagggtg gtttcaggat atctgaagaa aatgaaacaa catgctacat gggaaaatgg   2760
agttctccac ctcagtgtga aggccttcct tgtaaatctc cacctgagat ttctcatggt   2820
gttgtagctc acatgtcaga cagttatcag tatggagaag aagttacgta caatgtttt   2880 gaaggttttg gaattgatgg gcctgcaatt gcaaaatgct taggagaaaa atggtctcac   2940
cctccatcat gcataaaaac agattgtctc agtttaccta gctttgaaaa tgccataccc   3000
atgggagaga agaaggatgt gtataaggcg ggtgagcaag tgacttacac ttgtgcaaca   3060
tattacaaaa tggatggagc cagtaatgta acatgcatta atagcagatg gacaggaagg   3120
ccaacatgca gagacacctc ctgtgtgaat ccgcccacag tacaaatgc ttatatagtg   3180 tcgagacaga tgagtaaata tccatctggt gagagagtac gttatcaatg taggagccct   3240
tatgaaatgt ttgggatga agaagtgatg tgtttaaatg gaaactggac ggaaccacct   3300
caatgcaaag attctacagg aaaatgtggg cccctccac ctattgacaa tggggacatt   3360
acttcattcc cgttgtcagt atatgctcca gcttcatcag ttgagtacca atgccagaac   3420
```

-continued

```
ttgtatcaac ttgagggtaa caagcgaata acatgtagaa atggacaatg gtcagaacca      3480
ccaaaatgct tacatccgtg tgtaatatcc cgagaaatta tggaaaatta taacatagca      3540
ttaaggtgga cagccaaaca gaagctttat tcgagaacag gtgaatcagt tgaatttgtg      3600
tgtaaacggg gatatcgtct ttcatcacgt tctcacacat tgcgaacaac atgttgggat      3660
gggaaactgg agtatccaac ttgtgcaaaa agatag                                3696

<210> SEQ ID NO 5
<211> LENGTH: 934
<212> TYPE: DNA
<213> ORGANISM: Artificial Sequence
<220> FEATURE:
<223> OTHER INFORMATION: example promoter sequence

<400> SEQUENCE: 5
attgacgtca ataatgacgt atgttcccat agtaacgcca atagggactt tccattgacg       60
tcaatgggtg gagtatttac ggtaaactgc ccacttggca gtacatcaag tgtatcatat      120
gccaagtacg ccccctattg acgtcaatga cggtaaatgg cccgcctggc attatgccca      180
gtacatgacc ttatgggact ttcctacttg gcagtacatc tacgtattag tcatcgctat      240
taccatggtc gaggtgagcc ccacgttctg cttcactctc cccatctccc cccccctcccc     300 acccccaatt ttgtatttat ttatttttta attattttgt gcagcgatgg gggcggggggg     360 gggggggggg cgcgcgccag gcggggcggg gcggggcgag gggcggggcg gggcgaggcg      420
gagaggtgcg gcggcagcca atcagagcgg cgcgctccga aagtttcctt ttatggcgag      480
gcggcggcgg cggcggccct ataaaaagcg aagcgcgcgg cgggcgggag tcgctgcgcg      540
ctgccttcgc cccgtgcccc gctccgccgc cgcctcgcgc cgcccgcccc ggctctgact      600
gaccgcgtta ctcccacagg tgagcgggcg ggacggccct tctcctccgg gctgtaatta      660
gcgcttggtt taatgacggc ttgtttcttt tctgtggctg cgtgaaagcc ttgaggggct      720
ccgggagggc cctttgtgcg ggggggagcgg ctcggggctg tccgcggggg gacggctgcc     780 ttcgggggggg acgggcagg gcggggttcg gcttctggcg tgtgaccggc ggctctagag      840
cctctgctaa ccatgttcat gccttcttct ttttcctaca gctcctgggc aacgtgctgg      900
ttattgtgct gtctcatcat tttggcaaag aatt                                  934

<210> SEQ ID NO 6
<211> LENGTH: 270
<212> TYPE: DNA
<213> ORGANISM: Artificial Sequence
<220> FEATURE:
<223> OTHER INFORMATION: Bovine Growth Hormone poly-A (bGH poly-A)
      signal sequence

<400> SEQUENCE: 6
tcgctgatca gcctcgactg tgccttctag ttgccagcca tctgttgttt gcccctcccc       60
cgtgccttcc ttgaccctgg aaggtgccac tcccactgtc ctttcctaat aaaatgagga      120
aattgcatcg cattgtctga gtaggtgtca ttctattctg gggggtgggg tggggcagga      180
cagcaagggg gaggattggg aagacaatag caggcatgct ggggatgcgg tgggctctat      240
ggcttctgag gcggaaagaa ccagctgggg                                       270

<210> SEQ ID NO 7
<211> LENGTH: 588
<212> TYPE: DNA
<213> ORGANISM: Artificial Sequence
<220> FEATURE:
```

<223> OTHER INFORMATION: example woodchuck hepatitis post-
      transcriptional regulatory element (WPRE) sequence

<400> SEQUENCE: 7
atcaacctct ggattacaaa atttgtgaaa gattgactgg tattcttaac tatgttgctc        60
cttttacgct atgtggatac gctgctttaa tgcctttgta tcatgctatt gcttcccgta       120
tggctttcat tttctcctcc ttgtataaat cctggttgct gtctctttat gaggagttgt       180
ggcccgttgt caggcaacgt ggcgtggtgt gcactgtgtt tgctgacgca accccactg       240 gttggggcat tgccaccacc tgtcagctcc tttccgggac tttcgctttc ccctccta       300 ttgccacggc ggaactcatc gccgcctgcc ttgcccgctg ctggacaggg gctcggctgt       360
tgggcactga caattccgtg gtgttgtcgg ggaaatcatc gtcctttcct tggctgctcg       420
cctgtgttgc cacctggatt ctgcgcggga cgtccttctg ctacgtccct tcggccctca       480
atccagcgga ccttccttcc cgcggcctgc tgccggctct gcggcctctt ccgcgtcttc       540
gccttcgccc tcagacgagt cggatctccc tttgggccgc ctccccgc                    588

<210> SEQ ID NO 8
<211> LENGTH: 1752
<212> TYPE: DNA
<213> ORGANISM: Artificial Sequence
<220> FEATURE:
<223> OTHER INFORMATION: codon-optimised nucleotide sequence encoding
      Complement Factor I

<400> SEQUENCE: 8
atgaagctgc tgcatgtctt tctgctgttt ctgtgcttcc atctgcggtt ctgtaaagtg        60
acctatacta gccaggagga tctggtggag aagaagtgtc tggccaagaa gtacacacac       120
ctgagctgcg acaaggtgtt ctgtcagcct tggcagcggt gcatcgaggg cacctgcgtg       180
tgcaagctgc cttaccagtg cccaaagaac ggcaccgccg tgtgcgccac aaatcggaga       240
tcttttccaa catattgcca gcagaagagc ctggagtgtc tgcaccccgg caccaagttc       300
ctgaacaatg gcacctgcac agccgagggc aagtttttctg tgagcctgaa gcacggcaac       360
acagatagcg agggcatcgt ggaggtgaag ctggtggacc aggataagac catgttcatc       420
tgtaagagct cctggtccat gagggaggca aacgtggcat gcctggatct gggattccag       480 caggagcag acacacagag gcgctttaag ctgtccgacc tgtctatcaa tagcaccgag       540
tgcctgcacg tgcactgtag gggcctggag acatccctgg cagagtgcac cttcacaaag       600
cggagaacca tgggctacca ggactttgcc gacgtggtgt gctataccca gaaggccgat       660
agccccatgg acgatttctt tcagtgcgtg aacggcaagt atatctccca gatgaaggcc       720
tgcgacggca tcaatgactg tggcgatcag tctgacgagc tgtgctgtaa ggcctgtcag       780
ggcaagggct tccactgcaa gagcggcgtg tgcatccctt cccagtacca gtgcaacggc       840
gaggtggatt gtatcacagg agaggacgaa gtgggatgcg caggatttgc atctgtggca       900
caggaggaga cagagatcct gacagccgac atggatgccg agaggcgccg gatcaagtct       960
ctgctgccta agctgagctg tggcgtgaag aatcggatgc acatcagaag gaagcgcatc      1020
gtgggaggca gagaggcaca gctgggcgat ctgccatggc aggtggccat caaggacgcc      1080
tctggcatca cctgcggcgg catctacatc ggaggatgtt ggatcctgac cgcagcacac      1140
tgcctgagag caagcaagac acacaggtat cagatctgga ccacagtggt ggattggatc      1200
cacccagacc tgaagagaat cgtgatcgag tacgtggata ggatcatctt tcacgagaac      1260
tacaatgccg gcacatatca gaacgacatc gccctgatcg agatgaagaa ggatggcaat      1320

-continued

```
aagaaggact gtgagctgcc cagatccatc cctgcatgcg tgccatggag cccctatctg    1380
ttccagccca acgatacctg catcgtgtcc ggatggggaa gggagaagga caatgagcgg    1440 gtgtttttctc tgcagtgggg cgaggtgaag ctgatctcca actgttctaa gttctacggc    1500
aataggtttt atgagaagga gatggagtgc gccggcacct acgatggcag catcgacgcc    1560
tgtaagggcg attccggagg accactggtg tgcatggacg caaacaatgt gacatacgtg    1620
tggggagtgg tgtcctgggg agagaactgc ggcaagccag agttccccgg cgtatatacc    1680
aaggtggcca attattttga ttggatttcc taccacgtcg gcaggccctt tatttcccag    1740
tataatgtct aa                                                        1752
```

```
<210> SEQ ID NO 9
<211> LENGTH: 583
<212> TYPE: PRT
<213> ORGANISM: Homo sapiens

<400> SEQUENCE: 9

Met Lys Leu Leu His Val Phe Leu Leu Phe Leu Cys Phe His Leu Arg
1               5                   10                  15

Phe Cys Lys Val Thr Tyr Thr Ser Gln Glu Asp Leu Val Glu Lys Lys
            20                  25                  30

Cys Leu Ala Lys Lys Tyr Thr His Leu Ser Cys Asp Lys Val Phe Cys
        35                  40                  45

Gln Pro Trp Gln Arg Cys Ile Glu Gly Thr Cys Val Cys Lys Leu Pro
    50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
        115                 120                 125

Val Lys Leu Val Asp Gln Asp Lys Thr Met Phe Ile Cys Lys Ser Ser
    130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
        195                 200                 205

Phe Ala Asp Val Val Cys Tyr Thr Gln Lys Ala Asp Ser Pro Met Asp
    210                 215                 220

Asp Phe Phe Gln Cys Val Asn Gly Lys Tyr Ile Ser Gln Met Lys Ala
225                 230                 235                 240

Cys Asp Gly Ile Asn Asp Cys Gly Asp Gln Ser Asp Glu Leu Cys Cys
                245                 250                 255

Lys Ala Cys Gln Gly Lys Gly Phe His Cys Lys Ser Gly Val Cys Ile
            260                 265                 270

Pro Ser Gln Tyr Gln Cys Asn Gly Glu Val Asp Cys Ile Thr Gly Glu
        275                 280                 285
```

-continued

```
Asp Glu Val Gly Cys Ala Gly Phe Ala Ser Val Ala Gln Glu Glu Thr
    290                 295                 300

Glu Ile Leu Thr Ala Asp Met Asp Ala Glu Arg Arg Arg Ile Lys Ser
305                 310                 315                 320

Leu Leu Pro Lys Leu Ser Cys Gly Val Lys Asn Arg Met His Ile Arg
                325                 330                 335

Arg Lys Arg Ile Val Gly Gly Lys Arg Ala Gln Leu Gly Asp Leu Pro
                340                 345                 350

Trp Gln Val Ala Ile Lys Asp Ala Ser Gly Ile Thr Cys Gly Gly Ile
            355                 360                 365

Tyr Ile Gly Gly Cys Trp Ile Leu Thr Ala Ala His Cys Leu Arg Ala
    370                 375                 380

Ser Lys Thr His Arg Tyr Gln Ile Trp Thr Thr Val Val Asp Trp Ile
385                 390                 395                 400

His Pro Asp Leu Lys Arg Ile Val Ile Glu Tyr Val Asp Arg Ile Ile
                405                 410                 415

Phe His Glu Asn Tyr Asn Ala Gly Thr Tyr Gln Asn Asp Ile Ala Leu
                420                 425                 430

Ile Glu Met Lys Lys Asp Gly Asn Lys Lys Asp Cys Glu Leu Pro Arg
            435                 440                 445

Ser Ile Pro Ala Cys Val Pro Trp Ser Pro Tyr Leu Phe Gln Pro Asn
    450                 455                 460

Asp Thr Cys Ile Val Ser Gly Trp Gly Arg Glu Lys Asp Asn Glu Arg
465                 470                 475                 480

Val Phe Ser Leu Gln Trp Gly Glu Val Lys Leu Ile Ser Asn Cys Ser
                485                 490                 495

Lys Phe Tyr Gly Asn Arg Phe Tyr Glu Lys Glu Met Glu Cys Ala Gly
                500                 505                 510

Thr Tyr Asp Gly Ser Ile Asp Ala Cys Lys Gly Asp Ser Gly Gly Pro
            515                 520                 525

Leu Val Cys Met Asp Ala Asn Asn Val Thr Tyr Val Trp Gly Val Val
    530                 535                 540

Ser Trp Gly Glu Asn Cys Gly Lys Pro Glu Phe Pro Gly Val Tyr Thr
545                 550                 555                 560

Lys Val Ala Asn Tyr Phe Asp Trp Ile Ser Tyr His Val Gly Arg Pro
                565                 570                 575

Phe Ile Ser Gln Tyr Asn Val
            580
```

```
<210> SEQ ID NO 10
<211> LENGTH: 1752
<212> TYPE: DNA
<213> ORGANISM: Artificial Sequence
<220> FEATURE:
<223> OTHER INFORMATION: nucleotide sequence encoding Complement Factor
      I

<400> SEQUENCE: 10
atgaaactgc tgcatgtctt cctcctcttc ctgtgcttcc acctccgttt ctgtaaagtc        60
acctacacta gccaggagga tctggtggag aagaaatgcc tggccaagaa gtatacccac       120
ctgagctgcg acaaagtgtt ctgccagccc tggcaacgct gcattgaagg tacttgtgtg       180
tgcaagctgc cctaccagtg ccccaagaac ggcacggccg tgtgtgccac caacaggagg       240
agcttcccca cctactgcca gcagaagagc ctggaatgcc tccaccctgg caccaagttt       300
ctgaacaacg ggacctgcac agccgagggg aaattcagcg tctccctcaa gcacggcaat       360
```

-continued

```
acagactccg agggcattgt ggaagtgaag ctggtggacc aggacaagac catgttcatc    420
tgcaaaagca gctggtccat gcgggaggcc aatgtcgcct gcctggacct gggcttccag    480
cagggcgctg atacacagcg ccgctttaaa ctcagtgacc tcagcatcaa cagcactgag    540
tgtctgcacg tgcactgccg gggcctggag accagcctgg ctgagtgcac cttcaccaag    600
cgcaggacca tgggctacca ggattttgca gatgtggtct gctaccccca gaaggcagac    660
agccccatgg atgacttctt ccagtgtgtc aatggcaagt acattcccca gatgaaggct    720
tgtgacggga tcaatgattg cgggatcag agcgatgagc tctgctgcaa ggcctgccaa    780
gggaagggct ttcactgtaa gtctggggtg tgcatccctt ctcagtatca gtgcaacgga    840
gaggtggact gcatcactgg ggaggacgag gtgggctgtg ctggcttcgc ctctgtggcc    900
caggaggaga cagagatcct cacagctgac atggatgcag agcggcggcg catcaagagt    960
ctgctcccaa agctctcctg cggcgttaag aatcgcatgc acatccggag gaagcggatc    1020
gttggaggca aacgggctca gctggggac ttgccgtggc aggtggccat caaagatgcc    1080
tccggaatca cctgtggtgg catctacatc ggcggctgct ggatcctgac cgccgcccac    1140
tgccttcggg ccagcaagac tcaccgctac cagatctgga ccaccgtggt ggattggatt    1200
caccccgacc tgaagaggat tgtcattgag tatgtcgacc gcatcatctt ccatgaaaac    1260
tacaatgccg ggacgtatca gaacgacatc gccctcatcg agatgaagaa ggatgggaac    1320
aagaaggact gtgagctgcc tcgctccatc cccgcctgtg taccatggtc tccgtacctg    1380
ttccagccaa atgacacatg catcgtgagc ggctgggggcc gcgagaaaga caacgagagg    1440
gtcttctccc tgcagtgggg tgaagtcaag ctgatcagca actgctccaa gttctacggc    1500
aaccgcttct atgagaagga gatggagtgc ccggcacct atgacggcag cattgacgcg    1560
tgcaagggag acagtggggg cccctggtc tgcatggacg ccaacaatgt gacctacgtg    1620
tggggagttg tgtcctgggg cgagaactgt ggcaagcctg agttcccggg cgtgtacaca    1680
aaggtggcaa actattttga ctggatctcc tatcacgttg caggcccctt catttcacag    1740
tacaacgtat aa    1752
```

<210> SEQ ID NO 11
<211> LENGTH: 449
<212> TYPE: PRT
<213> ORGANISM: Artificial Sequence
<220> FEATURE:
<223> OTHER INFORMATION: sequence of Complement Factor H-like Protein 1
     (FHL1)

<400> SEQUENCE: 11

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
```

```
            100             105             110

Thr Cys Asn Glu Gly Tyr Gln Leu Leu Gly Glu Ile Asn Tyr Arg Glu
        115             120             125

Cys Asp Thr Asp Gly Trp Thr Asn Asp Ile Pro Ile Cys Glu Val Val
    130             135             140

Lys Cys Leu Pro Val Thr Ala Pro Glu Asn Gly Lys Ile Val Ser Ser
145             150             155             160

Ala Met Glu Pro Asp Arg Glu Tyr His Phe Gly Gln Ala Val Arg Phe
            165             170             175

Val Cys Asn Ser Gly Tyr Lys Ile Glu Gly Asp Glu Glu Met His Cys
            180             185             190

Ser Asp Asp Gly Phe Trp Ser Lys Glu Lys Pro Lys Cys Val Glu Ile
        195             200             205

Ser Cys Lys Ser Pro Asp Val Ile Asn Gly Ser Pro Ile Ser Gln Lys
        210             215             220

Ile Ile Tyr Lys Glu Asn Glu Arg Phe Gln Tyr Lys Cys Asn Met Gly
225             230             235             240

Tyr Glu Tyr Ser Glu Arg Gly Asp Ala Val Cys Thr Glu Ser Gly Trp
            245             250             255

Arg Pro Leu Pro Ser Cys Glu Glu Lys Ser Cys Asp Asn Pro Tyr Ile
            260             265             270

Pro Asn Gly Asp Tyr Ser Pro Leu Arg Ile Lys His Arg Thr Gly Asp
            275             280             285

Glu Ile Thr Tyr Gln Cys Arg Asn Gly Phe Tyr Pro Ala Thr Arg Gly
        290             295             300

Asn Thr Ala Lys Cys Thr Ser Thr Gly Trp Ile Pro Ala Pro Arg Cys
305             310             315             320

Thr Leu Lys Pro Cys Asp Tyr Pro Asp Ile Lys His Gly Gly Leu Tyr
            325             330             335

His Glu Asn Met Arg Arg Pro Tyr Phe Pro Val Ala Val Gly Lys Tyr
            340             345             350

Tyr Ser Tyr Tyr Cys Asp Glu His Phe Glu Thr Pro Ser Gly Ser Tyr
        355             360             365

Trp Asp His Ile His Cys Thr Gln Asp Gly Trp Ser Pro Ala Val Pro
    370             375             380

Cys Leu Arg Lys Cys Tyr Phe Pro Tyr Leu Glu Asn Gly Tyr Asn Gln
385             390             395             400

Asn Tyr Gly Arg Lys Phe Val Gln Gly Lys Ser Ile Asp Val Ala Cys
            405             410             415

His Pro Gly Tyr Ala Leu Pro Lys Ala Gln Thr Thr Val Thr Cys Met
            420             425             430

Glu Asn Gly Trp Ser Pro Thr Pro Arg Cys Ile Arg Val Ser Phe Thr
            435             440             445

Leu
```

```
<210> SEQ ID NO 12
<211> LENGTH: 1350
<212> TYPE: DNA
<213> ORGANISM: Artificial Sequence
<220> FEATURE:
<223> OTHER INFORMATION: nucleotide sequence encoding FHL1

<400> SEQUENCE: 12
atgcgcctcc tggccaagat catctgcctc atgctgtggg ccatctgcgt ggctgaggac        60
```

```
tgcaatgagc tgccgcccag gaggaacaca gagatcctga cagggagctg gtctgaccag     120
acctaccctg agggcaccca ggcgatctac aagtgccggc cgggctacag gagcctgggg     180
aacatcatca tggtgtgtag aaagggcgaa tgggtggccc tcaacccct gaggaagtgc      240 cagaagcggc cctgtggcca ccccgggggac acacccttcg ggaccttcac cctgaccggc     300
ggcaatgtgt ttgagtacgg cgtgaaggct gtctacacat gcaacgaggg gtaccagctg     360
ctgggcgaga ttaactaccg ggagtgtgac accgatgggt ggaccaacga cattcccatc     420
tgtgaggtgg tcaagtgtct ccccgtgaca gccccagaaa atggcaaaat cgtgagcagc     480
gccatggagc ctgaccgcga atatcacttt gggcaggccg tgaggtttgt gtgcaactcg     540
ggctacaaaa ttgaaggtga tgaggagatg cactgcagcg atgatggctt ctggtccaag     600
gagaagccca aatgtgtgga gatctcctgc aagtctcccg acgtgatcaa cggcagccca     660
atcagccaga agattattta caaagagaac gagcgcttcc agtacaagtg taacatgggc     720
tatgagtatt cagagagggg agatgccgtc tgcactgaga gcggctggag accactgcct     780
agctgcgagg aaaagagttg tgacaaccct tacatcccaa atggcgacta ctcccctctg     840
cggatcaaac accggaccgg ggatgaaatc acctatcagt gccgcaatgg attctacccg     900
gccacccgcg gcaacaccgc caaatgcacc agcacaggct ggatccccgc cccccgctgt     960
acgctgaagc cttgcgacta tccagacatc aagcacggag gcctgtacca cgaaaacatg    1020
cggcggcctt atttccctgt ggcagtgggg aagtactaca gctactactg cgacgagcac    1080
ttcgagaccc cctctggctc ctactgggac cacatccact gcacacagga cggctggtct    1140
ccagctgtgc cctgcctgag gaaatgctac ttcccctacc tggagaacgg atacaaccag    1200
aactatggcc gcaagttcgt gcagggcaag agcatcgatg tggcctgcca ccctggctac    1260
gccctgccca aggcccagac aactgtgacc tgcatggaga atggttggag ccccacccccg    1320 cgctgcatcc gggtgtcctt cacgctctga                                     1350

<210> SEQ ID NO 13
<211> LENGTH: 585
<212> TYPE: DNA
<213> ORGANISM: Artificial Sequence
<220> FEATURE:
<223> OTHER INFORMATION: example CMV (cytomegalovirus) promoter sequence

<400> SEQUENCE: 13
ggagttccgc gttacataac ttacggtaaa tggcccgcct ggctgaccgc ccaacgaccc       60
ccgcccattg acgtcaataa tgacgtatgt tcccatagta acgccaatag ggactttcca     120
ttgacgtcaa tgggtggagt atttacggta aactgcccac ttggcagtac atcaagtgta     180
tcatatgcca agtacgcccc ctattgacgt caatgacggt aaatggcccg cctggcatta     240
tgcccagtac atgaccttat gggactttcc tacttggcag tacatctacg tattagtcat     300
cgctattacc atggtgatgc ggttttggca gtacatcaat gggcgtggat agcggtttga     360
ctcacgggga tttccaagtc tccaccccat tgacgtcaat gggagtttgt tttggcacca     420
aaatcaacgg gactttccaa aatgtcgtaa caactccgcc ccattgacgc aaatgggcgg     480
taggcgtgta cggtgggagg tctatataag cagagctcgt ttagtgaacc gtcagatcgc     540
ctggagacgc catccacgct gttttgacct ccatagaaga caccg                   585

<210> SEQ ID NO 14
<211> LENGTH: 223
<212> TYPE: DNA
<213> ORGANISM: Artificial Sequence
```

```
<220> FEATURE:
<223> OTHER INFORMATION: Bovine Growth Hormone poly-A (bGH poly-A)
     signal sequence

<400> SEQUENCE: 14
gtgccttcta gttgccagcc atctgttgtt tgcccctccc ccgtgccttc cttgaccctg      60
gaaggtgcca ctcccactgt cctttcctaa taaaatgagg aaattgcatc gcattgtctg     120
agtaggtgtc attctattct ggggggtggg gtggggcagg acagcaaggg ggaggattgg     180
gaagacaata gcaggcatgc tggggatgcg gtgggctcta tgg                       223

<210> SEQ ID NO 15
<211> LENGTH: 245
<212> TYPE: DNA
<213> ORGANISM: Artificial Sequence
<220> FEATURE:
<223> OTHER INFORMATION: WPRE3 sequence (shortened version of WPRE,
     contains only minimal gamma and alpha elements)

<400> SEQUENCE: 15
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttag ttcttgccac ggcggaactc     180
atcgccgcct gccttgcccg ctgctggaca ggggctcggc tgttgggcac tgacaattcc     240
gtggt                                                                 245

<210> SEQ ID NO 16
<211> LENGTH: 1752
<212> TYPE: DNA
<213> ORGANISM: Artificial Sequence
<220> FEATURE:
<223> OTHER INFORMATION: GT005: CFI wild type sequence

<400> SEQUENCE: 16
atgaagcttc ttcatgtttt cctgttattt ctgtgcttcc acttaaggtt ttgcaaggtc      60
acttatacat ctcaagagga tctggtggag aaaaagtgct tagcaaaaaa atatactcac     120
ctctcctgcg ataaagtctt ctgccagcca tggcagagat gcattgaggg cacctgtgtt     180
tgtaaactac cgtatcagtg cccaaagaat ggcactgcag tgtgtgcaac taacaggaga     240
agcttcccaa catactgtca acaaaagagt ttggaatgtc ttcatccagg acaaagtttt     300
ttaaataacg gaacatgcac agccgaagga aagtttagtg tttccttgaa gcatggaaat     360
acagattcag agggaatagt tgaagtaaaa cttgtggacc aagataagac aatgttcata     420
tgcaaaagca gctggagcat gagggaagcc aacgtggcct gccttgacct tgggtttcaa     480
caaggtgctg atactcaaag aaggtttaag ttgtctgatc tctctataaa ttccactgaa     540
tgtctacatg tgcattgccg aggattagag accagtttgg ctgaatgtac ttttactaag     600
agaagaacta tgggttacca ggatttcgct gatgtggttt gttatacaca gaaagcagat     660
tctccaatgg atgacttctt tcagtgtgtg aatgggaaat acatttctca gatgaaagcc     720
tgtgatggta tcaatgattg tggagaccaa agtgatgaac tgtgttgtaa agcatgccaa     780
ggcaaaggct tccattgcaa atcgggtgtt tgcattccaa gccagtatca atgcaatggt     840
gaggtggact gcattacagg ggaagatgaa gttggctgtg caggctttgc atctgtggct     900
caagaagaaa cagaaatttt gactgctgac atggatgcag aaagaagacg gataaaatca     960
ttattaccta aactatcttg tggagttaaa aacagaatgc acattcgaag gaaacgaatt    1020
```

```
gtgggaggaa agcgagcaca actgggagac ctcccatggc aggtggcaat taaggatgcc    1080
agtggaatca cctgtggggg aatttatatt ggtggctgtt ggattctgac tgctgcacat    1140
tgtctcagag ccagtaaaac tcatcgttac caaatatgga caacagtagt agactggata    1200 cacccgacc ttaaacgtat agtaattgaa tacgtggata gaattatttt ccatgaaaac    1260
tacaatgcag gcacttacca aaatgacatc gctttgattg aaatgaaaaa agacggaaac    1320
aaaaaagatt gtgagctgcc tcgttccatc cctgcctgtg tccctggtc tccttaccta    1380 ttccaaccta atgatacatg catcgtttct ggctggggac gagaaaaaga taacgaaaga    1440
gtcttttcac ttcagtgggg tgaagttaaa ctaataagca actgctctaa gttttacgga    1500
aatcgtttct atgaaaaaga aatggaatgt gcaggtacat atgatggttc catcgatgcc    1560
tgtaaagggg actctggagg cccccttagtc tgtatggatg ccaacaatgt gacttatgtc    1620
tggggtgttg tgagttgggg ggaaaactgt ggaaaaccag agttcccagg tgtttacacc    1680
aaagtggcca attattttga ctggattagc taccatgtag gaaggccttt tatttctcag    1740
tacaatgtat aa                                                        1752
```

```
<210> SEQ ID NO 17
<211> LENGTH: 1350
<212> TYPE: DNA
<213> ORGANISM: Artificial Sequence
<220> FEATURE:
<223> OTHER INFORMATION: RC001: FHL-1 wild type sequence

<400> SEQUENCE: 17
```

```
atgagacttc tagcaaagat tatttgcctt atgttatggg ctatttgtgt agcagaagat      60
tgcaatgaac ttcctccaag aagaaataca gaaattctga caggttcctg gtctgaccaa     120
acatatccag aaggcaccca ggctatctat aaatgccgcc ctggatatag atctcttgga     180
aatataataa tggtatgcag gaagggagaa tggggttgctc ttaatccatt aaggaaatgt     240
cagaaaaggc cctgtggaca tcctggagat actcctttg gtactttac ccttacagga       300 ggaaatgtgt ttgaatatgg tgtaaaagct gtgtatacat gtaatgaggg gtatcaattg      360
ctaggtgaga ttaattaccg tgaatgtgac acagatggat ggaccaatga tattcctata     420
tgtgaagttg tgaagtgttt accagtgaca gcaccagaga atggaaaaat tgtcagtagt      480
gcaatggaac cagatcggga ataccatttt ggacaagcag tacggtttgt atgtaactca     540
ggctacaaga ttgaaggaga tgaagaaatg cattgttcag acgatggttt ttggagtaaa      600
gagaaaccaa agtgtgtgga aatttcatgc aaatccccag atgttataaa tggatctcct       660
atatctcaga agattatttta taaggagaat gaacgatttc aatataaatg taacatgggt      720
tatgaataca gtgaaagagg agatgctgta tgcactgaat ctggatggcg tccgttgcct       780
tcatgtgaag aaaaatcatg tgataatcct tatattccaa atggtgacta ctcacctta       840 aggattaaac acagaactgg agatgaaatc acgtaccagt gtagaaatgg tttttatcct       900
gcaacccggg gaaatacagc aaaatgcaca agtactggct ggatacctgc tccgagatgt       960
accttgaaac cttgtgatta tccagacatt aaacatggag gtctatatca tgagaatatg      1020
cgtagaccat actttccagt agctgtagga aaatattact cctattactg tgatgaacat     1080
tttgagactc cgtcaggaag ttactgggat cacattcatt gcacacaaga tggatggtcg     1140
ccagcagtac catgcctcag aaaatgttat tttccttatt tggaaaatgg atataatcaa     1200
aattatggaa gaaagtttgt acagggtaaa tctatagacg ttgcctgcca tcctggctac     1260
gctcttccaa aagcgcagac cacagttaca tgtatggaga atggctggtc tcctactccc     1320
```

-continued

```
agatgcatcc gtgtcagctt taccctctga                                1350

<210> SEQ ID NO 18
<211> LENGTH: 1752
<212> TYPE: DNA
<213> ORGANISM: Artificial Sequence
<220> FEATURE:
<223> OTHER INFORMATION: RC128: CFI GeneArt - Basic

<400> SEQUENCE: 18
atgaagctgc tgcatgtgtt tctgctgttc ctctgcttcc acctgaggtt ctgcaaagtg    60
acctacacca gccaagagga cctggtggaa aagaagtgcc tggccaagaa gtacacccac   120
ctgagctgcg acaaggtgtt ctgccagcct tggcagagat gcatcgaggg cacctgtgtg   180
tgcaagctgc cctatcagtg ccccaagaat ggcacagccg tgtgcgccac caacagaaga   240
agcttcccta cctactgcca gcagaaaagc ctggaatgtc tgcaccccgg caccaagttt   300
ctgaacaacg gcacctgtac cgccgagggc aagtttagcg tgtccctgaa gcacggcaac   360
accgactctg agggcatcgt ggaagtgaag ctggtggacc aggacaagac catgttcatc   420
tgcaagagca gctggtccat cgcgcgaggcc aatgtggctt gtctggatct gggattccag   480
cagggcgccg acacacagag aagattcaag ctgagcgacc tgagcatcaa cagcaccgag   540
tgcctgcatg tgcactgtag aggcctggaa acaagcctgg ccgagtgcac cttcaccaag   600
agaaggacca tgggctacca ggacttcgcc gacgtcgtgt gctacaccca gaaagccgac   660
tctcccatgg acgatttctt ccagtgcgtg aacggcaagt acatcagcca gatgaaggcc   720
tgcgacggca tcaacgattg cggcgatcag agcgacgagc tgtgctgcaa agcctgtcaa   780
ggcaagggct tccactgcaa gtccggcgtg tgtatcccta gccagtacca gtgcaatggc   840
gaggtggact gtatcaccgg cgaggatgaa gtgggctgtg ccggatttgc cagcgtggcc   900
caagaggaaa ccgagatcct gaccgccgat atggacgccg agcggcggag aatcaaaagc   960
ctgctgccta agctgtcctg cggcgtgaag aaccggatgc acatccggcg caagagaatc  1020
gtcggaggca aaagagcaca gctgggcgat ctgccttggc aagtggccat caaggatgcc  1080
agcggcatca catgtggcgg catctacatc ggcggctgct ggattctgac agccgctcat  1140
tgtctgcggg ccagcaagac ccaccggtat cagatctgga ccaccgtggt ggactggatt  1200 cacccccgacc tgaagcggat cgtgatcgag tacgtggacc ggatcatctt ccacgagaac  1260
tacaacgccg gcacctacca gaacgatatc gccctgatcg agatgaagaa ggacgggaac  1320
aagaaggact gcgagctgcc tagatctatc cccgcctgtg ttccttggag cccctacctg  1380
ttccagccta acgatacctg catcgtgtcc ggctggggca gagagaagga taacgagagg  1440
gtgttcagcc tgcagtgggg cgaagtgaaa ctgatcagca actgcagcaa gttctacggc  1500
aaccggttct acgagaaaga aatggaatgc gccggcacat acgacggctc catcgatgcc  1560
tgtaaaggcg attctggcgg ccctctcgtg tgcatggatg ccaacaatgt gacctacgtg  1620
tggggcgtcg tgtcctgggg agagaattgt ggcaagcctg agttccccgg cgtgtacacc  1680
aaggtggcca actacttcga ctggatcagc taccacgtgg cagacccctt tatcagccag  1740
tacaacgtgt ga                                                   1752

<210> SEQ ID NO 19
<211> LENGTH: 1752
<212> TYPE: DNA
<213> ORGANISM: Artificial Sequence
<220> FEATURE:
```

-continued

<223> OTHER INFORMATION: RC129: CFI GeneArt - Manually optimised

<400> SEQUENCE: 19

```
atgaagctgc tccatgtgtt tctgctcttc ctctgcttcc acctgaggtt ctgcaaagtg      60
acctacacca gccaagagga cctggtggaa aagaaatgcc tggccaagaa atacacccac     120
ctgagctgcg acaaggtgtt ctgccagcct tggcagagat gcatcgaggg cacctgtgtg     180
tgcaagctgc cctatcagtg ccccaagaat ggcacagccg tgtgcgctac aaacagaagg     240
agcttcccta cctactgcca gcaaaaaagc ctggagtgcc tgcaccccgg caccaagttt     300
ctgaacaatg gcacctgtac cgccgagggc aagtttagcg tgtccctgaa gcacggcaac     360
accgactctg agggcatcgt ggaagtgaag ctggtggacc aggacaagac catgttcatc     420
tgcaagagct cctggtccat gcgcgaggcc aatgtggctt gtctggatct gggattccag     480
caaggcgccg acacacagag aaggttcaag ctgagcgacc tgagcatcaa cagcaccgag     540
tgcctgcatg tgcactgtag aggcctggaa acaagcctgg ccgagtgcac cttcaccaag     600
agaaggacca tgggctacca ggacttcgcc gacgtcgtgt gctacaccca gaaagccgac     660
tctcccatgg acgatttctt tcagtgcgtg aacggcaagt acatcagcca gatgaaggcc     720
tgcgacggca tcaacgattg cggcgatcag agcgacgagc tgtgctgtaa agcctgtcaa     780
ggcaagggct ccactgcaa gtccggcgtg tgtatcccta gccagtacca gtgcaatggc     840
gaggtggact gtatcaccgg cgaggatgaa gtgggctgtg ccggatttgc cagcgtggcc     900
caagaggaaa ccgagatcct gaccgccgat atggacgccg agcggaggag aatcaaaagc     960
ctgctcccta agctgtcctg cggcgtgaag aaccggatgc acatccggcg caagagaatc    1020
gtcggaggca aaagagcaca gctgggcgat ctgccttggc aagtggccat caaggatgcc    1080
agcggcatca catgtggcgg gatctacatc ggcggatgct ggattctgac agccgctcat    1140
tgtctgcggg ccagcaagac ccaccggtat cagatctgga ccacagtggt cgactggatt    1200 cacccgacc tgaagcggat cgtgatcgag tacgtggacc ggatcatttt ccacgagaac    1260
tacaacgccg gcacctacca gaacgatatc gccctgatcg agatgaaaaa ggacgggaac    1320
aagaaagact gcgagctgcc tagatctatc cccgcctgtg ttccttggag ccccctacctg    1380 ttccagccta acgatacctg catcgtgtcc ggctggggca gagagaagga taacgagagg    1440
gtgttcagcc tgcagtgggg cgaagtgaaa ctgatcagca actgcagcaa gttctacggc    1500
aaccggttct acgagaaaga aatggaatgc gccggcacat acgacggctc catcgatgcc    1560
tgtaaaggcg attctggcgg acctctcgtg tgcatggatg ccaacaatgt gacctacgtg    1620
tggggcgtcg tgtcctgggg agagaattgt ggcaagcctg agttccccgg cgtgtacacc    1680
aaggtggcca actacttcga ctggatcagc taccacgtgg cagacccctt tatcagccag    1740
tacaacgtgt ga                                                       1752
```

```
<210> SEQ ID NO 20
<211> LENGTH: 1752
<212> TYPE: DNA
<213> ORGANISM: Artificial Sequence
<220> FEATURE:
<223> OTHER INFORMATION: RC130: CFI Genscript - Basic
```

<400> SEQUENCE: 20

```
atgaagctgc tgcatgtctt tctgctgttt ctgtgcttcc atctgaggtt ctgcaaggtc      60
acttacacta gccaggagga tctggtcgag aagaagtgtc tggccaagaa gtacacacac     120
ctgagctgcg acaaggtgtt ctgtcagcct tggcagcggt gcatcgaggg cacctgcgtg     180
```

-continued

```
tgcaagctgc cttaccagtg cccaaagaac ggcaccgccg tgtgcgccac aaatcggaga      240
tcttttccaa catattgcca gcagaagagc ctggagtgtc tgcaccccgg caccaagttc      300
ctgaacaatg gcacctgcac agccgagggc aagttttctg tgagcctgaa gcacggcaac      360
acagatagcg agggcatcgt ggaggtgaag ctggtggacc aggataagac catgttcatc      420
tgtaagagca gctggtccat gagggaggca aacgtggcat gcctggatct gggattccag      480 caggagcag acacacagag gcgctttaag ctgtccgacc tgtctatcaa tagcaccgag       540
tgcctgcacg tgcactgtag gggcctggag acatccctgg cagagtgcac cttcacaaag      600
cggagaacaa tgggctacca ggactttgcc gacgtggtgt gctatacca gaaggccgat       660 agccctatgg acgatttctt tcagtgcgtg aacggcaagt atatctccca gatgaaggcc      720
tgcgacggca tcaatgactg tggcgatcag tctgacgagc tgtgctgtaa ggcctgtcag      780
ggcaagggct tccactgcaa gagcggcgtg tgcatccctt cccagtacca gtgcaacggc      840
gaggtggatt gtatcacagg agaggacgaa gtgggatgcg caggatttgc atctgtggca      900
caggaggaga cagagatcct gacagccgac atggatgccg agaggcgccg gatcaagtct      960
ctgctgccta agctgagctg tggcgtgaag aatcggatgc acatcagaag gaagcgcatc     1020
gtgggaggca agcgggccca gctgggcgat ctgccctggc aggtggccat caaggacgcc     1080
tctggcatca cctgcggcgg catctacatc ggcggctgtt ggattctgac cgcagcacac     1140
tgcctgagag caagcaagac acacaggtat cagatctgga ccacagtggt ggattggatt     1200
cacccagacc tgaagagaat cgtgatcgag tacgtggata ggatcatctt ccacgagaac     1260
tacaatgccg gcacatatca gaacgacatc gccctgatcg agatgaagaa ggatggcaat     1320
aagaaggact gtgagctgcc cagatccatc cctgcatgcg tgccctggag cccctatctg     1380
ttccagccca acgatacctg catcgtgtcc ggatggggaa gggagaagga caatgagcgg     1440 gtgtttctc tgcagtgggg cgaggtgaag ctgatctcca actgttctaa gttctacggc     1500
aataggtttt atgagaagga gatggagtgc gccggcacct acgatggcag catcgacgcc     1560
tgtaagggcg attccggagg accactggtg tgcatggacg caaacaatgt gacatacgtg     1620
tggggagtgg tgtcctgggg agagaactgc ggcaagccag agtttcccgg cgtgtatacc     1680
aaggtggcca attattttga ttggatttca taccatgtcg ggagaccatt cattagtcag     1740
tacaacgtgt ga                                                        1752
```

```
<210> SEQ ID NO 21
<211> LENGTH: 1752
<212> TYPE: DNA
<213> ORGANISM: Artificial Sequence
<220> FEATURE:
<223> OTHER INFORMATION: RC131: CFI Genscript - Manually optimised

<400> SEQUENCE: 21
```

```
atgaagctgc tccatgtctt tctgctcttt ctgtgcttcc atctgaggtt ctgcaaggtc       60
acttacacta gccaggagga tctggtcgag aagaaatgtc tggccaagaa atacacacac      120
ctgagctgcg acaaggtgtt ctgtcagcct tggcagcggt gcatcgaggg cacctgcgtg      180
tgcaagctgc cttaccagtg cccaaagaac ggcaccgccg tgtgcgccac aaatcggaga      240
tcttttccaa catattgcca gcaaaagagc ctggagtgtc tgcaccccgg caccaagttc      300
ctgaacaatg gcacctgcac agccgagggc aagttttctg tgagcctgaa gcacggcaac      360
acagatagcg agggcatcgt ggaggtgaag ctggtggacc aggataagac catgttcatc      420
```

-continued

```
tgtaagagct cctggtccat gagggaggca aacgtggcat gcctggatct gggattccag      480
caaggagcag acacacagag gcgctttaag ctgtccgatc tgagtatcaa tagcaccgag      540
tgcctgcacg tgcactgtag gggcctggag acatccctgg cagagtgcac cttcacaaag      600
cggagaacaa tgggctacca ggactttgcc gacgtggtct gctataccca gaaggccgat      660
agccctatgg acgatttctt tcagtgcgtg aacggcaagt atatctccca gatgaaggcc      720
tgcgacggca tcaatgactg tggcgatcag tctgacgagc tgtgctgtaa ggcctgtcag      780
ggcaagggct tccactgcaa gagcggcgtg tgcatccctt cccagtacca gtgcaacggc      840
gaggtggatt gtatcacagg agaggacgaa gtgggatgcg caggatttgc atctgtggca      900
caggaggaaa cagagatcct gacagccgac atggatgccg agaggcgccg gatcaagtct      960
ctgctcccta agctgagctg tggcgtgaag aatcggatgc acatcagaag gaagcgcatc     1020
gtgggaggca agcgggccca gctgggcgat ctgccctggc aggtggccat caaggacgcc     1080
tctggcatca cctgcggcgg gatctacatc ggcggatgtt ggattctgac cgcagcccac     1140
tgcctgagag caagcaagac acacagatat cagatctgga ccacagtggt cgattggatt     1200
cacccagacc tgaagagaat cgtgatcgag tacgtggata ggatcatttt ccacgagaat     1260
tacaatgctg gcacatatca gaatgatatc gctctcatcg agatgaagaa agatggcaat     1320
aagaaagact gtgagctgcc cagatccatc cctgcatgcg tgccctggag cccctatctg     1380
ttccagccca acgatacctg catcgtgtcc ggatggggaa gggagaagga caatgagcgg     1440 gtgtttctc tgcagtgggg cgaggtgaag ctgatctcca actgttctaa gttctacggc     1500
aataggtttt atgagaagga gatggagtgc gccggcacct acgatggcag catcgacgcc     1560
tgtaagggcg attccggagg cccactggtg tgcatggacg caaacaatgt gacatacgtg     1620
tggggagtgg tctcctgggg agagaactgc ggcaagccag agtttcccgg cgtgtatacc     1680
aaggtggcca attattttga ttggatttca taccatgtcg ggagaccatt cattagtcaa     1740
tacaacgttt ga                                                        1752
```

```
<210> SEQ ID NO 22
<211> LENGTH: 1752
<212> TYPE: DNA
<213> ORGANISM: Artificial Sequence
<220> FEATURE:
<223> OTHER INFORMATION: RC132: CFI IDT - Basic

<400> SEQUENCE: 22
```

```
atgaagctcc tccacgtctt cttgttgttt ctctgtttcc acctgagatt ttgcaaagta       60
acttacacca gtcaagaaga cttggtcgag aagaagtgtc tcgccaaaaa gtatactcac      120
ctgagctgtg ataaagtgtt ctgtcagccg tggcagcgct gcattgaggg tacatgtgtc      180
tgtaaactgc cttatcagtg tccgaagaac ggtacggctg tctgtgctac taacagacgg      240
tcttttccta cttattgcca gcagaagagt ttggaatgtc tccaccctgg taccaagttt      300
ctcaacaatg gcacctgtac tgctgaaggt aaattctccg tcagtctcaa gcatggtaac      360
actgacagtg aagggatagt agaggtaaag ttggttgacc aggacaagac gatgttcata      420
tgcaagtcaa gctggtccat gcgcgaggcg aatgtcgctt gtcttgattt gggcttccag      480
caaggggcag acacacagag aagattcaaa ttgagcgacc tgagtataaa ttcaaccgag      540
tgcctccatg tacattgcag agggctcgag acttcacttg ccgaatgtac atttacgaag      600
aggcggacta tgggatatca ggactttgcc gacgtagtat gttatactca gaaagcagac      660
agtcctatgg atgactttt ccaatgcgtc aacggcaaat acatcagtca aatgaaagcg      720
```

-continued

```
tgcgacggta tcaacgattg tggtgaccag tctgatgagc tttgctgtaa agcatgtcaa    780
ggaaaggggt tccattgcaa gagtggtgta tgtattccct cacaatatca gtgcaatggg    840
gaagtcgatt gcataacagg tgaggatgag gtgggctgcg cgggatttgc ttctgtggcg    900
caagaggaga ctgagatcct tacagcggat atggacgccg aacgaagacg catcaaatct    960
ctccttccca aactttcatg cggcgtcaaa aaccgaatgc atatacgcag gaagagaatt    1020
gttgggggaa agcgggcaca gctgggcgac ctcccctggc aagttgcaat aaaggatgca    1080
agtgggataa cgtgcggggg catctacatc ggggggtgct ggatcttgac tgccgcccac    1140
tgtcttagag cctctaagac ccataggtac caaatctgga caactgtagt tgactggata    1200
catccggacc ttaaacgcat agttattgaa tacgttgacc gcataatatt tcatgagaat    1260
tataacgcgg gtacctatca gaatgacatc gccctcatcg agatgaaaaa agacgggaat    1320
aaaaaggact gcgagctgcc gcgctctata cctgcgtgtg tcccctggag tccttatctt    1380
ttccaaccta acgatacgtg tatagtgagc ggctggggcc gggagaagga caatgaacga    1440
gttttttcct tgcaatgggg agaagtgaag cttatttcca attgttcaaa gtttttatgga    1500 aatagatttt atgaaaaaga aatggagtgt gcgggcactt atgacgggtc aattgatgct    1560
tgcaaaggtg atagcggggg cccacttgtc tgcatggacg ctaacaacgt gacttatgtg    1620
tggggtgttg tgtcctgggg cgaaaactgt ggcaagcccg agtttcccgg cgtatacacc    1680
aaagtagcta attatttcga ctggattagt tatcatgttg ggcggccatt tatatcccag    1740
tataatgtct aa                                                      1752
```

<210> SEQ ID NO 23
<211> LENGTH: 1752
<212> TYPE: DNA
<213> ORGANISM: Artificial Sequence
<220> FEATURE:
<223> OTHER INFORMATION: RC133: CFI IDT - Manually optimised

<400> SEQUENCE: 23

```
atgaagctcc tgcacgtctt cttgctgttt ctctgtttcc acctgagatt ttgcaaagta     60
acttacacca gtcaagaaga cttggtcgag aagaaatgtc tcgccaaaaa gtatactcac    120
ctgagctgtg ataaagtgtt ctgtcagccg tggcagcgct gcattgaggg tacatgtgtc    180
tgtaaactgc cttatcagtg tccgaagaac ggcacggctg tctgtgctac taacagacgg    240
tcttttccta cttattgcca gcaaaagagt ttggaatgtc tccaccctgg taccaagttt    300
ctcaacaatg gcacctgtac tgctgaaggc aaattctccg tcagtctcaa gcatggtaac    360
actgattctg aagggatagt agaagtaaag ttggttgacc aggacaagac gatgttcata    420
tgcaagtcaa gctggtccat gcgcgaggcg aatgtcgctt gtcttgattt gggcttccag    480
caaggggcag acacacagag aagattcaaa ttgagcgacc tgagtataaa ttcaaccgag    540
tgcctccatg tacattgcag agggctcgag acttctcttg ctgagtgtac atttacgaag    600
aggcggacta tgggatatca ggactttgct gacgtagtgt gttatactca gaaagcagac    660
agtcctatgg atgactttt ccaatgcgtc aacggcaaat acatcagtca aatgaaagcg    720
tgcgacggta tcaacgattg tggtgaccag tctgatgagc tttgctgtaa agcatgtcaa    780
ggaaaggggt tccattgcaa gagtggtgta tgtattccct cacaatatca gtgcaatggg    840
gaagtcgatt gcataacagg cgaggatgag gtgggctgcg cgggatttgc ttctgtggcg    900
caagaggaaa ctgagatcct tacagcggat atggacgccg aacgaagacg catcaaatct    960
```

-continued

```
ctccttccca aactttcatg cggcgtcaaa aaccgaatgc atatacgcag gaagagaatt      1020
gttgggggaa agcgggcaca gctgggcgac ctccccctggc aagttgcaat aaaggatgca      1080
agtgggataa cgtgcggggg catctacatc gggggctgct ggatcttgac tgccgctcac      1140
tgtcttagag cctctaagac ccatagatac caaatctgga caactgtagt tgactggata      1200
catccggacc ttaaacgcat agttattgaa tacgttgacc gcataatctt tcatgagaat      1260
tataacgcgg gcacatacca aaatgacatc gccctgatcg agatgaaaaa ggacgggaat      1320
aaaaaggact gcgagctgcc gcgctctata cctgcgtgtg tcccctggag tccttatctt      1380
ttccaaccta acgatacgtg tatagtgagc ggctgggggcc gggagaagga caatgaacga      1440
gttttttcct tgcaatgggg agaagtgaag cttatttcca attgttcaaa gttttatgga      1500
aatagatttt atgaaaaaga aatggagtgt gcgggcactt atgacgggtc aattgatgct      1560
tgcaaaggtg atagcggggg cccacttgtc tgcatggacg ctaacaatgt gacttatgtg      1620
tggggtgttg tgtcctgggg cgaaaactgt ggcaagcccg agtttcccgg cgtatacacc      1680
aaagtagcta attatttcga ctggattagt tatcatgttg ggcggccatt tatatcccag      1740
tataatgtct aa                                                         1752
```

<210> SEQ ID NO 24
<211> LENGTH: 1752
<212> TYPE: DNA
<213> ORGANISM: Artificial Sequence
<220> FEATURE:
<223> OTHER INFORMATION: RC134: CFI JCat - Basic

<400> SEQUENCE: 24

```
atgaagctgc tgcacgtgtt cctgctgttc ctgtgcttcc acctgcgctt ctgcaaggtg        60
acctacacca gccaggagga cctggtggag aagaagtgcc tggccaagaa gtacacccac       120
ctgagctgcg acaaggtgtt ctgccagccc tggcagcgct gcatcgaggg cacctgcgtg       180
tgcaagctgc cctaccagtg ccccaagaac ggcaccgccg tgcgccacca caaccgccgc       240
agcttcccca cctactgcca gcagaagagc ctggagtgcc tgcaccccgg caccaagttc       300
ctgaacaacg gcacctgcac cgccgagggc aagttcagcg tgagcctgaa gcacggcaac       360
accgacagcg agggcatcgt ggaggtgaag ctggtggacc aggacaagac catgttcatc       420
tgcaagagca gctggagcat cgcgcgaggcc aacgtggcct gcctggacct gggcttccag       480
cagggcgccg acacccagcg ccgcttcaag ctgagcgacc tgagcatcaa cagcaccgag       540
tgcctgcacg tgcactgccg cggcctggag accagcctgg ccgagtgcac cttcaccaag       600
cgccgcacca tgggctacca ggacttcgcc gacgtggtgt gctacaccca gaaggccgac       660
agccccatgg acgacttctt ccagtgcgtg aacggcaagt acatcagcca gatgaaggcc       720
tgcgacggca tcaacgactg cggcgaccag agcgacgagc tgtgctgcaa ggcctgccag       780
ggcaagggct ccactgcaa gagcggcgtg tgcatcccca gccagtacca gtgcaacggc       840
gaggtggact gcatcaccgg cgaggacgag gtgggctgcg ccggcttcgc cagcgtggcc       900
caggaggaga ccgagatcct gaccgccgac atggacgccg agcgccgccg catcaagagc       960
ctgctgccca agctgagctg cggcgtgaag aaccgcatgc acatccgccg caagcgcatc      1020
gtgggcggca agcgcgccca gctgggcgac ctgccctggc aggtggccat caaggacgcc      1080
agcggcatca cctgcggcgg catctacatc ggcggctgct ggatcctgac cgccgcccac      1140
tgcctgcgcg ccagcaagac ccaccgctac cagatctgga ccaccgtggt ggactggatc      1200
caccccgacc tgaagcgcat cgtgatcgag tacgtggacc gcatcatctt ccacgagaac      1260
```

-continued

```
tacaacgccg gcacctacca gaacgacatc gccctgatcg agatgaagaa ggacggcaac      1320
aagaaggact gcgagctgcc ccgcagcatc cccgcctgcg tgccctggag cccctacctg      1380
ttccagccca acgacacctg catcgtgagc ggctggggcc gcgagaagga caacgagcgc      1440
gtgttcagcc tgcagtgggg cgaggtgaag ctgatcagca actgcagcaa gttctacggc      1500
aaccgcttct acgagaagga gatggagtgc gccggcacct acgacggcag catcgacgcc      1560
tgcaagggcg acagcggcgg cccccctggtg tgcatggacg ccaacaacgt gacctacgtg      1620
tggggcgtgg tgagctgggg cgagaactgc ggcaagcccg agttccccgg cgtgtacacc      1680
aaggtggcca actacttcga ctggatcagc taccacgtgg ccgcccctt catcagccag       1740 tacaacgtgt aa                                                          1752
```

<210> SEQ ID NO 25
<211> LENGTH: 1752
<212> TYPE: DNA
<213> ORGANISM: Artificial Sequence
<220> FEATURE:
<223> OTHER INFORMATION: RC135: CFI JCat - Manually optimised

<400> SEQUENCE: 25

```
atgaagctgc tccacgtgtt cctgctcttc ctgtgcttcc acctgcgctt ctgcaaggtg        60
acctacacca gccaggagga cctggtggag aagaaatgcc tggccaagaa atacacccac       120
ctgagctgcg acaaggtgtt ctgccagccc tggcagcgct gcatcgaggg cacctgcgtg       180
tgcaagctgc cctaccagtg ccccaagaac ggcaccgccg tgtgcgccac caaccgccgg       240
agcttcccca cctactgcca gcaaaagagc ctggagtgcc tgcaccccgg caccaagttc       300
ctgaacaatg gcacctgcac cgccgagggc aagttcagcg tgagcctgaa gcacggcaac       360
accgacagcg agggcatcgt ggaggtgaag ctggtggacc aggacaagac catgttcatc       420
tgcaagagct cctggagcat gcgcgaggcc aacgtggcct gcctggacct gggcttccag       480
caaggcgccg acacccagcg ccggttcaag ctgagcgacc tgagcatcaa cagcaccgag       540
tgcctgcacg tgcactgccg cggcctggag accagcctgg ccgagtgcac cttcaccaag       600
cgccggacca tgggctacca ggacttcgcc gacgtggtct gctacaccca gaaggctgac       660
tctcccatgg acgatttctt tcagtgcgtg aacggcaagt acatcagcca gatgaaggcc       720
tgcgacggca tcaacgactg cggcgaccag agcgacgagc tgtgctgtaa ggcctgccag       780
ggcaagggct tccactgcaa gagcggcgtg tgcatcccca gccagtacca gtgcaacggc       840
gaggtggact gcatcaccgg cgaggacgag gtgggctgcg ccggcttcgc cagcgtggcc       900
caggaggaaa ccgagatcct gaccgccgac atggacgccg agcgcagaag gatcaagagc       960
ctgctcccca gctgagctg cggcgtgaag aaccgcatgc acatccgcag aaagcgcatc      1020
gtgggcggga gcgcgcccca gctgggcgac ctgccctggc aggtggccat caaggacgcc      1080
agcggcatca cctgcggcgg aatctacatc ggcgggtgct ggatcctgac cgccgctcac      1140
tgcctgcgcg ccagcaagac ccaccgctac cagatctgga ccacagtggt cgactggatc      1200
caccccgacc tgaagcgcat cgtgatcgag tacgtggacc gcatcatttt ccacgagaac      1260
tacaacgccg gcacctacca gaacgacatc gccctgatcg agatgaagaa agatggaaac      1320
aagaaagact gcgagctgcc ccgcagcatc cccgcctgcg tgccctggag cccctacctg      1380
ttccagccca acgacacctg catcgtgagc ggctggggcc gcgagaagga caacgagcgc      1440
gtgttcagcc tgcagtgggg cgaggtgaag ctgatcagca actgcagcaa gttctacggc      1500
```

-continued

```
aaccgcttct acgagaagga gatggagtgc gccggcacct acgacggcag catcgacgcc    1560
tgcaagggcg acagcggcgg gcccctggtg tgcatggacg ccaacaatgt gacctacgtg    1620
tggggcgtgg tcagctgggg cgagaactgc ggcaagcccg agttccccgg cgtgtacacc    1680
aaggtggcca actacttcga ctggatcagc taccacgtgg gccgcccctt tatctctcaa    1740
tacaacgtct aa                                                        1752

<210> SEQ ID NO 26
<211> LENGTH: 1752
<212> TYPE: DNA
<213> ORGANISM: Artificial Sequence
<220> FEATURE:
<223> OTHER INFORMATION: RC137: CFI COOL - Manually optimised

<400> SEQUENCE: 26
atgaaactgc tccatgtctt cctcctgttc ctgtgcttcc acctccgttt ctgtaaagtc      60
acctacacta gccaggagga tctggtggag aagaaatgcc tggccaagaa atatacccac     120
ctgagctgcg acaaagtgtt ctgccagccc tggcaacgct gcattgaagg cacttgtgtg     180
tgcaagctgc cctaccagtg ccccaagaac ggcacggccg tgtgtgccac caacaggaga     240
agcttcccca cctactgcca gcaaaagagc ctggaatgcc tccaccctgg caccaagttt     300
ctgaacaatg ggacctgcac agccgagggg aaattcagcg tctccctcaa gcacggcaat     360
acagactccg agggcattgt ggaagtgaag ctggtggacc aggacaagac catgttcatc     420
tgcaaaagct cctggtccat gcgggaggcc aatgtcgcct gcctggacct gggcttccag     480
caaggcgctg atacacagcg cagatttaaa ctcagtgacc tcagcatcaa cagcactgag     540
tgtctgcacg tgcactgccg gggcctggag accagcctgg ctgagtgcac cttcaccaag     600
cgcaggacca tgggctacca ggattttgca gatgtggtct gctacacccca gaaggcagac     660 agccccatgg atgacttctt tcagtgtgtc aatggcaagt acatttccca gatgaaggct     720
tgtgacggga tcaatgattg cggggatcag agcgatgagc tctgctgtaa ggcctgccaa     780
gggaagggct ttcactgcaa gtctgggggtg tgcatcccctt ctcagtatca gtgcaacgga     840
gaggtggact gcatcactgg ggaggacgag gtgggctgtg ctggcttcgc ctctgtggcc     900
caggaggaaa cagagatcct cacagctgac atggatgcag agcggaggcg catcaagagt     960
ctgctcccaa agctctcctg cggcgttaag aatcgcatgc acatccggag gaagcggatc    1020
gttggaggca acgggctca gctgggggac ttgccgtggc aggtggccat caaagatgcc    1080
tccggaatca cctgtggtgg catctacatc ggcgggtgct ggatcctgac cgccgctcac    1140
tgccttcggg ccagcaagac ccatcgctac cagatctgga ccacagtggt cgattggatt    1200 cacccccgacc tgaagaggat tgtcattgag tatgtcgacc gcatcatttt ccatgaaaac    1260
tacaatgccg ggacgtatca gaacgacatc gccctcatcg agatgaagaa agatgggaac    1320
aagaaagact gtgagctgcc tcgctccatc cccgcctgtg taccatggtc tccgtacctg    1380
ttccagccaa atgacacatg catcgtgagc ggctgggggcc gcgagaaaga caacgagagg    1440
gtcttctccc tgcagtgggg tgaagtcaag ctgatcagca actgctccaa gttctacggc    1500
aaccgcttct atgagaagga gatggagtgc gccggcacct atgacggcag cattgacgcg    1560
tgcaagggag acagtggggg cccctggtc tgcatggacg ccaacaatgt gacctacgtg    1620
tggggagttg tgtcctgggg cgagaactgt ggcaagcctg agttcccggg cgtgtacaca    1680
aaggtggcaa actattttga ctggatctcc tatcacgttg gcaggcccctt cattagccag    1740 tataatgtat aa                                                        1752
```

```
<210> SEQ ID NO 27
<211> LENGTH: 1350
<212> TYPE: DNA
<213> ORGANISM: Artificial Sequence
<220> FEATURE:
<223> OTHER INFORMATION: RC138: FHL-1 GeneArt - Basic

<400> SEQUENCE: 27
atgagactgc tggccaagat catctgcctg atgctgtggg ccatctgcgt ggccgaggat      60
tgcaatgagc tgcctcctcg agaaacacc gagatcctga caggctcttg gagcgaccag     120
acataccctg agggaaccca ggccatctac aagtgcagac ccggctacag aagcctgggc     180
aacatcatca tggtctgccg gaaaggcgag tgggtcgccc tgaatcctct gcggaagtgc     240
cagaaaagac cctgcggaca ccctggcgat accccttcg gaacctttac actgaccggc     300
ggcaacgtgt tcgagtacgg cgtgaaagcc gtgtacacct gtaacgaggg ctaccagctg     360
ctgggcgaga tcaactacag agagtgcgat accgacggct ggaccaacga catccctatc     420
tgcgaggtgg tcaagtgcct gcctgtgaca gcccctgaga cggcaagat tgtgtccagc     480 gccatggaac ccgacagaga gtaccacttt ggccaggccg tcagattcgt gtgcaacagc     540
ggctacaaga tcgagggcga cgaggaaatg cactgcagcg acgatggctt ctggtccaaa     600
gaaaagccta agtgcgtgga aatcagctgc aagagcccg acgtgatcaa cggcagccct     660
atcagccaga agattatcta caaagagaac gagcggttcc agtacaagtg taacatgggc     720
tacgagtaca gcgagagggg cgacgccgtg tgtacagaat ctggatggcg acctctgcct     780
agctgcgagg aaaagagctg cgacaaccct tacatcccca acggcgacta cagcccactg     840
cggatcaaac acagaaccgg cgacgagatc acctaccagt gccggaatgg cttctaccct     900
gccaccagag gcaataccgc caagtgtaca agcaccggct ggatccctgc tcctcggtgt     960
acactgaagc cctgcgacta ccccgatatc aagcacggcg gactgtacca cgagaacatg    1020
cggaggcctt acttccctgt ggccgtgggc aagtactaca gctactactg cgacgagcac    1080
ttcgagacac ccagcggcag ctactgggat cacatccact gtacccagga cggctggtca    1140
ccagctgtgc cttgcctgag aaagtgctac ttcccctacc tggaaaacgg ctacaaccag    1200
aactacggcc ggaagttcgt gcagggcaag agcatcgatg tggcctgcca tcctggatac    1260
gccctgccta aggctcagac caccgtgacc tgcatggaaa atggctggtc cccaacacct    1320
cggtgcatcc gggtgtcctt cacactgtaa    1350

<210> SEQ ID NO 28
<211> LENGTH: 1350
<212> TYPE: DNA
<213> ORGANISM: Artificial Sequence
<220> FEATURE:
<223> OTHER INFORMATION: RC139: FHL-1 GeneArt - Manually optimised

<400> SEQUENCE: 28
atgagactgc tcgccaagat catttgcctg atgctgtggg ccatctgcgt ggccgaggat      60
tgcaatgagc tgcctccccg agaaacacc gagatcctga caggctcttg gagcgaccag     120
acataccctg agggaaccca ggccatctac aagtgcagac ccggctacag aagcctgggc     180
aacatcatta tggtctgccg gaaaggcgag tgggtcgccc tgaatcctct gcggaagtgc     240
cagaaaagac cctgcggaca ccctggcgat accccttcg gaacctttac actgaccggc     300
gggaacgtgt tcgagtacgg cgtgaaagcc gtgtacacct gtaacgaggg ctaccagctg     360
```

-continued

```
ctcggcgaga tcaactacag agagtgcgat accgacggct ggaccaacga catccctatc      420
tgcgaggtgg tcaagtgcct gcctgtgaca gcccctgaga acggcaagat tgtgtccagc      480
gccatggaac ccgacagaga gtaccacttt ggccaggccg tcagattcgt gtgcaacagc      540
ggctacaaga tcgagggcga cgaggaaatg cactgcagcg acgatggctt ctggtccaaa      600
gaaaagccta agtgcgtgga aatcagctgc aagagccccg acgtgatcaa cggcagccct      660
atcagccaga agattatcta caaagagaac gagcggttcc agtacaagtg taacatgggc      720
tacgagtaca gcgagagggg cgacgccgtg tgtacagaat ctggatggcg acctctgcct      780
agctgcgagg aaaagagctg cgacaaccct tacatcccca acggcgacta cagcccactg      840
cggatcaaac acagaaccgg cgacgagatc acctaccagt gccggaatgg cttctaccct      900
gccaccagag gcaataccgc caagtgtaca agcaccggct ggatccctgc tcctcggtgt      960
acactgaagc cctgcgacta ccccgatatc aagcacggcg gactgtacca cgagaacatg     1020
cggaggcctt acttccctgt ggccgtgggc aagtactata gctactattg cgacgagcac     1080
ttcgagacac cagcggcag ctactgggat cacatccact gtacccagga cggctggtca       1140
ccagctgtgc cttgcctgag aaagtgctac ttccctacc tggaaaacgg ctacaaccag       1200
aactacggcc ggaagttcgt gcagggcaag agcatcgatg tggcctgcca tcctggatac     1260
gccctgccta aggctcagac cacagtgacc tgcatggaaa atggctggtc cccaacacct     1320
cggtgcatcc gggtgtcctt cacactgtaa                                       1350
```

```
<210> SEQ ID NO 29
<211> LENGTH: 1350
<212> TYPE: DNA
<213> ORGANISM: Artificial Sequence
<220> FEATURE:
<223> OTHER INFORMATION: RC140: FHL-1 Genscript - Basic

<400> SEQUENCE: 29
```

```
atgcggctgc tggccaagat catctgcctg atgctgtggg ccatctgcgt ggccgaggac       60
tgtaacgagc tgccccctcg agaaatacac gagatcctga ccggctcttg gagcgatcag      120
acatatcctg agggcaccca ggccatctac aagtgcaggc caggctatcg ctccctgggc      180
aacatcatca tggtgtgcag gaagggagag tgggtggccc tgaatcctct gaggaagtgc      240
cagaagaggc catgtggaca cccaggcgac acccctttcg gcacctttac actgaccggc      300
ggcaacgtgt tcgagtacgg cgtgaaggcc gtgtatacat gcaacgaggg ctaccagctg      360
ctgggcgaga tcaattacag agagtgtgac acagatggct ggaccaacga tatcccaatc      420
tgcgaggtgg tgaagtgtct gccagtgacc gcccccgaga atggcaagat cgtgagctcc      480
gccatggagc ccgacaggga gtatcacttc ggccaggccg tgcgcttcgt gtgcaactct      540
ggctacaaga tcgagggcga tgaggagatg cactgtagcg acgatggctt ctggtccaag      600
gagaagccca agtgcgtgga gatcagctgt aagtccccag acgtgatcaa tggctctccc      660
atcagccaga agatcatcta taaggagaac gagaggtttc agtacaagtg caatatgggc      720
tacgagtatt ccgagagggg cgatgccgtg tgcaccgagt ctggctggag accactgccc      780
tcctgcgagg agaagtcttg tgacaaccca tatatcccca atggcgatta ctctcccctg      840
cggatcaagc acagaacagg cgacgagatc acctatcagt gccggaacgg cttctaccct      900
gccacaagag gcaataccgc caagtgtaca agcaccggat ggatccctgc accaaggtgc      960
accctgaagc cttgtgacta tccagatatc aagcacggcg gcctgtatca cgagaatatg     1020
aggcgcccct acttcccagt ggccgtgggc aagtactata gctactattg cgacgagcac     1080
```

-continued

```
tttgagaccc cttccggctc ttactgggac cacatccact gtacacagga tggatggtcc      1140
ccagcagtgc cttgcctgag gaagtgttac ttcccatatc tggagaacgg ctacaaccag      1200
aattatggcc gcaagtttgt gcagggcaag agcatcgatg tggcatgcca cccaggatac      1260
gcactgccta aggcacagac cacagtgaca tgcatggaga atggctggtc tcccacccct      1320
cggtgtatca gagtgagctt tacactgtga                                       1350
```

```
<210> SEQ ID NO 30
<211> LENGTH: 1350
<212> TYPE: DNA
<213> ORGANISM: Artificial Sequence
<220> FEATURE:
<223> OTHER INFORMATION: RC141: FHL-1 Genscript - Manually optimised

<400> SEQUENCE: 30
```

```
atgcggctgc tcgccaagat catttgcctg atgctgtggg ccatctgcgt ggccgaggac      60
tgtaacgagc tgcccccctcg agaaataca gagatcctga ccggctcttg gagcgatcag      120
acatatcctg agggcaccca ggccatctac aagtgcaggc caggctatcg ctccctgggc      180
aacatcatta tggtgtgcag gaagggagag tgggtggccc tgaatcctct gaggaagtgc      240
cagaagaggc catgtggaca cccaggcgac accccttctcg gcacctttac actgaccggc      300
gggaacgtgt tcgagtacgg cgtgaaggcc gtgtatacat gcaacgaggg ctaccagctg      360
ctcggcgaga tcaattacag agagtgtgac acagatggct ggaccaacga tatcccaatc      420
tgcgaggtgg tcaagtgtct gccagtgacc gccccccgaga atggcaagat cgtgagctcc      480
gccatggagc ccgacaggga gtatcacttc ggccaggccg tgcgcttcgt gtgcaactct      540
ggctacaaga tcgagggcga tgaggaaatg cactgtagcg acgatggctt ctggtccaag      600
gagaagccca agtgcgtgga gatcagctgc aagtccccag acgtgatcaa tggctctccc      660
atcagccaga gatcattta taaggagaac gagaggtttc agtacaagtg caatatgggc      720
tacgagtatt ccgagagggg cgatgccgtg tgcaccgagt ctggctggag accactgccc      780
tcctgcgagg aaaagtcttg tgacaaccca tatatcccca atggcgatta ctctcccctg      840
cggatcaagc acagaacagg cgacgagatc acctatcagt gccggaacgg cttctaccct      900
gccacaagag gcaataccgc caagtgtaca agcaccggat ggatccctgc caaggtgc       960 accctgaagc cttgtgacta tccagatatc aagcacggcg gctgtatca cgagaatatg      1020 aggcgcccct acttcccagt ggccgtgggc aagtactata gctactattg cgacgagcac      1080
tttgagaccc cttccggctc ttactgggac cacatccact gtacacagga tggatggtcc      1140
ccagcagtgc cttgcctgag gaagtgttac ttcccatatc tggagaacgg ctacaaccag      1200
aattatggcc gcaagtttgt gcagggcaag agcatcgatg tggcatgcca cccaggatac      1260
gcactgccta aggcacagac cacagtgaca tgcatggaga atggctggtc tcccacccct      1320
cggtgtatca gagtgagctt tacactgtga                                       1350
```

```
<210> SEQ ID NO 31
<211> LENGTH: 1350
<212> TYPE: DNA
<213> ORGANISM: Artificial Sequence
<220> FEATURE:
<223> OTHER INFORMATION: RC142: FHL-1 IDT - Basic

<400> SEQUENCE: 31
```

```
atgagactgc ttgcgaaaat tatatgcctg atgctttggg ctatttgcgt tgcggaagac      60
```

-continued

```
tgtaacgaac tcccgccccg ccgaaataca gagatcctca caggcagttg gagcgaccaa        120
acgtaccctg aaggtacgca ggccatatat aagtgtaggc caggctacag atcacttggt        180
aacataataa tggtatgtcg gaaaggagag tgggtcgctc tcaaccctct taggaaatgt        240
caaaaaagac cctgtgggca tccgggagat acgcctttcg ggacattcac tctcacgggc        300
ggaaacgtat tcgaatatgg cgtgaaggca gtgtatacct gcaatgaagg gtatcagctg        360 cttgggaaa ttaattatag ggaatgtgac acggatgggg ggacaaacga tattccaata         420
tgcgaagtag ttaaatgcct gcccgttact gcaccggaga atggcaaaat agtcagtagt        480
gcaatggagc cggatcgcga gtatcatttt ggtcaggccg tgcggttcgt atgtaattct        540
gggtacaaga tcgaaggtga cgaagagatg cattgctcag atgacggctt ttggagtaaa        600
gaaaagccta agtgtgttga aatcagctgt aagagtccag acgtgattaa cggttccccg        660
atctctcaga agataattta caaggaaaac gaacgattcc aatataagtg taacatgggc        720
tacgagtatt ccgagcgagg tgacgcagta tgtacggaaa gcgggtggcg acctctgccc        780
tcctgcgagg aaaagagctg tgataatccg tatatcccca acggtgacta tagcccactg        840
cgcataaaac atcggacggg agatgagatt acataccaat gccgcaatgg ttttttacccc       900 gccacccgag ggaacacggc aaagtgcact tctacggggt ggattccagc tcctaggtgc        960
actcttaaac cctgcgacta cccagatatc aagcatggtg gactgtatca tgagaatatg       1020
aggagaccat actttccagt tgcagtgggc aagtactata gctattactg tgatgagcac       1080
tttgaaactc cgtctgggag ctactgggat catatccatt gtacgcaaga cggctggagt       1140
ccagcagttc catgcttgcg gaaatgttat tttccctacc tcgaaaacgg atataatcag       1200
aactatggga ggaagtttgt tcaaggcaaa agcattgatg tggcatgtca ccccggttat       1260
gccctgccca aggcgcaaac cacagtaact tgcatggaga atggatggag ccccacaccc       1320
agatgtatac gagtatcctt cacgctttga                                         1350
```

<210> SEQ ID NO 32
<211> LENGTH: 1350
<212> TYPE: DNA
<213> ORGANISM: Artificial Sequence
<220> FEATURE:
<223> OTHER INFORMATION: RC143: FHL-1 IDT - Manually optimised
<400> SEQUENCE: 32

```
atgagactgc ttgcgaaaat tatatgcctg atgctttggg ctatttgcgt tgcggaagac         60
tgtaacgaac tcccgccccg ccgaaataca gagatcctca caggcagttg gagcgaccaa        120
acgtaccctg aaggcacgca ggccatatat aagtgtaggc caggctacag atcacttggt        180
aacataatca tggtgtgtcg gaaaggagag tgggtcgctc tcaaccctct tcgcaaatgt        240
caaaaaagac cctgtgggca tccgggagat acgcctttcg ggacattcac tctcacgggc        300
ggaaacgtat tcgaatatgg cgtgaaggca gtgtatacct gcaatgaagg gtatcagctg        360 cttgggaaa ttaattatag ggaatgtgac acggatgggg ggacaaacga tattccaata         420
tgcgaagtag ttaaatgcct gcccgttact gcaccggaga atggcaaaat agtcagtagc        480
gcaatggagc cggatcgcga gtatcatttt ggtcaggccg tgcggttcgt atgtaattct        540
gggtacaaga tcgaaggtga cgaagagatg cattgctcag atgacggctt ttggagcaag        600
gaaaagccta agtgtgttga aatcagctgt aagagtccag acgtgattaa cggttccccg        660
atctctcaga agataattta caaggaaaac gaacgattcc aatataagtg taacatgggc        720
tacgagtatt ccgagcgagg tgacgcagta tgtacggaaa gcgggtggcg acctctgccc        780
```

-continued

```
tcctgcgagg aaaagagctg tgataatccg tatatcccca acggcgacta tagcccactg        840
cgcataaaac atcggacggg agatgagatt acataccaat gccgcaatgg tttttaccccc       900 gccacccgag ggaacacggc aaagtgcact tctacggggt ggattccagc tcctaggtgc       960
actcttaaac cctgcgacta cccagatatc aagcatggtg gactgtatca tgagaatatg      1020
aggagaccat actttccagt tgcagtgggc aagtactata gctattactg tgatgagcac      1080
tttgaaactc cgtctgggag ctactgggat catatccatt gtacgcaaga cggctggagt      1140
ccagcagttc catgcttgcg gaaatgttat tttccctacc tcgaaaacgg atataatcag      1200
aattacggca ggaaatttgt gcaaggcaaa agcattgatg tggcatgtca ccccggttat      1260
gccctgccca aggcgcaaac cacagtaact tgcatggaga atggatggag ccccacaccc      1320
agatgtatac gagtatcctt cacgctttga                                       1350
```

```
<210> SEQ ID NO 33
<211> LENGTH: 1350
<212> TYPE: DNA
<213> ORGANISM: Artificial Sequence
<220> FEATURE:
<223> OTHER INFORMATION: RC144: FHL-1 JCat - Basic

<400> SEQUENCE: 33
atgcgcctgc tggccaagat catctgcctg atgctgtggg ccatctgcgt ggccgaggac        60
tgcaacgagc tgccccccccg ccgcaacacc gagatcctga ccggcagctg gagcgaccag       120
acctaccccg agggcacccca ggccatctac aagtgccgcc ccggctaccg cagcctgggc       180
aacatcatca tggtgtgccg caagggcgag tgggtggccc tgaaccccct gcgcaagtgc        240
cagaagcgcc cctgcggcca ccccggcgac acccccttcg gcaccttcac cctgaccggc        300
ggcaacgtgt tcgagtacgg cgtgaaggcc gtgtacacct gcaacgaggg ctaccagctg        360
ctgggcgaga tcaactaccg cgagtgcgac accgacggct ggaccaacga catccccatc        420
tgcgaggtgg tgaagtgcct gcccgtgacc gcccccgaga acggcaagat cgtgagcagc        480
gccatggagc ccgaccgcga gtaccacttc ggccaggccg tgcgcttcgt gtgcaacagc        540
ggctacaaga tcgagggcga cgaggagatg cactgcagcg acgacggctt ctggagcaag        600
gagaagccca gtgcgtggga gatcagctgc aagagccccg acgtgatcaa cggcagcccc        660
atcagccaga agatcatcta caaggagaac gagcgcttcc agtacaagtg caacatgggc        720
tacgagtaca gcgagcgcgg cgacgccgtg tgcaccgaga gcggctggcg cccccctgccc        780 agctgcgagg agaagagctg cgacaacccc tacatcccca acggcgacta cagcccc      840 cgcatcaagc accgcaccgg cgacgagatc acctaccagt gccgcaacgg cttctacccc        900
gccacccgcg gcaacaccgc caagtgcacc agcaccggct ggatcccgc ccccgctgc        960 accctgaagc cctgcgacta ccccgacatc aagcacggcg gcctgtacca cgagaacatg      1020
cgccgcccct acttccccgt ggccgtgggc aagtactaca gctactactg cgacgagcac      1080
ttcgagaccc ccagcggcag ctactgggac cacatccact gcacccagga cggctggagc      1140
cccgccgtgc cctgcctgcg caagtgctac ttcccctacc tggagaacgg ctacaaccag      1200
aactacggcc gcaagttcgt gcagggcaag agcatcgacg tggcctgcca ccccggctac      1260
gccctgccca aggcccagac caccgtgacc tgcatggaga acggctggag ccccacccccc      1320 cgctgcatcc gcgtgagctt caccctgtaa                                       1350
```

```
<210> SEQ ID NO 34
```

```
<211> LENGTH: 1350
<212> TYPE: DNA
<213> ORGANISM: Artificial Sequence
<220> FEATURE:
<223> OTHER INFORMATION: RC145: FHL-1 JCat - Manually optimised

<400> SEQUENCE: 34
atgcgcctgc tcgccaagat catttgcctg atgctgtggg ccatctgcgt ggccgaggac     60
tgcaacgagc tgccccctcg ccggaacacc gagatcctga ccggcagctg gagcgaccag    120
acctaccccg agggcaccca ggccatctac aagtgccgcc ccggctaccg cagcctgggc    180
aacatcatta tggtgtgccg caagggcgag tgggtggccc tgaaccccct gcgcaagtgc    240
cagaagcgcc cctgcggcca ccccggcgac accccccttcg gcaccttcac cctgaccggc    300
ggcaacgtgt tcgagtacgg cgtgaaggcc gtgtacacct gcaacgaggg ctaccagctg    360
ctcggcgaga tcaactaccg cgagtgcgac accgacggct ggaccaacga catccccatc    420
tgcgaggtgg tcaagtgcct gcccgtgacc gcccccgaga acggcaagat cgtgagctcc    480
gccatggagc ccgaccgcga gtaccacttc ggccaggccg tgcgcttcgt gtgcaacagc    540
ggctacaaga tcgagggcga cgaggagatg cactgcagcg acgatggctt ctggagcaag    600
gagaagccca gtgcgtgga gatcagctgc aagagccccg acgtgatcaa cggcagcccc    660
atcagccaga agatcattta caaggagaac gagcgcttcc agtacaagtg caacatgggc    720
tacgagtaca gcgagcgcgg cgacgccgtg tgcaccgaga gcggctggcg cccccctgccc    780 agctgcgagg aaaagagctg cgacaacccc tacatcccca acggcgacta cagcccctg    840 cgcatcaagc accgcaccgg cgacgagatc acctaccagt gccgcaacgg cttctacccc    900
gccacccgcg gcaacaccgc caagtgcacc agcaccggct ggatccccgc ccccgctgc    960 accctgaagc cctgcgacta ccccgacatc aagcacggcg gctgtacca cgagaacatg   1020 cgccggccct acttccccgt ggccgtgggc aagtactata gctactattg cgacgagcac   1080
ttcgagaccc ccagcggcag ctactgggac cacatccact gcacccagga cggctggagc   1140
cccgccgtgc cctgcctgcg caagtgctac ttccctacc tggagaacgg ctacaaccag   1200
aactacggcc gcaagttcgt gcagggcaag agcatcgacg tggcctgcca ccccggctac   1260
gccctgccca aggcccagac cacagtgacc tgcatggaga acggctggag ccccacccc   1320 cgctgcatcc gcgtgagctt caccctgtaa                                     1350

<210> SEQ ID NO 35
<211> LENGTH: 1350
<212> TYPE: DNA
<213> ORGANISM: Artificial Sequence
<220> FEATURE:
<223> OTHER INFORMATION: RC147: FHL-1 COOL - Manually optimised

<400> SEQUENCE: 35
atgcgcctcc tggccaagat catttgcctc atgctgtggg ccatctgcgt ggctgaggac     60
tgcaatgagc tgccgcccag gagaaacaca gagatcctga cagggagctg gtctgaccag    120
acctaccctg agggcaccca ggcgatctac aagtgccggc cgggctacag gagcctgggg    180
aacatcatta tggtgtgtag aaagggcgaa tgggtggccc tcaacccct gaggaagtgc    240 cagaagcggc cctgtggcca ccccggggac acacccttcg gaccttcac cctgaccggc    300 gggaatgtgt ttgagtacgg cgtgaaggct gtctacacat gcaacgaggg gtaccagctg    360
ctcggcgaga ttaactaccg gggtgtgac accgatgggt ggaccaacga cattcccatc    420
tgtgaggtgg tcaagtgtct ccccgtgaca gccccagaaa atggcaaaat tgtgagctcc    480
```

-continued

```
gccatggagc ctgaccgcga atatcacttt gggcaggccg tgaggtttgt gtgcaactcg      540
ggctacaaaa ttgaaggtga tgaggaaatg cactgcagcg atgacggctt ctggtccaag      600
gagaagccca aatgtgtgga gatctcctgc aagtctcccg acgtgatcaa cggcagccca      660
atcagccaga agattatcta caaagagaac gagcgcttcc agtacaagtg taacatgggc      720
tatgagtatt cagagagggg agatgccgtc tgcactgaga gcggctggag accactgcct      780
agctgcgagg aaaagagttg tgacaaccct tacatcccaa atggcgacta ctcccctctg      840
cggatcaaac accggaccgg ggatgaaatc acctatcagt gccgcaatgg attctacccg      900
gccacccgcg gcaacaccgc caaatgcacc agcacaggct ggatccccgc ccccgctgt      960 acgctgaagc cttgcgacta tccagacatc aagcacggag gcctgtacca cgaaaacatg     1020
cggaggcctt atttccctgt ggcagtgggg aagtactata gctactattg cgacgagcac     1080
ttcgagaccc cctctggctc ctactgggac cacatccact gcacacagga cggctggtct     1140
ccagctgtgc cctgcctgag gaaatgctac ttcccctacc tggagaacgg atacaaccag     1200
aactatggcc gcaagttcgt gcagggcaag agcatcgatg tggcctgcca ccctggctac     1260
gccctgccca aggcccagac aactgtgacc tgcatggaga atggttggag ccccacccccg     1320 cgctgcatcc gggtgtcctt cacgctctga                                       1350
```

CODON-OPTIMISED COMPLEMENT FACTOR I

SEQUENCE LISTING

The instant application contains a Sequence Listing which has been submitted electronically in ASCII format and is hereby incorporated by reference in its entirety. The ASCII copy, created on Jun. 18, 2021, is named 2021-06-18_SE-QListing_7169-0102PUS1.txt and is 87,891 bytes in size.

FIELD OF THE INVENTION

The present invention relates to agents for use in gene therapy. In particular, the invention relates to polynucleotides encoding Complement Factor I (CFI) or Complement Factor H-like Protein 1 (FHL1), vectors comprising said polynucleotides, and their uses in the treatment or prevention of complement-mediated and complement-associated disorders, including eye diseases, such as age-related macular degeneration (AMD).

BACKGROUND TO THE INVENTION

The macula is a small area in the retina of the eye, approximately 3 to 5 millimetres in size, adjacent to the optic nerve. It is the most sensitive area of the retina and contains the fovea, a depressed region that allows for high visual acuity and contains a dense concentration of cones, the photoreceptors that are responsible for colour vision.

Age-related macular degeneration (AMD) is the most common cause of functional blindness in developed countries for persons over 50 years of age (Seddon, J. M., Epidemiology of age-related macular degeneration. In: Ogden, T. E., et al., eds. Ryan S. J., ed-in-chief. Retina Vol II. 3rd ed. St. Louis, Mo.: Mosby; 2001:1039-1050). AMD is associated with neovascularisation originating from the choroidal vasculature and extending into the subretinal space. In addition, AMD is characterised by progressive degeneration of the retina, retinal pigment epithelium (RPE), and underlying choroid (the highly vascular tissue that lies beneath the RPE, between the retina and the sclera).

A variety of factors including oxidative stress, inflammation with a possible autoimmune component, genetic background (e.g. mutations), and environmental or behavioural factors such as smoking and diet may contribute to the pathogenesis of AMD.

The clinical progression of AMD is characterised in stages according to changes in the macula. The hallmark of early AMD is the appearance of drusen, which are accumulations of extracellular debris underneath the retina and appear as yellow spots in the retina during clinical examination and on fundus photographs. Drusen are categorised by size as small (<63 μm), medium (63-124 μm) and large (>124 μm). They are also considered as hard or soft depending on the appearance of their margins on ophthalmological examination. While hard drusen have clearly defined margins, soft drusen have less defined, fluid margins. The Age-related Eye Disease Study (AREDS) fundus photographic severity scale is one of the main classification systems used for this condition.

AMD has been classified into "dry" and "wet" (exudative or neovascular) forms. Dry AMD is more common than wet AMD, but the dry form can progress to the wet form, and the two occur simultaneously in a significant number of cases. Dry AMD is typically characterised by progressive apoptosis of cells in the RPE layer, overlying photoreceptor cells, and frequently also the underlying cells in the choroidal capillary layer. Confluent areas of RPE cell death accompanied by overlying photoreceptor atrophy are referred to as geographic atrophy. Patients with this form of AMD experience a slow and progressive deterioration in central vision.

Wet AMD is characterised by bleeding and/or leakage of fluid from abnormal vessels that have grown from the choroidal vessels (choriocapillaris) beneath the RPE and the macula, which can be responsible for sudden and disabling loss of vision. It has been estimated that much of the vision loss that patients experience is due to such choroidal neovascularisation (CNV) and its secondary complications. A subtype of neovascular AMD is termed retinal angiomatous proliferation (RAP). Here, angiomatous proliferation originates from the retina and extends posteriorly into the subretinal space, eventually communicating in some cases with choroidal new vessels.

The complement system (CS) has been implicated in early AMD pathogenesis based on the identification of CS components in drusen from eyes of AMD patients. In AMD, at least 129 types of drusen-deposited proteins have been identified, including different apolipoprotein types (E, B or A-I), several amyloid peptides (P, Aβ or SA-1), TIMP-3, serum albumin, and certain proteins associated with cellular function (e.g. ATP synthase β subunit, scavenger receptor B2 and retinol dehydrogenase). AMD-derived drusen also contain almost all of the complement proteins, including regulatory proteins (CFH, complement receptor 1 (CR1), vitronectin and clusterin), the products of CS activation and degradation (C1q, C3, C3a, C3b and C5a), and members of the terminal CS pathway comprising the MAC components (i.e. 5, 6, 8 (α, β and γ) and 9) in the separated and complex form. Accumulating drusen may activate the CS, trigger the local production of inflammatory mediators, and attract leukocytes that in turn augment the local inflammatory state present in AMD.

Current treatment options for AMD include photodynamic therapy with benzoporphyrin (Arch Ophthalmol (1999) 117:1329-1345) and a number of therapies which target the Vascular Endothelial Growth Factor (VEGF) pathway. Examples of such VEGF-targeted therapies include the aptamer pegaptanib (N Engl J Med (2004) 351:2805-2816) and antibodies such as ranibizumab (N Engl J Med (2006) 355:1432-1444) and bevacizumab (BMJ (2010) 340: c2459). However, not all patients respond to treatment with an anti-VEGF antibody and either do not recover vision or progress to registered blindness.

A therapy for the treatment of geographic atrophy has been developed and was used in a phase III clinical study. Lampalizumab is a humanised monoclonal inhibitory antibody to Complement Factor D, administered by intravitreal injection to stop the rate of progression of geographic atrophy. However, in the Phase III randomised clinical trial, involving 906 participants, Lampalizumab failed to reduce GA enlargement when compared with sham over 48 weeks.

Accordingly, there is a significant need in the art for new approaches to treat eye diseases, such as AMD.

Due to the ubiquitous nature of the complement system, overactive or improperly-functioning complement system has been implicated in the pathology of many chronic inflammatory conditions for which treatment options either do not exist or require management of symptoms via regular interventions over a period of years. There is, therefore, a general need to develop gene therapy treatments that provide new or alternative treatments for complement-mediated and complement-associated disorders, particularly chronic inflammatory conditions and even more particularly those which are associated with overactivity of the complement C3b feedback cycle (FIG. 1).

SUMMARY OF THE INVENTION

The applicant has identified codon optimised sequences of Complement Factor I (CFI) and Complement Factor H-like Protein 1 (FHL1), which provide for substantially increased expression of the encoded CFI and FHL1 proteins compared to the wild type sequences.

The improved CFI- and FHL1-encoding sequences developed by the applicant enable higher doses of the respective proteins to be delivered to a patient without increasing the amount of vector that is administered. The invention therefore provides improvements in terms of manufacturing output (i.e. protein delivery can be achieved with lower amounts of vector that is produced), efficacy of the medicament and also safety. In particular, as a higher encoded protein dose may be achieved with delivery of the same amount (e.g. volume) of vector, the risk of damage to the tissue to which vector is administered is reduced. For example, when a vector is delivered to the eye by subretinal injection, the risk of damage to or detachment of the retina caused by injection of larger volumes of medicament is reduced. In addition, the risk of off-target effects that arise through spread of larger volumes of medicament to adjacent tissues is reduced. Furthermore, the use of the claimed nucleotide sequences in gene therapy, has the potential to deliver a treatment in a single dose, allowing for long-term, stable expression of protein, and avoiding the need for monthly or regular injections. The nucleotide sequences and compositions of the invention have the additional advantage, therefore, that they have the potential to provide a one-time or "single-shot" therapy that avoids repeated or regular surgical interventions.

In one aspect, the invention provides an isolated polynucleotide comprising a nucleotide sequence encoding Complement Factor I (CFI), wherein the nucleotide sequence has at least 85% sequence identity to SEQ ID NO: 10.

In some embodiments, the nucleotide sequence encoding CFI has at least 86%, 87%, 88%, 89%, 90%, 91%, 92%, 93%, 94%, 95%, 96%, 97%, 98% or 99% identity to SEQ ID NO: 10.

In preferred embodiments, the nucleotide sequence encoding CFI is SEQ ID NO: 10.

In another aspect, the invention provides an isolated polynucleotide comprising a nucleotide sequence encoding Complement Factor H-like Protein 1 (FHL1), wherein the nucleotide sequence has at least 75% sequence identity to SEQ ID NO: 12.

In some embodiments, the nucleotide sequence encoding FHL1 has at least 80%, 85%, 86%, 87%, 88%, 89%, 90%, 91%, 92%, 93%, 94%, 95%, 96%, 97%, 98% or 99% identity to SEQ ID NO: 12.

In preferred embodiments, the nucleotide sequence encoding FHL1 is SEQ ID NO: 12.

In some embodiments, the polynucleotide comprises one or more adeno-associated virus (AAV) inverted terminal repeats (ITRs). In preferred embodiments, the polynucleotide comprises an AAV ITR at its 5' end and an AAV ITR at its 3' end.

In some embodiments, the AAV ITRs are AAV2 or AAV8 ITRs. In preferred embodiments, the AAV ITRs are AAV2 ITRs.

In another aspect, the invention provides a vector comprising the polynucleotide of the invention.

In some embodiments, the vector is an adeno-associated viral (AAV), retroviral, lentiviral or adenoviral vector.

In preferred embodiments, the vector is an AAV vector.

In some embodiments, the vector is in the form of a viral vector particle.

In some embodiments, the AAV vector particle comprises an AAV2 or AAV8 genome.

In some embodiments, the AAV vector particle comprises AAV2 or AAV8 capsid proteins.

In some embodiments, the AAV vector particle comprises an AAV2 genome and AAV2 capsid proteins (AAV2/2). In other embodiments, the AAV vector particle comprises an AAV2 genome and AAV8 capsid proteins (AAV2/8). In other embodiments, the AAV vector particle comprises an AAV8 genome and AAV8 capsid proteins (AAV8/8).

In some embodiments, the nucleotide sequence encoding the CFI is operably linked to a CMV promoter. In some embodiments, the nucleotide sequence encoding the CFI is operably linked to a regulatory element, such as a WPRE regulatory element. In preferred embodiments, the WPRE regulatory element is a WPRE3 regulatory element. In some embodiments, the nucleotide sequence encoding the CFI is operably linked to a polyadenylation (poly-A) signal, such as a Bovine Growth Hormone poly-A signal.

In preferred embodiments, the nucleotide sequence encoding the CFI is operably linked to a CMV promoter; a WPRE regulatory element (preferably a WPRE3 regulatory element); and a Bovine Growth Hormone poly-A signal.

In some embodiments, the nucleotide sequence encoding the FHL1 is operably linked to a CMV promoter. In some embodiments, the nucleotide sequence encoding the FHL1 is operably linked to a regulatory element, such as WPRE regulatory element. In preferred embodiments, the WPRE regulatory element is a WPRE3 regulatory element. In some embodiments, the nucleotide sequence encoding the FHL1 is operably linked to a poly-A signal, such as a Bovine Growth Hormone poly-A signal.

In preferred embodiments, the nucleotide sequence encoding the FHL1 is operably linked to a CMV promoter; a WPRE regulatory element (preferably a WPRE3 regulatory element); and a Bovine Growth Hormone poly-A signal.

In another aspect, the invention provides a cell comprising the polynucleotide of the invention.

In another aspect, the invention provides a cell transduced with the vector of the invention.

In another aspect, the invention provides a pharmaceutical composition comprising the polynucleotide, vector or cell of the invention in combination with a pharmaceutically acceptable carrier, diluent or excipient.

In a particular embodiment, the pharmaceutical composition is suitable for systemic administration, e.g. by infusion via peripheral vein.

In a particular embodiment, the pharmaceutical composition is suitable for local administration, e.g. intrathecal administration.

In preferred embodiments, the pharmaceutical composition is for intraocular administration for example, by intravitreal injection, suprachoroidal injection or sub-retinal injection.

In another aspect, the invention provides the polynucleotide, vector or cell of the invention for use in therapy.

In a particular embodiment the polynucleotide, vector or cell of the invention is used in the treatment of complement-mediated disorders, particularly chronic inflammatory conditions.

In a preferred embodiment the polynucleotide, vector or cell of the invention is used in the treatment of a disorder associated with overactivity of the complement C3b feedback cycle.

In another aspect, the invention provides the polynucleotide, vector or cell of the invention for use in treating or preventing an ocular disorder.

In another aspect, the invention provides the polynucleotide, vector or cell of the invention for use in treating or preventing a complement-mediated disorder of the eye.

In another aspect, the invention provides a method of treating or preventing a complement-mediated disorder of the eye comprising administering the polynucleotide, vector or cell of the invention to a subject in need thereof.

In another aspect, the invention provides a method of providing Complement Factor I (CFI) and/or Complement Factor H-like Protein 1 (FHL1) to a subject, comprising delivering the polynucleotide, vector or cell of the invention to the eye of the subject.

In some embodiments, the disorder is associated with over-activity of the complement C3b feedback cycle and/or under-activity of the C3b breakdown cycle (see FIG. 1).

In some embodiments, the disorder is a chronic complement-mediated inflammatory condition of the eye.

In some embodiments, the disorder is age-related macular degeneration (AMD) or diabetic retinopathy. In other embodiments, the disorder is glaucoma, Stargardt's disease, central serous chorioretinopathy or retinitis pigmentosa.

In preferred embodiments, the disorder is AMD. In some embodiments, the AMD is dry AMD.

In some embodiments, a subject has been diagnosed with AMD or is at risk of acquiring AMD.

In some embodiments, the use is for treating or preventing a disorder in a subject:

(a) having lower than normal Complement Factor I activity or concentration in the eye and/or serum, preferably having a concentration of, or activity equivalent to, 0-30, 0-20 or 0-10 µg/mL in serum; and/or (b) being heterozygous or homozygous for an age-related macular degeneration (AMD)-associated SNP, preferably a rare Complement Factor I variant.

In some embodiments, the use is for treating or preventing a disorder in a subject:

(a) having a normal level of Complement Factor I activity or concentration in the eye and/or serum, preferably at least 30 µg/mL, such as 30-40 µg/mL in serum; and/or (b) not carrying a rare Complement Factor I variant allele.

In another aspect, the invention provides the polynucleotide, vector or cell of the invention for use in treating or preventing age-related macular degeneration (AMD). In preferred embodiments, the AMD is dry AMD.

In another aspect, the invention provides the polynucleotide, vector or cell of the invention for use in treating or preventing diabetic retinopathy.

In some embodiments, the formation of geographic atrophy is prevented or reduced, and/or the amount of geographic atrophy is reduced.

In some embodiments, the progression of geographic atrophy is slowed.

In some embodiments, there is at least a 10% reduction in the increase in geographic atrophy area over the 12 months following administration to a treated eye of a subject, relative to an untreated eye over the same period. In other embodiments, there is at least 20%, 30%, 40%, 50%, 60%, 70%, 80% or 90% reduction in the increase in geographic atrophy area over the 12 months following administration to a treated eye of a subject, relative to an untreated eye over the same period In some embodiments, administration of the polynucleotide, vector or cell increases the level of C3b-inactivating and iC3b-degradation activity in a subject, or in an eye, such as in the retinal pigment epithelium (RPE), of a subject, optionally to a level that exceeds a normal level in a subject, or eye or RPE thereof.

In another aspect, the invention provides the polynucleotide, vector or cell of the invention for use in improving or restoring vision or visual acuity, for example in a subject suffering from an eye disorder, such as an eye disorder disclosed herein. In another aspect, the invention provides the polynucleotide, vector or cell of the invention for use in mitigating loss of vision or visual acuity, for example a loss of vision or visual acuity associated with an eye disorder, such as an eye disorder disclosed herein.

In another aspect, the invention provides the polynucleotide, vector or cell of the invention for use in improving or restoring reading speed in a subject, for example in a subject suffering from an eye disorder, such as an eye disorder disclosed herein. In another aspect, the invention provides the polynucleotide, vector or cell of the invention for use in mitigating reduction in reading speed in a subject, for example a reduction in reading speed associated with an eye disorder, such as an eye disorder disclosed herein.

In another aspect, the invention provides the polynucleotide, vector or cell of the invention for use in reducing or preventing loss of photoreceptors and/or the retinal pigment epithelium (RPE), for example a loss of photoreceptors and/or the RPE associated with an eye disorder, such as an eye disorder disclosed herein.

In some embodiments, the polynucleotide, vector or cell is administered intraocularly.

In some embodiments, the polynucleotide, vector or cell is administered to the eye of a subject by subretinal, direct retinal, suprachoroidal or intravitreal injection.

In some embodiments, the polynucleotide, vector or cell is administered to the eye of a subject by subretinal injection.

In some embodiments, the polynucleotide or vector of the invention does not comprise a hAAT promoter. In some embodiments, the polynucleotide or vector of the invention does not comprise an ApoR enhancer. In other embodiments, the polynucleotide or vector of the invention does not comprise two ApoR enhancers.

In some embodiments, the vector of the invention does not comprise an AAV2 genome and an AAV8 capsid protein, i.e. the vector of the invention is not an AAV2/8 vector.

In some embodiments, the polynucleotide, vector or cell of the invention is not administered systemically. In other embodiments, the polynucleotide, vector or cell of the invention is not administered intravenously.

Figure 1:
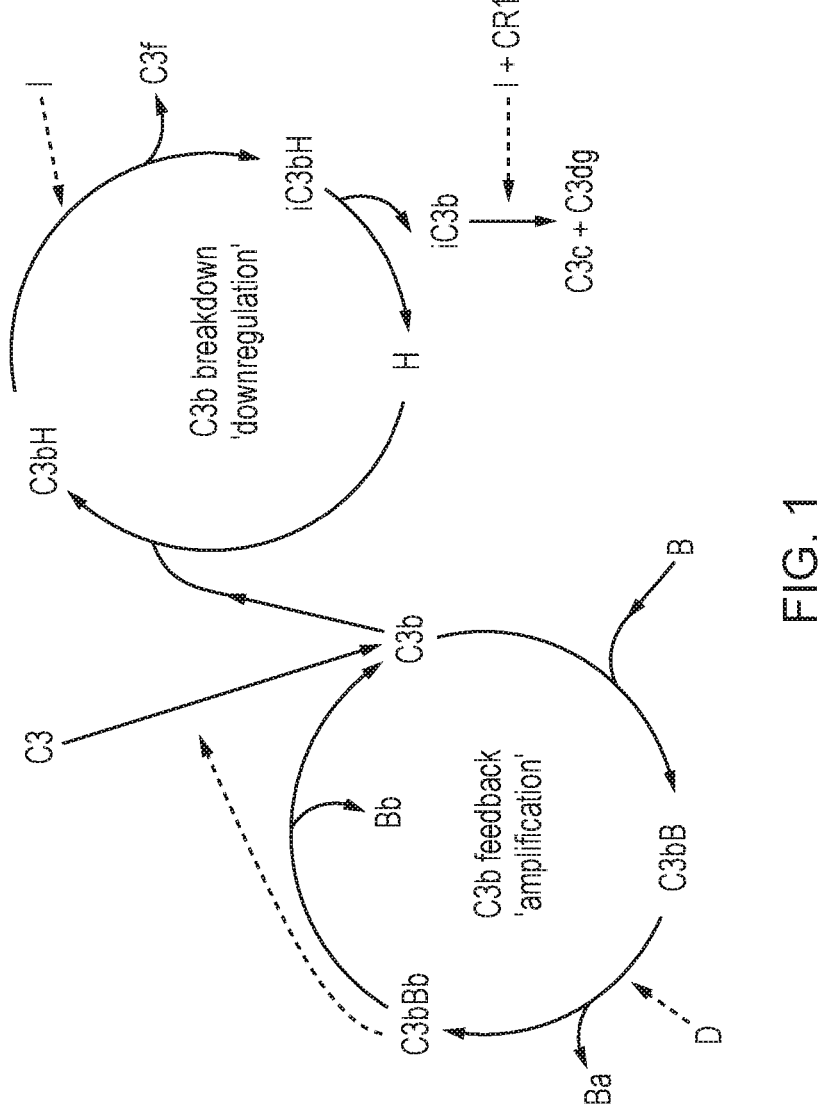
FIG. 1

C3b feedback (amplification) and breakdown (down-regulation) cycles of the alternative pathway of vertebrate complement ("I"=Complement Factor I; "H"=Complement Factor H; "B"=Complement Factor B; and "D"=Complement Factor D).

FIG. 2

Western blot analyses of supernatants from codon-optimised CFI and FHL1 plasmid transfection of ARPE19 cells.

FIG. 3

ELISA analyses of supernatants from codon-optimised CFI plasmid transfection of ARPE19 cells.

FIG. 4

ELISA analyses of supernatants from codon-optimised FHL1 plasmid transfection of ARPE19 cells.

FIG. 5

ELISA analyses of supernatants from codon-optimised CFI AAV vector transduction of ARPE19 cells.

FIG. 6

ELISA analyses of supernatants from codon-optimised FHL1 AAV vector transduction of ARPE19 cells.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Complement System

The complement system is an integral part of the humoral immune system and is involved in tissue inflammation, cell opsonisation, and cytolysis. It provides protection against microorganisms and mediates the clearance of exogenous and endogenous cellular debris from the host tissues.

The complement system cascade is comprised of four activation pathways. All of the pathways ultimately end in the central cleavage of C3 factor and in the generation of its active fragments C3a and C3b. C3a is the anaphylatoxin that triggers a range of chemotactic and proinflammatory responses, such as recruitment of inflammatory cells and increased microvasculature permeability, whereas C3b is responsible for opsonisation of foreign surfaces covalently attached to C3b. Opsonisation with activated C3 fragments (C3b and iC3b) fulfils three major functions: (i) cell debris elimination by phagocytic cells (e.g. macrophages or microglia) and the stimulation of the adaptive immune system (B and T cells); (ii) amplification of complement activation via the formation of a surface-bound C3 convertase; and (iii) assemblage of the C5 convertase.

Assemblage of the C5 convertase is responsible for C5 cleavage, which results in the formation of the cytolytic membrane attack complex (MAC) capable of generating perforations in the cell membrane, thereby promoting cell lysis and the elimination of unnecessary cells. Through all of these activities, the innate complement cascade supports and promotes the function of downstream mechanisms of the immune system that protect the integrity of the host tissue. Overall, complement system pathway activation results in a proinflammatory response, including MAC generation, which mediates cell lysis, the release of chemokines to attract inflammatory cells to the site of damage, and the enhancement of capillary permeability to promote extravasation of infiltrating leukocytes. Under physiological conditions, complement activation is effectively controlled by the coordinated action of soluble and membrane-associated complement regulatory molecules (CRMs). Soluble complement regulators, such as C1-inhibitor, anaphylatoxins inhibitor, C4b binding protein (C4BP), Complement Factor H (CFH), Complement Factor I (CFI), clusterin and vitronectin, restrict the action of complement in human tissues at multiple sites of the cascade reaction. In addition, each individual cell is protected against the attack of homologous complement by surface proteins, such as the Complement Receptor 1 (CR1, CD35), the membrane cofactor protein (CD46), and glycosylphosphatidylinositol-anchored proteins, such as decay-accelerating factor (CD55) or CD59 molecule. Of note, host cells and tissues that are inadequately protected from complement attack might be subjected to bystander cell lysis.

The invention relates to the treatment or prevention of a complement-mediated disorder of the eye. For example, the complement-mediated disorder may be a disorder associated with a defect in alternative pathway regulation, and in particular with over-activity of the complement C3b feedback cycle and/or under-activity of the C3b breakdown cycle.

In some embodiments, prior to administration of the polynucleotide, vector, cell or pharmaceutical composition of the invention, the subject has low levels (e.g. lower than normal levels) of Complement Factor I activity, for example low levels of Complement Factor I activity in the eye and/or low serum levels of Complement Factor I activity. The sub-normal level of Complement Factor I activity may be due to sub-normal expression of normally-functioning Complement Factor I, or at least partial (e.g. heterozygous) expression (at normal or sub-normal levels) of a non- or sub-functional variant of Complement Factor I. (Such a subject may carry one or more copies of an AMD-associated SNP, for example the subject may be homo- or heterozygous for one of the rare Complement Factor I variants discussed further below). Thus, the subject may have a low concentration (e.g. a lower than normal concentration) of Complement Factor I in the eye and/or serum. For a human subject, the normal level of Complement Factor I activity (C3b-inactivating and iC3b-degradation activity) may be equivalent to that provided by 30-40 $\mu$g/mL Complement Factor I in the serum of the subject. Thus, in a subject with low Complement Factor I activity, the Complement Factor I activity in the serum may correspond to less than 30 $\mu$g/mL and greater than 0 $\mu$g/mL Complement Factor I, such as 0-20 or 0-10 $\mu$g/mL (these being ranges of Complement Factor I serum concentration which may encompass a subject having a low Complement Factor I concentration).

Thus, the subject to be treated by the invention may suffer from a complement-mediated disorder of the eye such as AMD, more particularly dry AMD (e.g. characterised by geographic atrophy), or may be at risk of developing such a disorder. For example, the subject may be homozygous or heterozygous susceptible for one or more SNPs associated with the complement-mediated disorder.

In some embodiments, the subject is at risk of developing AMD. For example, the subject may be homozygous or heterozygous susceptible for one or more SNPs associated with AMD, for example rare mutations in Complement Factor I associated with advanced AMD which commonly result in reduced serum Complement Factor I levels (Kavanagh et al. (2015) Hum Mol Genet 24:3861-3870). In particular the subject may carry one or two copies of one or more of the following rare Complement Factor I variants: rs144082872 (encoding P50A); 4:110687847 (encoding P64L); rs141853578 (encoding G119R); 4:110685721 (encoding V152M); 4:110682846 (encoding G162D); 4:110682801 (encoding N177I); rs146444258 (encoding A240G); rs182078921 (encoding G287R); rs41278047 (encoding K441R); and rs121964913 (encoding R474).

The invention may further comprise determining whether the subject is at risk of developing a complement-mediated disorder (for example, AMD), for example by determining whether the subject is homozygous or heterozygous susceptible for one or more SNPs associated with the complement-mediated disorder (for example, by determining whether the subject is homozygous or heterozygous susceptible for one or more of the rare Complement Factor I variants associated with AMD listed above).

Alternatively, the subject may have a normal level of endogenous Complement Factor I activity or concentration, for example in the eye and/or serum and/or may not carry a rare variant Complement Factor I allele.

In some embodiments, administration of the polynucleotide, vector, cell or pharmaceutical composition of the invention thereby increases the level of C3b-inactivating and iC3b-degradation activity in the eye of the subject. In other embodiments, administration of the polynucleotide, vector, cell or pharmaceutical composition of the invention thereby increases the level of C3b-inactivating and iC3b-degradation activity in the eye of the subject to a level that exceeds a normal level in the eye. More particularly, the level of C3b-inactivating and iC3b-degradation activity is increased in the RPE of the eye.

It will be appreciated that the C3b-inactivating and iC3b-degradation activity in the subject following expression of the Complement Factor I from the polynucleotide or vector of the invention may comprise C3b-inactivating and iC3b-degradation activity from the subject's endogenous Complement Factor I (i.e. the subject's Complement Factor I not produced by expression from the polynucleotide or vector), and C3b-inactivating and iC3b-degradation activity produced by expression from the polynucleotide or vector of the invention, such that the total level of C3b-inactivating and iC3b-degradation activity in the subject exceeds a normal level.

In some embodiments, the level of C3b-inactivating and iC3b-degradation activity in the subject, for example in the eye, is increased to a level that is at least 5%, 10%, 15%, 20% or 25% above the normal level.

In other embodiments, the level of C3b-inactivating and iC3b-degradation activity in the subject, for example in the eye, is increased to a level that is up to twice the normal level, or up to 80%, 60%, 40% or 20% above the normal level.

For example, the level of C3b-inactivating and iC3b-degradation activity in the subject, for example in the eye, may be increased to a level that is 5-100%, 5-80%, 5-60%, 5-40%, 5-20%, 10-100%, 10-80%, 10-60%, 10-40%, 10-20%, 15-100%, 15-80%, 15-60%, 15-40%, 15-20%, 20-100%, 20-80%, 20-60%, 20-40%, 25-100%, 25-80%, 25-60% or 25-40% above the normal level.

In some embodiments, administration of the polynucleotide, vector, cell or pharmaceutical composition of the invention does not detectably increase the level of C3b-inactivating and iC3b-degradation activity in the plasma/serum of the subject. In other embodiments, administration of the polynucleotide, vector, cell or pharmaceutical composition of the invention does not detectably increase the level of C3b-inactivating and iC3b-degradation activity in the plasma/serum of the subject to a level greater than the normal level.

In the foregoing section, except where obviously inapplicable, reference to Complement Factor I and C3b-inactivating and iC3b-degradation activity may be replaced with Complement Factor H or Complement Factor H-like Protein 1, and ability to act as a cofactor for the Complement Factor I mediated cleavage of C3b and to increase the rate of dissociation of C3 convertase and C5 convertase, respectively. In some embodiments, prior to administration of the polynucleotide, vector, cell or pharmaceutical composition of the invention, the subject has low levels (e.g. lower than normal levels) of Complement Factor H, for example low levels of Complement Factor H in the eye and/or low serum levels of Complement Factor H. For a human subject, the normal level of Complement Factor H may be about 200-500 µg/mL in the serum of the subject. Thus, in a subject with low levels of Complement Factor H, the levels in the serum may be less than 200 µg/mL and greater than 0 g/mL, such as 0-100 µg/mL. Alternatively, the subject may have a normal level of endogenous Complement Factor H, for example in the eye and/or serum.

Complement Factor I (CFI)

Complement Factor I (Factor I, CFI), also known as C3b/C4b inactivator, is a protein that in humans is encoded by the CFI gene.

Complement Factor I is a serine protease that circulates in a zymogen-like state (Roversi et al. (2011) PNAS 108: 12839-12844) at a concentration of ~35 µg/mL (Nilsson et al. (2011) Mol Immunol 48:1611-1620). The Complement Factor I protein is a heavily N-glycosylated heterodimer consisting of two polypeptide chains linked by a single disulfide bond. The heavy chain (50 kDa) comprises an N-terminal region; an FI membrane attack complex (FI-MAC) domain; a CD5 like-domain or scavenger receptor cysteine-rich (SRCR) domain; two low-density lipoprotein receptor (LDLr) domains; and a C-terminal region of unknown function that is a site of sequence variability across species (Roversi et al. (2011) PNAS 108:12839-12844). The light chain (38 kDa) contains the serine protease (SP) domain with the conserved catalytic residues (Goldberger et al. (1987) J Biol Chem 262:10065-10071).

Complement Factor I inactivates C3b by cleaving it into iC3b, C3d and C3d,g and, in an analogous way, C4b into C4c and C4d. To properly perform its functions, Complement Factor I requires the presence of cofactor proteins such as C4b-Binding Protein (C4BP), Complement Factor H (CFH), Complement Receptor 1 (CR1/CD35) and Membrane Cofactor Protein (MCP/CD46) (Degn et al. (2011) Am J Hum Genet 88:689-705).

iC3b is incapable of associating with Factor B, and thus cannot perpetuate amplification of the complement cascade or activation through the alternative pathway. Hence, once C3b has been cleaved to iC3b, neither alternative pathway initiation nor terminal complement cascade activation occurs.

iC3b is capable of providing a proinflammatory action by binding to, and activating, Complement Receptor 3 (CR3) (CD11b/CD18) on polymorphonuclear leukocytes (mostly neutrophils), NK cells and mononuclear phagocytes, such as macrophages.

Complement Factor I is capable of processing iC3b into C3d,g via a protease activity requiring the cofactor, CR1. C3d, g is unable to bind to CR3. Since iC3b reacting with the complement receptor CR3 is a major mechanism by which complement activation gives rise to inflammation, the breakdown of iC3b to C3d,g is essential for reducing complement-induced inflammation (Lachmann (2009) Adv. Immunol. 104:115-149).

Complement Factor I's unique ability to both promote cleavage of C3b to iC3b as well as accelerate breakdown of iC3b—combined with its relatively low concentration in human serum, with implications for the amount required to be delivered for therapeutic efficacy-make it a particularly advantageous target.

In some embodiments, a Complement Factor I polypeptide is capable of cleaving C3b into an inactive degradation product. For example, the Complement Factor I polypeptide may be capable of cleaving C3b into iC3b.

In some embodiments, a Complement Factor I polypeptide is capable of processing iC3b into an inactive degradation product. For example, the Complement Factor I polypeptide may be capable of processing iC3b into C3d,g.

In preferred embodiments, the Complement Factor I polypeptide is capable of cleaving C3b into iC3b and processing iC3b into C3d,g.

Suitably, a fragment or derivative of Complement Factor I may retain at least 50%, 60%, 70%, 80%, 90%, 95% or 100% of the C3b-inactivating and iC3b-degradation activity of native Complement Factor I.

The C3b-inactivating and iC3b-degradation activity of Complement Factor I, or a fragment or derivative thereof, may be determined using any suitable method known to the skilled person. For example, measurement of Complement Factor I proteolytic activity is described in Hsiung et al. (Biochem. J. (1982) 203:293-298). Both haemolytic and conglutinating assays for CFI activity are described in Lachmann P J & Hobart M J (1978) "Complement Technology" in Handbook of Experimental Immunology 3rd edition Ed DM Weir Blackwells Scientific Publications Chapter 5A p17. A more detailed description, also including a proteolytic assay, is given by Harrison R A (1996) in "Weir's Handbook of Experimental Immunology" 5th Edition Eds; Herzenberg Leonore A'Weir D M, Herzenberg Leonard A & Blackwell C Blackwells Scientific Publications Chapter 75 36-37. The conglutinating assay is highly sensitive and can be used for detecting both the first (double) clip converting fixed C3b to iC3b and acquiring reactivity with conglutinin; and for detecting the final clip to C3dg by starting with fixed iC3b and looking for the loss of reactivity with conglutinin. The haemolytic assay is used for the conversion of C3b to iC3b, and the proteolytic assay detects all the clips.

In some embodiments, the Complement Factor I is human Complement Factor I.

An example human Complement Factor I protein is the human Complement Factor I protein having the UniProtKB accession number P05156. This exemplified sequence is 583 amino acids in length (disclosed as SEQ ID NO: 1) of which amino acids 1 to 18 form a signal sequence.

In some embodiments, the amino acid sequence of Complement Factor I is SEQ ID NO: 1. In other embodiments, the amino acid sequence of Complement Factor I is the sequence disclosed as positions 19 to 583 of SEQ ID NO: 1.

```
                                          (SEQ ID NO: 1)
MKLLHVFLLFLCFHLRFCKVTYTSQEDLVEKKCLAKKYTHLSCDKVFCQ

PWQRCIEGTCVCKLPYQCPKNGTAVCATNRRSFPTYCQQKSLECLHPGT

KFLNNGTCTAEGKESVSLKHGNTDSEGIVEVKLVDQDKTMFICKSSWSM

REANVACLDLGFQQGADTQRRFKLSDLSINSTECLHVHCRGLETSLAEC

TFTKRRTMGYQDFADVVCYTQKADSPMDDFFQCVNGKYISQMKACDGIN

DCGDQSDELCCKACQGKGFHCKSGVCIPSQYQCNGEVDCITGEDEVGCA
```

-continued
```
GFASVTQEETEILTADMDAERRRIKSLLPKLSCGVKNRMHIRRKRIVGG

KRAQLGDLPWQVAIKDASGITCGGIYIGGCWILTAAHCLRASKTHRYQI

WTTVVDWIHPDLKRIVIEYVDRIIFHENYNAGTYQNDIALIEMKKDGNK

KDCELPRSIPACVPWSPYLFQPNDTCIVSGWGREKDNERVESLQWGEVK

LISNCSKFYGNRFYEKEMECAGTYDGSIDACKGDSGGPLVCMDANNVTY

VWGVVSWGENCGKPEFPGVYTKVANYEDWISYHVGRPFISQYNV
```

In some embodiments, the amino acid sequence of Complement Factor I is SEQ ID NO: 9, which corresponds to NCBI Accession No. NP_000195. In other embodiments, the amino acid sequence of Complement Factor I is the sequence disclosed as positions 19 to 583 of SEQ ID NO: 9.

```
                                          (SEQ ID NO: 9)
MKLLHVFLLFLCFHLRFCKVTYTSQEDLVEKKCLAKKYTHLSCDKVFCQ

PWQRCIEGTCVCKLPYQCPKNGTAVCATNRRSFPTYCQQKSLECLHPGT

KFLNNGTCTAEGKFSVSLKHGNTDSEGIVEVKLVDQDKTMFICKSSWSM

REANVACLDLGFQQGADTQRREKLSDLSINSTECLHVHCRGLETSLAEC

TFTKRRTMGYQDFADVVCYTQKADSPMDDFFQCVNGKYISQMKACDGIN

DCGDQSDELCCKACQGKGFHCKSGVCIPSQYQCNGEVDCITGEDEVGCA

GFASVAQEETEILTADMDAERRRIKSLLPKLSCGVKNRMHIRRKRIVGG

KRAQLGDLPWQVAIKDASGITCGGIYIGGCWILTAAHCLRASKTHRYQI

WTTVVDWIHPDLKRIVIEYVDRIIFHENYNAGTYQNDIALIEMKKDGNK

KDCELPRSIPACVPWSPYLFQPNDTCIVSGWGREKDNERVESLQWGEVK

LISNCSKFYGNRFYEKEMECAGTYDGSIDACKGDSGGPLVCMDANNVTY

VWGVVSWGENCGKPEFPGVYTKVANYEDWISYHVGRPFISQYNV
```

An example wild type nucleotide sequence encoding Complement Factor I is the nucleotide sequence having the NCBI Accession No. NM_000204, disclosed herein as SEQ ID NO: 2.

```
                                          (SEQ ID NO: 2)
ATGAAGCTTCTTCATGTTTTCCTGTTATTTCTGTGCTTCCACTTAAGGT

TTTGCAAGGTCACTTATACATCTCAAGAGGATCTGGTGGAGAAAAAGTG

CTTAGCAAAAAAATATACTCACCTCTCCTGCGATAAAGTCTTCTGCCAG

CCATGGCAGAGATGCATTGAGGGCACCTGTGTTTGTAAACTACCGTATC

AGTGCCCAAAGAATGGCACTGCAGTGTGTGCAACTAACAGGAGAAGCTT

CCCAACATACTGTCAACAAAAGAGTTTGGAATGTCTTCATCCAGGGACA

AAGTTTTTAAATAACGGAACATGCACAGCCGAAGGAAAGTTTAGTGTTT

CCTTGAAGCATGGAAATACAGATTCAGAGGGAATAGTTGAAGTAAAACT

TGTGGACCAAGATAAGACAATGTTCATATGCAAAAGCAGCTGGAGCATG

AGGGAAGCCAACGTGGCCTGCCTTGACCTTGGGTTTCAACAAGGTGCTG

ATACTCAAAGAAGGTTTAAGTTGTCTGATCTCTCTATAAATTCCACTGA

ATGTCTACATGTGCATTGCCGAGGATTAGAGACCAGTTTGGCTGAATGT

ACTTTTTACTAAGAGAAGAACTATGGGTTACCAGGATTTCGCTGATGTGG

TTTGTTATACACAGAAAGCAGATTCTCCAATGGATGACTTCTTTCAGTG
```

-continued

```
TGTGAATGGGAAATACATTTCTCAGATGAAAGCCTGTGATGGTATCAAT

GATTGTGGAGACCAAAGTGATGAACTGTGTTGTAAAGCATGCCAAGGCA

AAGGCTTCCATTGCAAATCGGGTGTTTGCATTCCAAGCCAGTATCAATG

CAATGGTGAGGTGGACTGCATTACAGGGGAAGATGAAGTTGGCTGTGCA

GGCTTTGCATCTGTGGCTCAAGAAGAAACAGAAATTTTGACTGCTGACA

TGGATGCAGAAAGAAGACGGATAAAATCATTATTACCTAAACTATCTTG

TGGAGTTAAAAACAGAATGCACATTCGAAGGAAACGAATTGTGGGAGGA

AAGCGAGCACAACTGGGAGACCTCCCATGGCAGGTGGCAATTAAGGATG

CCAGTGGAATCACCTGTGGGGGAATTTATATTGGTGGCTGTTGGATTCT

GACTGCTGCACATTGTCTCAGAGCCAGTAAAACTCATCGTTACCAAATA

TGGACAACAGTAGTAGACTGGATACACCCCGACCTTAAACGTATAGTAA

TTGAATACGTGGATAGAATTATTTTCCATGAAAACTACAATGCAGGCAC

TTACCAAAATGACATCGCTTTGATTGAAATGAAAAAAGACGGAAACAAA

AAAGATTGTGAGCTGCCTCGTTCCATCCCTGCCTGTGTCCCCTGGTCTC

CTTACCTATTCCAACCTAATGATACATGCATCGTTTCTGGCTGGGGACG

AGAAAAAGATAACGAAAGAGTCTTTTCACTTCAGTGGGGTGAAGTTAAA

CTAATAAGCAACTGCTCTAAGTTTTACGGAAATCGTTTCTATGAAAAAG

AAATGGAATGTGCAGGTACATATGATGGTTCCATCGATGCCTGTAAAGG

GGACTCTGGAGGCCCCTTAGTCTGTATGGATGCCAACAATGTGACTTAT

GTCTGGGGTGTTGTGAGTTGGGGGGAAAACTGTGGAAAACCAGAGTTCC

CAGGTGTTTACACCAAAGTGGCCAATTATTTTGACTGGATTAGCTACCA

TGTAGGAAGGCCTTTTATTTCTCAGTACAATGTATAA
```

The nucleotide sequences of Complement Factor I used in the invention are preferably codon-optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

A preferred nucleotide sequence encoding Complement Factor I is the nucleotide sequence disclosed as SEQ ID NO: 10.

(SEQ ID NO: 10)
```
ATGAAACTGCTGCATGTCTTCCTCCTCTTCCTGTGCTTCCACCTCCGTT

TCTGTAAAGTCACCTACACTAGCCAGGAGGATCTGGTGGAGAAGAAATG

CCTGGCCAAGAAGTATACCCACCTGAGCTGCGACAAAGTGTTCTGCCAG

CCCTGGCAACGCTGCATTGAAGGTACTTGTGTGTGCAAGCTGCCCTACC

AGTGCCCCAAGAACGGCACGGCCGTGTGTGCCACCAACAGGAGGAGCTT

CCCCACCTACTGCCAGCAGAAGAGCCTGGAATGCCTCCACCCTGGCACC

AAGTTTCTGAACAACGGGACCTGCACAGCCGAGGGGAAATTCAGCGTCT
```

-continued
```
CCCTCAAGCACGGCAATACAGACTCCGAGGGCATTGTGGAAGTGAAGCT

GGTGGACCAGGACAAGACCATGTTCATCTGCAAAAGCAGCTGGTCCATG

CGGGAGGCCAATGTCGCCTGCCTGGACCTGGGCTTCCAGCAGGGCGCTG

ATACACAGCGCCGCTTTAAACTCAGTGACCTCAGCATCAACAGCACTGA

GTGTCTGCACGTGCACTGCCGGGGCCTGGAGACCAGCCTGGCTGAGTGC

ACCTTCACCAAGCGCAGGACCATGGGCTACCAGGATTTTGCAGATGTGG

TCTGCTACACCCAGAAGGCAGACAGCCCCATGGATGACTTCTTCCAGTG

TGTCAATGGCAAGTACATTTCCCAGATGAAGGCTTGTGACGGGATCAAT

GATTGCGGGGATCAGAGCGATGAGCTCTGCTGCAAGGCCTGCCAAGGGA

AGGGCTTTCACTGTAAGTCTGGGGTGTGCATCCCTTCTCAGTATCAGTG

CAACGGAGAGGTGGACTGCATCACTGGGGAGGACGAGGTGGGCTGTGCT

GGCTTCGCCTCTGTGGCCCAGGAGGAGACAGAGATCCTCACAGCTGACA

TGGATGCAGAGCGGCGGCGCATCAAGAGTCTGCTCCCAAAGCTCTCCTG

CGGCGTTAAGAATCGCATGCACATCCGGAGGAAGCGGATCGTTGGAGGC

AAACGGGCTCAGCTGGGGGACTTGCCGTGGCAGGTGGCCATCAAAGATG

CCTCCGGAATCACCTGTGGTGGCATCTACATCGGCGGCTGCTGGATCCT

GACCGCCGCCCACTGCCTTCGGGCCAGCAAGACTCACCGCTACCAGATC

TGGACCACCGTGGTGGATTGGATTCACCCCGACCTGAAGAGGATTGTCA

TTGAGTATGTCGACCGCATCATCTTCCATGAAAACTACAATGCCGGGAC

GTATCAGAACGACATCGCCCTCATCGAGATGAAGAAGGATGGGAACAAG

AAGGACTGTGAGCTGCCTCGCTCCATCCCCGCCTGTGTACCATGGTCTC

CGTACCTGTTCCAGCCAAATGACACATGCATCGTGAGCGGCTGGGGCCG

CGAGAAAGACAACGAGAGGGTCTTCTCCCTGCAGTGGGGTGAAGTCAAG

CTGATCAGCAACTGCTCCAAGTTCTACGGCAACCGCTTCTATGAGAAGG

AGATGGAGTGCGCCGGCACCTATGACGGCAGCATTGACGCGTGCAAGGG

AGACAGTGGGGGCCCCCTGGTCTGCATGGACGCCAACAATGTGACCTAC

GTGTGGGGGAGTTGTGTCCTGGGGCGAGAACTGTGGCAAGCCTGAGTTCC

CGGGCGTGTACACAAAGGTGGCAAACTATTTTGACTGGATCTCCTATCA

CGTTGGCAGGCCCTTCATTTCACAGTACAACGTATAA
```

In some embodiments, the nucleotide sequence encoding Complement Factor I has at least 85%, 86%, 87%, 88%, 89%, 90%, 91%, 92%, 93%, 94%, 95%, 96%, 97%, 98% or 99% identity to SEQ ID NO: 10. Preferably, the protein encoded by the nucleotide sequence substantially retains a functional activity of the protein represented by SEQ ID NO: 1 or 9.

In other embodiments, the nucleotide sequence encoding Complement Factor I is SEQ ID NO: 10.

In other embodiments, the nucleotide sequence encoding Complement Factor I has at least 85%, 90%, 91%, 92%, 93%, 94%, 95%, 96%, 97%, 98% or 99% identity to positions 55 to 1752 of SEQ ID NO: 10. Preferably, the protein encoded by the nucleotide sequence substantially retains a functional activity of the protein represented by SEQ ID NO: 1 or 9.

In other embodiments, the nucleotide sequence encoding Complement Factor I is positions 55 to 1752 of SEQ ID NO: 10.

A further example codon-optimised nucleotide sequence encoding Complement Factor I is SEQ ID NO: 8.

(SEQ ID NO: 8)

```
ATGAAGCTGCTGCATGTCTTTCTGCTGTTTCTGTGCTTCCATCTGCGGT

TCTGTAAAGTGACCTATACTAGCCAGGAGGATCTGGTGGAGAAGAAGTG

TCTGGCCAAGAAGTACACACACCTGAGCTGCGACAAGGTGTTCTGTCAG

CCTTGGCAGCGGTGCATCGAGGGCACCTGCGTGTGCAAGCTGCCTTACC

AGTGCCCAAAGAACGGCACCGCCGTGTGCGCCACAAATCGGAGATCTTT

TCCAACATATTGCCAGCAGAAGAGCCTGGAGTGTCTGCACCCCGGCACC

AAGTTCCTGAACAATGGCACCTGCACAGCCGAGGGCAAGTTTTCTGTGA

GCCTGAAGCACGGCAACACAGATAGCGAGGGCATCGTGGAGGTGAAGCT

GGTGGACCAGGATAAGACCATGTTCATCTGTAAGAGCTCCTGGTCCATG

AGGGAGGCAAACGTGGCATGCCTGGATCTGGGATTCCAGCAGGGAGCAG

ACACACAGAGGCGCTTTAAGCTGTCCGACCTGTCTATCAATAGCACCGA

GTGCCTGCACGTGCACTGTAGGGGCCTGGAGACATCCCTGGCAGAGTGC

ACCTTCACAAAGCGGAGAACCATGGGCTACCAGGACTTTGCCGACGTGG

TGTGCTATACCCAGAAGGCCGATAGCCCCATGGACGATTTCTTTCAGTG

CGTGAACGGCAAGTATATCTCCCAGATGAAGGCCTGCGACGGCATCAAT

GACTGTGGCGATCAGTCTGACGAGCTGTGCGTAAGGCCTGTCAGGGCA

AGGGCTTCCACTGCAAGAGCGGCGTGTGCATCCCTTCCCAGTACCAGTG

CAACGGCGAGGTGGATTGTATCACAGGAGAGGACGAAGTGGGATGCGCA

GGATTTGCATCTGTGGCACAGGAGGAGACAGAGATCCTGACAGCCGACA

TGGATGCCGAGAGGCGCCGGATCAAGTCTCTGCTGCCTAAGCTGAGCTG

TGGCGTGAAGAATCGGATGCACATCAGAAGGAAGCGCATCGTGGGAGGC

AAGAGGGCACAGCTGGGCGATCTGCCATGGCAGGTGGCCATCAAGGACG

CCTCTGGCATCACCTGCGGCGGCATCTACATCGGAGGATGTTGGATCCT

GACCGCAGCACACTGCCTGAGAGCAAGCAAGACACACAGGTATCAGATC

TGGACCACAGTGGTGGATTGGATCCACCCAGACCTGAAGAGAATCGTGA

TCGAGTACGTGGATAGGATCATCTTTCACGAGAACTACAATGCCGGCAC

ATATCAGAACGACATCGCCCTGATCGAGATGAAGAAGGATGGCAATAAG

AAGGACTGTGAGCTGCCCAGATCCATCCCTGCATGCGTGCCATGGAGCC

CCTATCTGTTCCAGCCCAACGATACCTGCATCGTGTCCGGATGGGGAAG

GGAGAAGGACAATGAGCGGGTGTTTTCTCTGCAGTGGGGCGAGGTGAAG

CTGATCTCCAACTGTTCTAAGTTCTACGGCAATAGGTTTTATGAGAAGG

AGATGGAGTGCGCCGGCACCTACGATGGCAGCATCGACGCCTGTAAGGG

CGATTCCGGAGGACCACTGGTGTGCATGGACGCAAACAATGTGACATAC

GTGTGGGGAGTGGTGTCCTGGGGAGAGAACTGCGGCAAGCCAGAGTTCC

CCGGCGTATATACCAAGGTGGCCAATTATTTTGATTGGATTTCCTACCA

CGTCGGCAGGCCCTTTATTTCCCAGTATAATGTCTAA
```

An advantage of the invention is that Complement Factor I is particularly difficult to prepare in the form of a purified protein. Accordingly, the inventors have devised a way of modulating the complement system, for example to enable treatments of age-related macular degeneration (AMD), by administering Complement Factor I in the form of an AAV vector comprising a Complement Factor I-encoding nucleotide sequence. The AAV vector may be administered to a site of interest, for example the eye, to enable in situ translation of the Complement Factor I polypeptide.

Complement Factor H (CFH)

Complement Factor H (Factor H, CFH) is a complement control protein.

Complement Factor H is a large (155 kDa), soluble glycoprotein that is present in human plasma at a typical concentration of 200-300 μg/mL (Hakobyan et al. (2008) 49 (5): 1983-90). The principal function of Complement Factor H is to regulate the alternative pathway of the complement system.

Complement Factor H provides cofactor activity for the Complement Factor I-mediated cleavage of C3b. Complement Factor H also increases the rate of dissociation of the C3bBb complex (C3 convertase) and the (C3b) NBB complex (C5 convertase) and thereby reduces the activity of the alternative complement pathway.

Complement Factor H is made up of 20 complement control protein (CCP) modules (also referred to as Short Consensus Repeats or sushi domains) connected to one another by short linkers (of between three and eight amino acid residues) and arranged in an extended head to tail fashion. Each of the CCP modules consists of around 60 amino acids with four cysteine residues disulfide bonded in a 1-3 2-4 arrangement, and a hydrophobic core built around an almost invariant tryptophan residue. The CCP modules are numbered from 1-20 (from the N-terminus of the protein). CCPs 1-4 and CCPs 19-20 engage with C3b while CCPs 7 and CCPs 19-20 bind to GAGs and sialic acid (Schmidt et al. (2008) Journal of Immunology 181:2610-2619).

It has been shown that gene therapy using Complement Factor H can ameliorate induced AMD-like pathology in mice (Cashman et al. (2015) J. Gene Med. 17:229-243). Mice were co-injected subretinally with: (i) an adenoviral vector expressing complement component C3, which had previously been shown to recapitulate many pathological features of human AMD; and (ii) an adenoviral vector expressing Complement Factor H. Relative to control animals receiving GFP instead of Complement Factor H, the Complement Factor H-transduced mice showed 91% reduction in endothelial cell proliferation and 69% attenuation of RPE atrophy. Electroretinography showed improved retinal function in mice receiving Complement Factor H, and immunocytochemistry of rhodopsin and RPE65 was consistent with the rescue of photoreceptors and RPE in such animals.

In some embodiments, a Complement Factor H polypeptide or a fragment or derivative thereof is capable of acting as a cofactor for the Complement Factor I-mediated cleavage of C3b. In some embodiments, a Complement Factor H polypeptide or a fragment or derivative thereof is capable of increasing the rate of dissociation of C3 convertase and C5 convertase.

In preferred embodiments, a Complement Factor H polypeptide or a fragment or derivative thereof is capable of acting as a cofactor for the Complement Factor I-mediated cleavage of C3b and increasing the rate of dissociation of C3 convertase and C5 convertase.

In some embodiments, the Complement Factor H is human Complement Factor H.

An example human Complement Factor H protein is the human Complement Factor H protein having the UniProtKB accession number P08603. This exemplified sequence is 1231 amino acids in length (disclosed as SEQ ID NO: 3) of which amino acids 1 to 18 form a signal sequence.

In some embodiments, the amino acid sequence of Complement Factor H is SEQ ID NO: 3. In other embodiments, the amino acid sequence of Complement Factor H is positions 19 to 1231 of SEQ ID NO: 3.

```
                                          (SEQ ID NO: 3)
MRLLAKIICLMLWAICVAEDCNELPPRRNTEILTGSWSDQTYPEGTQAI

YKCRPGYRSLGNVIMVCRKGEWVALNPLRKCQKRPCGHPGDTPFGTFTL

TGGNVFEYGVKAVYTCNEGYQLLGEINYRECDTDGWTNDIPICEVVKCL

PVTAPENGKIVSSAMEPDREYHFGQAVRFVCNSGYKIEGDEEMHCSDDG

FWSKEKPKCVEISCKSPDVINGSPISQKIIYKENERFQYKCNMGYEYSE

RGDAVCTESGWRPLPSCEEKSCDNPYIPNGDYSPLRIKHRTGDEITYQC

RNGFYPATRGNTAKCTSTGWIPAPRCTLKPCDYPDIKHGGLYHENMRRP

YFPVAVGKYYSYYCDEHFETPSGSYWDHIHCTQDGWSPAVPCLRKCYFP

YLENGYNQNYGRKFVQGKSIDVACHPGYALPKAQTTVTCMENGWSPTPR

CIRVKTCSKSSIDIENGFISESQYTYALKEKAKYQCKLGYVTADGETSG

SITCGKDGWSAQPTCIKSCDIPVFMNARTKNDFTWFKLNDTLDYECHDG

YESNTGSTTGSIVCGYNGWSDLPICYERECELPKIDVHLVPDRKKDQYK

VGEVLKFSCKPGFTIVGPNSVQCYHFGLSPDLPICKEQVQSCGPPPELL

NGNVKEKTKEEYGHSEVVEYYCNPRFLMKGPNKIQCVDGEWTTLPVCIV

EESTCGDIPELEHGWAQLSSPPYYYGDSVEENCSESFTMIGHRSITCIH

GVWTQLPQCVAIDKLKKCKSSNLIILEEHLKNKKEFDHNSNIRYRCRGK

EGWIHTVCINGRWDPEVNCSMAQIQLCPPPPQIPNSHNMTTTLNYRDGE

KVSVLCQENYLIQEGEEITCKDGRWQSIPLCVEKIPCSQPPQIEHGTIN

SSRSSQESYAHGTKLSYTCEGGFRISEENETTCYMGKWSSPPQCEGLPC

KSPPEISHGVVAHMSDSYQYGEEVTYKCFEGFGIDGPAIAKCLGEKWSH

PPSCIKTDCLSLPSFENAIPMGEKKDVYKAGEQVTYTCATYYKMDGASN

VTCINSRWTGRPTCRDTSCVNPPTVQNAYIVSRQMSKYPSGERVRYQCR

SPYEMFGDEEVMCLNGNWTEPPQCKDSTGKCGPPPPIDNGDITSFPLSV

YAPASSVEYQCQNLYQLEGNKRITCRNGQWSEPPKCLHPCVISREIMEN

YNIALRWTAKQKLYSRTGESVEFVCKRGYRLSSRSHTLRTTCWDGKLEY

PTCAKR
```

An example nucleotide sequence encoding Complement Factor H is the nucleotide sequence having the NCBI Accession No. NM_000186.

In some embodiments, the nucleotide sequence encoding Complement Factor H is SEQ ID NO: 4.

```
                                          (SEQ ID NO: 4)
ATGAGACTTCTAGCAAAGATTATTTGCCTTATGTTATGGGCTATTTGTG

TAGCAGAAGATTGCAATGAACTTCCTCCAAGAAGAAATACAGAAATTCT

GACAGGTTCCTGGTCTGACCAAACATATCCAGAAGGCACCCAGGCTATC

TATAAATGCCGCCCTGGATATAGATCTCTTGGAAATGTAATAATGGTAT

GCAGGAAGGGAGAATGGGTTGCTCTTAATCCATTAAGGAAATGTCAGAA
```

-continued

```
AAGGCCCTGTGGACATCCTGGAGATACTCCTTTTGGTACTTTTACCCTT

ACAGGAGGAAATGTGTTTGAATATGGTGTAAAAGCTGTGTATACATGTA

ATGAGGGGTATCAATTGCTAGGTGAGATTAATTACCGTGAATGTGACAC

AGATGGATGGACCAATGATATTCCTATATGTGAAGTTGTGAAGTGTTTA

CCAGTGACAGCACCAGAGAATGGAAAAATTGTCAGTAGTGCAATGGAAC

CAGATCGGGAATACCATTTTGGACAAGCAGTACGGTTTGTATGTAACTC

AGGCTACAAGATTGAAGGAGATGAAGAAATGCATTGTTCAGACGATGGT

TTTTGGAGTAAAGAGAAACCAAAGTGTGTGGAAATTTCATGCAAATCCC

CAGATGTTATAAATGGATCTCCTATATCTCAGAAGATTATTTATAAGGA

GAATGAACGATTTCAATATAAATGTAACATGGGTTATGAATACAGTGAA

AGAGGAGATGCTGTATGCACTGAATCTGGATGGCGTCCGTTGCCTTCAT

GTGAAGAAAATCATGTGATAATCCTTATATTCCAAATGGTGACTACTC

ACCTTTAAGGATTAAACACAGAACTGGAGATGAAATCACGTACCAGTGT

AGAAATGGTTTTTATCCTGCAACCCGGGGAAATACAGCAAAATGCACAA

GTACTGGCTGGATACCTGCTCCGAGATGTACCTTGAAACCTTGTGATTA

TCCAGACATTAAACATGGAGGTCTATATCATGAGAATATGCGTAGACCA

TACTTTCCAGTAGCTGTAGGAAAATATTACTCCTATTACTGTGATGAAC

ATTTTGAGACTCCGTCAGGAAGTTACTGGGATCACATTCATTGCACACA

AGATGGATGGTCGCCAGCAGTACCATGCCTCAGAAAATGTTATTTTCCT

TATTTGGAAAATGGATATAATCAAAATCATGGAAGAAAGTTTGTACAGG

GTAAATCTATAGACGTTGCCTGCCATCCTGGCTACGCTCTTCCAAAAGC

GCAGACCACAGTTACATGTATGGAGAATGGCTGGTCTCCTACTCCCAGA

TGCATCCGTGTCAAAACATGTTCCAAATCAAGTATAGATATTGAGAATG

GGTTTATTTCTGAATCTCAGTATACATATGCCTTAAAAGAAAAAGCGAA

ATATCAATGCAAACTAGGATATGTAACAGCAGATGGTGAAACATCAGGA

TCAATTACATGTGGGAAAGATGGATGGTCAGCTCAACCCACGTGCATTA

AATCTTGTGATATCCCAGTATTTATGAATGCCAGAACTAAAAATGACTT

CACATGGTTTAAGCTGAATGACACATTGGACTATGAATGCCATGATGGT

TATGAAAGCAATACTGGAAGCACCACTGGTTCCATAGTGTGTGGTTACA

ATGGTTGGTCTGATTTACCCATATGTTATGAAAGAGAATGCGAACTTCC

TAAAATAGATGTACACTTAGTTCCTGATCGCAAGAAAGACCAGTATAAA

GTTGGAGAGGTGTTGAAATTCTCCTGCAAACCAGGATTTACAATAGTTG

GACCTAATTCCGTTCAGTGCTACCACTTTGGATTGTCTCCTGACCTCCC

AATATGTAAAGAGCAAGTACAATCATGTGGTCCACCTCCTGAACTCCTC

AATGGGAATGTTAAGGAAAAAACGAAAGAAGAATATGGACACAGTGAAG

TGGTGGAATATTATTGCAATCCTAGATTTCTAATGAAGGGACCTAATAA

AATTCAATGTGTTGATGGAGAGTGGACAACTTTACCAGTGTGTATTGTG

GAGGAGAGTACCTGTGGAGATATACCTGAACTTGAACATGGCTGGGCCC

AGCTTTCTTCCCCTCCTTATTACTATGGAGATTCAGTGGAATTCAATTG

CTCAGAATCATTTACAATGATTGGACACAGATCAATTACGTGTATTCAT

GGAGTATGGACCCAACTTCCCCAGTGTGTGGCAATAGATAAACTTAAGA
```

-continued

```
AGTGCAAATCATCAAATTTAATTATACTTGAGGAACATTTAAAAAACAA

GAAGGAATTCGATCATAATTCTAACATAAGGTACAGATGTAGAGGAAAA

GAAGGATGGATACACACAGTCTGCATAAATGGAAGATGGGATCCAGAAG

TGAACTGCTCAATGGCACAAATACAATTATGCCCACCTCCACCTCAGAT

TCCCAATTCTCACAATATGACAACCACACTGAATTATCGGGATGGAGAA

AAAGTATCTGTTCTTTGCCAAGAAAATTATCTAATTCAGGAAGGAGAAG

AAATTACATGCAAAGATGGAAGATGGCAGTCAATACCACTCTGTGTTGA

AAAAATTCCATGTTCACAACCACCTCAGATAGAACACGGAACCATTAAT

TCATCCAGGTCTTCACAAGAAAGTTATGCACATGGGACTAAATTGAGTT

ATACTTGTGAGGGTGGTTTCAGGATATCTGAAGAAAATGAAACAACATG

CTACATGGGAAAATGGAGTTCTCCACCTCAGTGTGAAGGCCTTCCTTGT

AAATCTCCACCTGAGATTTCTCATGGTGTTGTAGCTCACATGTCAGACA

GTTATCAGTATGGAGAAGAAGTTACGTACAAATGTTTTGAAGGTTTTGG

AATTGATGGGCCTGCAATTGCAAAATGCTTAGGAGAAAAATGGTCTCAC

CCTCCATCATGCATAAAAACAGATTGTCTCAGTTTACCTAGCTTTGAAA

ATGCCATACCCATGGGAGAAGAAGGATGTGTATAAGGCGGGTGAGCA

AGTGACTTACACTTGTGCAACATATTACAAAATGGATGGAGCCAGTAAT

GTAACATGCATTAATAGCAGATGGACAGGAAGGCCAACATGCAGAGACA

CCTCCTGTGTGAATCCGCCCACAGTACAAAATGCTTATATAGTGTCGAG

ACAGATGAGTAAATATCCATCTGGTGAGAGAGTACGTTATCAATGTAGG

AGCCCTTATGAAATGTTTGGGGATGAAGAAGTGATGTGTTTAAATGGAA

ACTGGACGGAACCACCTCAATGCAAAGATTCTACAGGAAAATGTGGGCC

CCCTCCACCTATTGACAATGGGGACATTACTTCATTCCCGTTGTCAGTA

TATGCTCCAGCTTCATCAGTTGAGTACCAATGCCAGAACTTGTATCAAC

TTGAGGGTAACAAGCGAATAACATGTAGAAATGGACAATGGTCAGAACC

ACCAAAATGCTTACATCCGTGTGTAATATCCCGAGAAATTATGGAAAAT

TATAACATAGCATTAAGGTGGACAGCCAAACAGAAGCTTTATTCGAGAA

CAGGTGAATCAGTTGAATTTGTGTGTAAACGGGGATATCGTCTTTCATC

ACGTTCTCACACATTGCGAACAACATGTTGGGATGGGAAACTGGAGTAT

CCAACTTGTGCAAAAGATAG
```

In some embodiments, the nucleotide sequence encoding Complement Factor H has at least 75%, 80%, 85%, 90%, 95%, 96%, 97%, 98% or 99% identity to SEQ ID NO: 4. Preferably, wherein the protein encoded by the nucleotide sequence substantially retains a functional activity of the protein represented by SEQ ID NO: 3.

In other embodiments, the nucleotide sequence encoding Complement Factor H is SEQ ID NO: 4.

In other embodiments, the nucleotide sequence encoding Complement Factor H has at least 75%, 80%, 85% 90%, 95%, 96%, 97%, 98% or 99% identity to positions 55 to 3696 of SEQ ID NO: 4. Preferably, wherein the protein encoded by the nucleotide sequence substantially retains a functional activity of the protein represented by SEQ ID NO: 3.

In other embodiments, the nucleotide sequence encoding Complement Factor H is positions 55 to 3696 of SEQ ID NO: 4.

In other embodiments, the nucleotide sequence encoding Complement Factor H encodes an amino acid sequence that has at least 75%, 80%, 85% 90%, 95%, 96%, 97%, 98% or 99% identity to SEQ ID NO: 3. Preferably, wherein the amino acid sequence substantially retains a functional activity of the protein represented by SEQ ID NO: 3.

In other embodiments, the nucleotide sequence encoding Complement Factor H encodes the amino acid sequence SEQ ID NO: 3.

In other embodiment, the nucleotide sequence encoding Complement Factor H encodes an amino acid sequence that has at least 75%, 80%, 85%, 90%, 95%, 96%, 97%, 98%, 99% identity to positions 19 to 1231 of SEQ ID NO: 3. Preferably, wherein the amino acid sequence substantially retains a functional activity of the protein represented by SEQ ID NO: 3.

In other embodiments, the nucleotide sequence encoding Complement Factor H encodes the amino acid sequence of positions 19 to 1231 of SEQ ID NO: 3.

Complement Factor H-Like Protein 1 (FHL1)

Complement Factor H-like Protein 1 (FHL1) is a splice variant of Complement Factor H that contains the first 7 CCPs of Complement Factor H followed by a four amino acid carboxy-terminal tail (Clark, S. J. et al. (2015) J Clin Med 4:18-31).

In some embodiments, the FHL1 is human FHL1.

In some embodiments, the amino acid sequence of FHL1 is SEQ ID NO: 11.

```
                                          (SEQ ID NO: 11)
MRLLAKIICLMLWAICVAEDCNELPPRRNTEILTGSWSDQTYPEGTQAI

YKCRPGYRSLGNIIMVCRKGEWVALNPLRKCQKRPCGHPGDTPFGTFTL

TGGNVFEYGVKAVYTCNEGYQLLGEINYRECDTDGWTNDIPICEVVKCL

PVTAPENGKIVSSAMEPDREYHFGQAVRFVCNSGYKIEGDEEMHCSDDG

FWSKEKPKCVEISCKSPDVINGSPISQKIIYKENERFQYKCNMGYEYSE

RGDAVCTESGWRPLPSCEEKSCDNPYIPNGDYSPLRIKHRTGDEITYQC

RNGFYPATRGNTAKCTSTGWIPAPRCTLKPCDYPDIKHGGLYHENMRRP

YFPVAVGKYYSYYCDEHFETPSGSYWDHIHCTQDGWSPAVPCLRKCYFP

YLENGYNQNYGRKFVQGKSIDVACHPGYALPKAQTTVTCMENGWSPTPR

CIRVSFTL
```

The nucleotide sequences of FHL1 used in the invention are preferably codon optimised.

A preferred nucleotide sequence encoding FHL1 is SEQ ID NO: 12.

```
                                          (SEQ ID NO: 12)
ATGCGCCTCCTGGCCAAGATCATCTGCCTCATGCTGTGGGCCATCTGCG

TGGCTGAGGACTGCAATGAGCTGCCGCCCAGGAGGAACACAGAGATCCT

GACAGGGAGCTGGTCTGACCAGACCTACCCTGAGGGCACCCAGGCGATC

TACAAGTGCCGGCCGGGCTACAGGAGCCTGGGGAACATCATCATGGTGT

GTAGAAAGGGCGAATGGGTGGCCCTCAACCCCCCTGAGGAAGTGCCAGAA

GCGGCCCTGTGGCCACCCCGGGGACACACCCTTCGGGACCTTCACCCTG

ACCGGCGGCAATGTGTTTGAGTACGGCGTGAAGGCTGTCTACACATGCA

ACGAGGGGTACCAGCTGCTGGGCGAGATTAACTACCGGGAGTGTGACAC
```

-continued

```
CGATGGGTGGACCAACGACATTCCCATCTGTGAGGTGGTCAAGTGTCTC

CCCGTGACAGCCCCAGAAAATGGCAAAATCGTGAGCAGCGCCATGGAGC

CTGACCGCGAATATCACTTTGGGCAGGCCGTGAGGTTTGTGTGCAACTC

GGGCTACAAAATTGAAGGTGATGAGGAGATGCACTGCAGCGATGATGGC

TTCTGGTCCAAGGAGAAGCCCAAATGTGTGGAGATCTCCTGCAAGTCTC

CCGACGTGATCAACGGCAGCCCAATCAGCCAGAAGATTATTTACAAAGA

GAACGAGCGCTTCCAGTACAAGTGTAACATGGGCTATGAGTATTCAGAG

AGGGGAGATGCCGTCTGCACTGAGAGCGGCTGGAGACCACTGCCTAGCT

GCGAGGAAAGAGTTGTGACAACCCTTACATCCCAAATGGCGACTACTC

CCCTCTGCGGATCAAACACCGGACCGGGGATGAAATCACCTATCAGTGC

CGCAATGGATTCTACCCGGCCACCCGCGGCAACACCGCCAAATGCACCA

GCACAGGCTGGATCCCCGCCCCCCCGCTGTACGCTGAAGCCTTGCGACTA

TCCAGACATCAAGCACGGAGGCCTGTACCACGAAAACATGCGGCGGCCT

TATTTCCCTGTGGCAGTGGGGAAGTACTACAGCTACTACTGCGACGAGC

ACTTCGAGACCCCCTCTGGCTCCTACTGGGACCACATCCACTGCACACA

GGACGGCTGGTCTCCAGCTGTGCCCTGCCTGAGGAAATGCTACTTCCCC

TACCTGGAGAACGGATACAACCAGAACTATGGCCGCAAGTTCGTGCAGG

GCAAGAGCATCGATGTGGCCTGCCACCCTGGCTACGCCCTGCCCAAGGC

CCAGACAACTGTGACCTGCATGGAGAATGGTTGGAGCCCCACCCCGCGC

TGCATCCGGGTGTCCTTCACGCTCTGA
```

In some embodiments, the nucleotide sequence encoding FHL1 has at least 75%, 80%, 85%, 90%, 91%, 92%, 93%, 94%, 95%, 96%, 97%, 98% or 99% identity to SEQ ID NO: 12. Preferably, the protein encoded by the nucleotide sequence substantially retains a functional activity of the protein represented by SEQ ID NO: 11.

In other embodiments, the nucleotide sequence encoding FHL1 is SEQ ID NO: 12.

Polynucleotide

Polynucleotides of the invention may comprise DNA or RNA, preferably DNA. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The polynucleotides may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

Structure of the Eye

The medicaments disclosed herein may be delivered to a mammalian, preferably human eye in relation to the treatment or prevention of an eye disease, such as age-related macular degeneration (AMD).

The person skilled in the treatment of diseases of the eye will have a detailed and thorough understanding of the structure of the eye. However, the following structures of particular relevance to the invention are described.

Retina

The retina is the multi-layered membrane, which lines the inner posterior chamber of the eye and senses an image of the visual world which is communicated to the brain via the optic nerve. In order from the inside to the outside of the eye, the retina comprises the layers of the neurosensory retina and retinal pigment epithelium, with the choroid lying outside the retinal pigment epithelium.

Neurosensory Retina and Photoreceptor Cells

The neurosensory retina harbours the photoreceptor cells that directly sense light. It comprises the following layers: internal limiting membrane (ILM); nerve fibre layer; ganglion cell layer; inner plexiform layer; inner nuclear layer; outer plexiform layer; outer nuclear layer (nuclei of the photoreceptors); external limiting membrane (ELM); and photoreceptors (inner and outer segments of the rods and cones).

The skilled person will have a detailed understanding of photoreceptor cells. Briefly, photoreceptor cells are specialised neurons located in the retina that convert light into biological signals. Photoreceptor cells comprise rod and cone cells, which are distributed differently across the retina.

Rod cells are distributed mainly across the outer parts of the retina. They are highly sensitive and provide for vision at low light levels. There are on average about 125 million rod cells in a normal human retina.

Cone cells are found across the retina, but are particularly highly concentrated in the fovea, a pit in the neurosensory retina that is responsible for central high resolution vision. Cone cells are less sensitive than rod cells. There are on average about 6-7 million cone cells in a normal human retina.

Retinal Pigment Epithelium

The retinal pigment epithelium (RPE) is a pigmented layer of cells located immediately to the outside of the neurosensory retina. The RPE performs a number of functions, including transport of nutrients and other substances to the photoreceptor cells, and absorption of scattered light to improve vision.

Choroid

The choroid is the vascular layer situated between the RPE and the outer sclera of the eye. The vasculature of the choroid enables provision of oxygen and nutrients to the retina.

Age-Related Macular Degeneration (AMD)

The clinical progression of age-related macular degeneration (AMD) is characterised in stages according to changes in the macula. The hallmark of early AMD is the appearance of drusen, which are accumulations of extracellular debris underneath the retina and appear as yellow spots in the retina during clinical examination and on fundus photographs. Drusen are categorised by size as small (<63 μm), medium (63-124 μm) and large (>124 μm). They are also considered as hard or soft depending on the appearance of their margins on opthalmological examination. While hard drusen have clearly defined margins, soft drusen have less defined, fluid margins. The Age-related Eye Disease Study (AREDS) fundus photographic severity scale is one of the main classification systems used for this condition.

AMD is classified into "dry" and "wet" (exudative or neovascular) forms. Dry AMD is more common than wet AMD, but the dry form can progress to the wet form, and the two occur simultaneously in a significant number of cases. Dry AMD is typically characterised by progressive apoptosis of cells in the RPE layer, overlying photoreceptor cells, and frequently also the underlying cells in the choroidal capillary layer. Confluent areas of RPE cell death accompanied by overlying photoreceptor atrophy are referred to as geographic atrophy (GA). Patients with this form of AMD experience a slow and progressive deterioration in central vision.

Wet AMD is characterised by bleeding and/or leakage of fluid from abnormal vessels that have grown from the choroidal vessels (choriocapillaris) beneath the RPE and the macula, which can be responsible for sudden and disabling loss of vision. It has been estimated that much of the vision loss that patients experience is due to such choroidal neovascularisation (CNV) and its secondary complications.

The treatment or prevention of AMD described herein may reduce or prevent the appearance of an AMD phenotype described above. Preferably, the treatment of AMD enables maintenance or improvement in visual function.

In some embodiments, the treatment or prevention of AMD results in a prevention of or reduction in the formation of geographic atrophy. In other embodiments, the treatment or prevention of AMD results in slowing the progression of geographic atrophy. For example, it results in an at least 10%, 20%, 30%, 40%, 50%, 60%, 70%, 80% or 90% reduction in the increase in GA area over the 12 months following administration to a treated eye of a subject, relative to an untreated eye over the same period. In other embodiments, the treatment or prevention of AMD results in the treatment of geographic atrophy, for example a reduction in the amount of geographic atrophy.

In some embodiments, the treatment or prevention of AMD results in a prevention of or reduction in the formation of drusen. In other embodiments, the treatment or prevention of AMD results in a reduction in existing drusen, for example a reduction in the size and/or number of existing drusen.

In some embodiments, the treatment or prevention of AMD results in a prevention of or reduction in complement deposition. In other embodiments, the treatment or prevention of AMD results in a reduction in existing complement deposition.

In some embodiments, the treatment or prevention of AMD results in an improvement in or restoration of vision or visual acuity. In other embodiments, the treatment or prevention of AMD mitigates the loss of vision or visual acuity.

In some embodiments, the treatment or prevention of AMD results in an improvement in or restoration of reading speed in a subject. In other embodiments, the treatment or prevention of AMD mitigates the reduction in reading speed in a subject.

In some embodiments, the treatment or prevention of AMD results in a reduction or prevention of loss of photoreceptors and/or the retinal pigment epithelium (RPE).

Diabetic Retinopathy

Diabetic retinopathy is a condition characterised by damage to the blood vessels of the retina, which is caused by the high blood sugar levels associated with diabetes. If left untreated, diabetic retinopathy can cause blindness.

Although subjects with mild diabetic retinopathy may have good vision, two types of diabetic retinopathy, namely diabetic macular oedema (DMO) and proliferative diabetic retinopathy (PDR) may threaten the sight of the subject.

Diabetic macular oedema is characterised by the leakage of fluid from the damaged blood vessels in the back of the eye. The leaked fluid accumulates in the macula, which leads to swelling and blurred vision. This can eventually give rise to poor central vision and an inability to read or drive. Side vision usually remains normal.

Proliferative diabetic retinopathy is characterised by the closure of retinal blood vessels, leading to the growth of abnormal, fragile blood vessels on the surface of the retina. This may result in permanent loss of vision due to bleeding into the eye, scarring and retinal detachment.

Vectors

A vector is a tool that allows or facilitates the transfer of an entity from one environment to another.

Adeno-Associated Viral (AAV) Vectors

In one aspect, the invention provides an AAV vector comprising a polynucleotide of the invention.

Preferably, the AAV vector is in the form of an AAV vector particle.

Methods of preparing and modifying viral vectors and viral vector particles, such as those derived from AAV, are well known in the art.

The AAV vector may comprise an AAV genome or a fragment or derivative thereof.

AAV is known to be capable of packaging genomes up to 5.2 kb in size (Dong, J.-Y. et al. (1996) Human Gene Therapy 7:2101-2112).

An AAV genome is a polynucleotide sequence, which may encode functions needed for production of an AAV particle. These functions include those operating in the replication and packaging cycle of AAV in a host cell, including encapsidation of the AAV genome into an AAV particle. Naturally occurring AAVs are replication-deficient and rely on the provision of helper functions in trans for completion of a replication and packaging cycle. Accordingly, the AAV genome of the AAV vector of the invention is typically replication-deficient.

The AAV genome may be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype, isolate or clade of AAV. Thus, the AAV genome may be the full genome of a naturally occurring AAV. As is known to the skilled person, AAVs occurring in nature may be classified according to various biological systems.

Commonly, AAVs are referred to in terms of their serotype. A serotype corresponds to a variant subspecies of AAV which, owing to its profile of expression of capsid surface antigens, has a distinctive reactivity which can be used to distinguish it from other variant subspecies. Typically, a virus having a particular AAV serotype does not efficiently cross-react with neutralising antibodies specific for any other AAV serotype.

AAV serotypes include AAV1, AAV2, AAV3, AAV4, AAV5, AAV6, AAV7, AAV8, AAV9, AAV10 and AAV11, and also recombinant serotypes, such as Rec2 and Rec3, recently identified from primate brain. Any of these AAV serotypes may be used in the invention.

In some embodiments, the AAV vector particle is an AAV1, AAV2, AAV3, AAV4, AAV5, AAV6, AAV7, AAV8, AAV9, AAV10, AAV11, Rec2 or Rec3 AAV vector particle.

In some embodiments, the AAV may be an AAV1, AAV2, AAV5, AAV7 or AAV8 serotype.

In some embodiments, the AAV may be an AAV2 or AAV8 serotype.

In some embodiments, the AAV may be an AAV2 serotype. In other embodiments, the AAV may be an AAV8 serotype.

The capsid protein may be a mutant capsid protein such as disclosed in WO 2008/124724, which is hereby incorporated by reference.

In some embodiments, the AAV vector comprises an AAV8 capsid with an Y733F mutation.

Reviews of AAV serotypes may be found in Choi et al. (2005) Curr. Gene Ther. 5:299-310 and Wu et al. (2006) Molecular Therapy 14:316-27. The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV may also be referred to in terms of clades or clones. This refers to the phylogenetic relationship of naturally derived AAVs, and typically to a phylogenetic group of AAVs which can be traced back to a common ancestor, and includes all descendants thereof. Additionally, AAVs may be referred to in terms of a specific isolate, i.e. a genetic isolate of a specific AAV found in nature. The term genetic isolate describes a population of AAVs which has undergone limited genetic mixing with other naturally occurring AAVs, thereby defining a recognisably distinct population at a genetic level.

The skilled person can select an appropriate serotype, clade, clone or isolate of AAV for use in the invention on the basis of their common general knowledge. For instance, the AAV5 capsid has been shown to transduce primate cone photoreceptors efficiently as evidenced by the successful correction of an inherited colour vision defect (Mancuso et al. (2009) Nature 461:784-7).

The AAV serotype determines the tissue specificity of infection (or tropism) of an AAV. Accordingly, preferred AAV serotypes for use in AAVs administered to patients in accordance with the invention are those which have natural tropism for or a high efficiency of infection of target cells within the eye. In some embodiments, AAV serotypes for use in the invention are those which transduce cells of the neurosensory retina, retinal pigment epithelium and/or choroid.

Typically, the AAV genome of a naturally derived serotype, isolate or clade of AAV comprises at least one inverted terminal repeat sequence (ITR). An ITR sequence acts in cis to provide a functional origin of replication and allows for integration and excision of the vector from the genome of a cell. In preferred embodiments, one or more ITR sequences flank the nucleotide sequences encoding the Complement Factor I or FHL1. The AAV genome typically also comprises packaging genes, such as rep and/or cap genes which encode packaging functions for an AAV particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV particle. Capsid variants are discussed below.

A promoter will be operably linked to each of the packaging genes. Specific examples of such promoters include the p5, p19 and p40 promoters (Laughlin et al. (1979) Proc. Natl. Acad. Sci. USA 76:5567-5571). For example, the p5 and p19 promoters are generally used to express the rep gene, while the p40 promoter is generally used to express the cap gene.

As discussed above, the AAV genome used in the AAV vector of the invention may therefore be the full genome of a naturally occurring AAV. For example, a vector comprising a full AAV genome may be used to prepare an AAV vector or vector particle in vitro. However, while such a vector may in principle be administered to patients, this will rarely be done in practice. Preferably, the AAV genome will be derivatised for the purpose of administration to patients. Such derivatisation is standard in the art and the invention encompasses the use of any known derivative of an AAV genome, and derivatives which could be generated by applying techniques known in the art. Derivatisation of the AAV genome and of the AAV capsid are reviewed in Coura and Nardi (2007) Virology Journal 4:99, and in Choi et al. and Wu et al., referenced above.

Derivatives of an AAV genome include any truncated or modified forms of an AAV genome which allow for expression of a transgene from an AAV vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences, i.e. a self-complementary AAV genome. This allows for bypass of DNA replication in the target cell, and so enables accelerated transgene expression.

The one or more ITRs will preferably flank the nucleotide sequence encoding the Complement Factor I or FHL1 at either end. The inclusion of one or more ITRs is preferred to aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo.

In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

The following portions could therefore be removed in a derivative of the invention: one inverted terminal repeat (ITR) sequence, the replication (rep) and capsid (cap) genes. However, in some embodiments, derivatives may additionally include one or more rep and/or cap genes or other viral sequences of an AAV genome. Naturally occurring AAV integrates with a high frequency at a specific site on human chromosome 19, and shows a negligible frequency of random integration, such that retention of an integrative capacity in the vector may be tolerated in a therapeutic setting.

Where a derivative comprises capsid proteins i.e. VP1, VP2 and/or VP3, the derivative may be a chimeric, shuffled or capsid-modified derivative of one or more naturally occurring AAVs. In particular, the invention encompasses the provision of capsid protein sequences from different serotypes, clades, clones, or isolates of AAV within the same vector (i.e. a pseudotyped vector).

Chimeric, shuffled or capsid-modified derivatives will be typically selected to provide one or more desired functionalities for the AAV vector. Thus, these derivatives may display increased efficiency of gene delivery, decreased immunogenicity (humoral or cellular), an altered tropism range and/or improved targeting of a particular cell type compared to an AAV vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are co-transfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. An example might include the use of RGD peptide to block uptake in the retinal pigment epithelium and thereby enhance transduction of surrounding retinal tissues (Cronin et al. (2008) ARVO Abstract: D1048). The unrelated protein may also be one which assists purification of the viral particle as part of the production process, i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al., referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The AAV vector of the invention may take the form of a nucleotide sequence comprising an AAV genome or derivative thereof and a sequence encoding the Complement Factor I or FHL1 transgene or derivatives thereof.

The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral capsid. The AAV particle also includes chemically modified forms bearing ligands adsorbed to the capsid surface. For example, such ligands may include antibodies for targeting a particular cell surface receptor.

Thus, for example, the AAV particles of the invention include those with an AAV2 genome and AAV2 capsid proteins (AAV2/2), those with an AAV2 genome and AAV5 capsid proteins (AAV2/5) and those with an AAV2 genome and AAV8 capsid proteins (AAV2/8), as well as those with an AAV2 genome and capsid proteins of more than one serotype.

The AAV vector may comprise multiple copies (e.g., 2, 3 etc.) of the nucleotide sequence referred to herein.

Promoters and Regulatory Sequences

The polynucleotide or vector of the invention may also include elements allowing for the expression of the Complement Factor I or FHL1 transgenes in vitro or in vivo. These may be referred to as expression control sequences. Thus, the polynucleotide or vector typically comprises expression control sequences (e.g. comprising a promoter sequence) operably linked to the nucleotide sequence encoding the transgene.

Any suitable promoter may be used, the selection of which may be readily made by the skilled person. The promoter sequence may be constitutively active (i.e. operational in any host cell background), or alternatively may be active only in a specific host cell environment, thus allowing for targeted expression of the transgene in a particular cell type (e.g. a tissue-specific promoter). The promoter may show inducible expression in response to presence of another factor, for example a factor present in a host cell. In any event, where the vector is administered for therapy, it is preferred that the promoter should be functional in the target cell background.

In some embodiments, it is preferred that the promoter shows retinal-cell specific expression in order to allow for the transgene to only be expressed in retinal cell populations. Thus, expression from the promoter may be retinal-cell specific, for example confined only to cells of the neuro-sensory retina and retinal pigment epithelium.

Preferred promoters, which are not retinal-cell specific, include the chicken beta-actin (CBA) promoter, optionally in combination with a cytomegalovirus (CMV) enhancer element. An example promoter for use in the invention is a CAG promoter, for example the promoter used in the rAVE expression cassette (GeneDetect.com).

In preferred embodiments, the polynucleotide or vector comprises a CMV promoter.

An example CMV promoter sequence is:

```
                                    (SEQ ID NO: 13)
GGAGTTCCGCGTTACATAACTTACGGTAAATGGCCCGCCTGGCTGACCG

CCCAACGACCCCCGCCCATTGACGTCAATAATGACGTATGTTCCCATAG

TAACGCCAATAGGGACTTTCCATTGACGTCAATGGGTGGAGTATTTACG

GTAAACTGCCCACTTGGCAGTACATCAAGTGTATCATATGCCAAGTACG

CCCCCTATTGACGTCAATGACGGTAAATGGCCCGCCTGGCATTATGCCC

AGTACATGACCTTATGGGACTTTCCTACTTGGCAGTACATCTACGTATT

AGTCATCGCTATTACCATGGTGATGCGGTTTTGGCAGTACATCAATGGG

CGTGGATAGCGGTTTGACTCACGGGGATTTCCAAGTCTCCACCCCATTG

ACGTCAATGGGAGTTTGTTTTGGCACCAAAATCAACGGGACTTTCCAAA

ATGTCGTAACAACTCCGCCCCATTGACGCAAATGGGCGGTAGGCGTGTA

CGGTGGGAGGTCTATATAAGCAGAGCTCGTTTAGTGAACCGTCAGATCG

CCTGGAGACGCCATCCACGCTGTTTTGACCTCCATAGAAGACACCG
```

In some embodiments, the polynucleotide or vector comprises a promoter with a nucleotide sequence that has at least 75%, 80%, 85% 90%, 95%, 96%, 97%, 98% or 99% identity to SEQ ID NO: 13. Preferably, wherein the nucleotide sequence substantially retains the functional activity of the promoter represented by SEQ ID NO: 13.

In other embodiments, the polynucleotide or vector comprises a promoter with the nucleotide sequence of SEQ ID NO: 13.

A further example promoter sequence is:

```
                                    (SEQ ID NO: 5)
ATTGACGTCAATAATGACGTATGTTCCCATAGTAACGCCAATAGGGACT

TTCCATTGACGTCAATGGGTGGAGTATTTACGGTAAACTGCCCACTTGG

CAGTACATCAAGTGTATCATATGCCAAGTACGCCCCCTATTGACGTCAA

TGACGGTAAATGGCCCGCCTGGCATTATGCCCAGTACATGACCTTATGG

GACTTTCCTACTTGGCAGTACATCTACGTATTAGTCATCGCTATTACCA

TGGTCGAGGTGAGCCCCACGTTCTGCTTCACTCTCCCCATCTCCCCCCC

CTCCCCACCCCCAATTTTGTATTTATTTATTTTTTAATTATTTTGTGCA

GCGATGGGGGGGGGGGGGGGGGGGGGGCGGCGCGCCAGGCGGGGGGGGC

GGGGCGAGGGGCGGGGCGGGGCGAGGCGGAGAGGTGCGGCGGCAGCCAA

TCAGAGCGGCGCGCTCCGAAAGTTTCCTTTTATGGCGAGGCGGCGGCGG

CGGCGGCCCTATAAAAAGCGAAGCGCGCGGCGGGCGGGAGTCGCTGCGC

GCTGCCTTCGCCCCGTGCCCCGCTCCGCCGCCGCCTCGCGCCGCCCGCC

CCGGCTCTGACTGACCGCGTTACTCCCACAGGTGAGCGGGCGGGACGGC

CCTTCTCCTCCGGGCTGTAATTAGCGCTTGGTTTAATGACGGCTTGTTT

CTTTTCTGTGGCTGCGTGAAAGCCTTGAGGGGCTCCGGGAGGGCCCTTT

GTGCGGGGGGAGCGGCTCGGGGCTGTCCGCGGGGGGACGGCTGCCTTCG

GGGGGGACGGGGCAGGGCGGGGTTCGGCTTCTGGCGTGTGACCGGCGGC

TCTAGAGCCTCTGCTAACCATGTTCATGCCTTCTTCTTTTTCCTACAGC

TCCTGGGCAACGTGCTGGTTATTGTGCTGTCTCATCATTTTGGCAAAGA

ATT
```

In some embodiments, the polynucleotide or vector comprises a promoter with a nucleotide sequence that has at least 75%, 80%, 85% 90%, 95%, 96%, 97%, 98% or 99% identity to SEQ ID NO: 5. Preferably, wherein the nucleotide sequence substantially retains the functional activity of the promoter represented by SEQ ID NO: 5.

In other embodiments, the polynucleotide or vector comprises a promoter with the nucleotide sequence of SEQ ID NO: 5.

Examples of promoters based on human sequences that would induce retina-specific gene expression include rhodopsin kinase for rods and cones (Allocca et al. (2007) J. Virol. 81:11372-80), PR2.1 for cones only (Mancuso et al. (2009) Nature 461:784-7) and/or RPE65 (Bainbridge et al. (2008) N. Engl. J. Med. 358:2231-9) or VMD2 (Esumi et al. (2004) J. Biol. Chem. 279:19064-73) for the retinal pigment epithelium.

The polynucleotide or vector of the invention may also comprise one or more additional regulatory sequences which may act pre- or post-transcriptionally. The regulatory sequence may be part of the native transgene locus or may be a heterologous regulatory sequence. The polynucleotide or vector of the invention may comprise portions of the 5'-UTR or 3'-UTR from the native transgene transcript.

Regulatory sequences are any sequences which facilitate expression of the transgene, i.e. act to increase expression of a transcript, improve nuclear export of mRNA or enhance its stability. Such regulatory sequences include for example enhancer elements, post-transcriptional regulatory elements and polyadenylation sites.

A preferred polyadenylation site is the Bovine Growth Hormone poly-A (bGH poly-A) signal.

An example Bovine Growth Hormone poly-A (bGH poly-A) signal is:

```
                                          (SEQ ID NO: 14)
GTGCCTTCTAGTTGCCAGCCATCTGTTGTTTGCCCCTCCCCCGTGCCTT

CCTTGACCCTGGAAGGTGCCACTCCCACTGTCCTTTCCTAATAAAATGA

GGAAATTGCATCGCATTGTCTGAGTAGGTGTCATTCTATTCTGGGGGGT

GGGGTGGGGCAGGACAGCAAGGGGGAGGATTGGGAAGACAATAGCAGGC

ATGCTGGGGATGCGGTGGGCTCTATGG
```

A further example Bovine Growth Hormone poly-A (bGH poly-A) signal is:

```
                                          (SEQ ID NO: 6)
TCGCTGATCAGCCTCGACTGTGCCTTCTAGTTGCCAGCCATCTGTTGTT

TGCCCCTCCCCCGTGCCTTCCTTGACCCTGGAAGGTGCCACTCCCACTG

TCCTTTCCTAATAAAATGAGGAAATTGCATCGCATTGTCTGAGTAGGTG

TCATTCTATTCTGGGGGGTGGGGTGGGGCAGGACAGCAAGGGGGAGGAT

TGGGAAGACAATAGCAGGCATGCTGGGGATGCGGTGGGCTCTATGGCTT

CTGAGGCGGAAAGAACCAGCTGGGG
```

In some embodiments, the polynucleotide or vector comprises a polyadenylation signal with a nucleotide sequence that has at least 75%, 80%, 85%, 90%, 95%, 96%, 97%, 98% or 99% identity to SEQ ID NO: 14 or 6. Preferably, wherein the nucleotide sequence substantially retains the functional activity of the polyadenylation signal represented by SEQ ID NO: 14 or 6.

In other embodiments, the polynucleotide or vector comprises a polyadenylation signal with the nucleotide sequence of SEQ ID NO: 14 or 6.

In the context of the polynucleotide or vector of the invention, such regulatory sequences will be cis-acting. However, the invention also encompasses the use of trans-acting regulatory sequences located on additional genetic constructs.

A preferred post-transcriptional regulatory element for use in a AAV vector of the invention is the woodchuck hepatitis post-transcriptional regulatory element (WPRE) or a variant thereof.

An example WPRE is:

```
                                          (SEQ ID NO: 7)
ATCAACCTCTGGATTACAAAATTTGTGAAAGATTGACTGGTATTCTTAA

CTATGTTGCTCCTTTTACGCTATGTGGATACGCTGCTTTAATGCCTTTG

TATCATGCTATTGCTTCCCGTATGGCTTTCATTTTCTCCTCCTTGTATA

AATCCTGGTTGCTGTCTCTTTATGAGGAGTTGTGGCCCGTTGTCAGGCA

ACGTGGCGTGGTGTGCACTGTGTTTGCTGACGCAACCCCCACTGGTTGG

GGCATTGCCACCACCTGTCAGCTCCTTTCCGGGACTTTCGCTTTCCCCC

TCCCTATTGCCACGGCGGAACTCATCGCCGCCTGCCTTGCCCGCTGCTG

GACAGGGGCTCGGCTGTTGGGCACTGACAATTCCGTGGTGTTGTCGGGG

AAATCATCGTCCTTTCCTTGGCTGCTCGCCTGTGTTGCCACCTGGATTC
```

```
-continued
TGCGCGGGACGTCCTTCTGCTACGTCCCTTCGGCCCTCAATCCAGCGGA

CCTTCCTTCCCGCGGCCTGCTGCCGGCTCTGCGGCCTCTTCCGCGTCTT

CGCCTTCGCCCTCAGACGAGTCGGATCTCCCTTTGGGCCGCCTCCCCGC
```

WPRE is a tripartite element containing gamma, alpha and beta elements, in the given order. A shortened version of WPRE, which contains only minimal gamma and alpha elements (referred to as WPRE3; Choi, J.-H. et al. (2014) Molecular Brain 7:17), may also be used in the invention.

An example WPRE3 sequence is:

```
(SEQ ID NO: 15)
AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTAGTTCTTGCCACGGCGGAACTCATCGCCGCCTGCCTTG

CCCGCTGCTGGACAGGGGCTCGGCTGTTGGGCACTGACAATTCCGTGGT
```

In some embodiments, the polynucleotide or vector comprises a post-transcriptional regulatory element with a nucleotide sequence that has at least 75%, 80%, 85%, 90%, 95%, 96%, 97%, 98% or 99% identity to SEQ ID NO: 15 or 7. Preferably, wherein the nucleotide sequence substantially retains the functional activity of the post-transcriptional regulatory element represented by SEQ ID NO: 15 or 7.

In other embodiments, the polynucleotide or vector comprises a post-transcriptional regulatory element with the nucleotide sequence of SEQ ID NO: 15 or 7.

Another regulatory sequence which may be used in a polynucleotide or vector of the invention is a scaffold-attachment region (SAR). Additional regulatory sequences may be readily selected by the skilled person.

Method of Administration

The polynucleotide or vector of the invention may be administered systemically (for example by peripheral vein infusion) and may be administered locally (for example to the CNS system by intrathecal injection). In preferred embodiments, the polynucleotide or vector is administered intraocularly.

The term "intraocular" refers to the interior of the eye, thus intraocular administration relates to the administration to the interior of the eye of a subject In some embodiments, the polynucleotide or vector is administered to the eye of a subject by subretinal, direct retinal, suprachoroidal or intravitreal injection. In some embodiments, said administration is performed by a robot.

The volume of the medicament composition injected may, for example, be about 10-500 µL, for example about 50-500, 100-500, 200-500, 300-500, 400-500, 50-250, 100-250, 200-250 or 50-150 µL. The volume may, for example, be about 10, 50, 100, 150, 200, 250, 300, 350, 400, 450 or 500 µL. Preferably, the volume of the medicament composition injected is 100 µL.

The skilled person will be familiar with and well able to carry out individual subretinal, direct retinal, suprachoroidal or intravitreal injections.

Preferably, the polynucleotide or vector is administered by subretinal injection.

In some embodiments, the polynucleotide, vector or pharmaceutical composition comprising the same is administered not more than once, or not more than twice, during the lifetime of a subject.

Subretinal Injection

Subretinal injections are injections into the subretinal space, i.e. underneath the neurosensory retina. During a subretinal injection, the injected material is directed into, and creates a space between, the photoreceptor cell and retinal pigment epithelial (RPE) layers.

When the injection is carried out through a small retinotomy, a retinal detachment may be created. The detached, raised layer of the retina that is generated by the injected material is referred to as a "bleb".

The hole created by the subretinal injection must be sufficiently small that the injected solution does not significantly reflux back into the vitreous cavity after administration. Such reflux would be particularly problematic when a medicament is injected, because the effects of the medicament would be directed away from the target zone. Preferably, the injection creates a self-sealing entry point in the neurosensory retina, i.e. once the injection needle is removed, the hole created by the needle reseals such that very little or substantially no injected material is released through the hole.

To facilitate this process, specialist subretinal injection needles are commercially available (e.g. DORC 41G Teflon subretinal injection needle, Dutch Ophthalmic Research Center International BV, Zuidland, The Netherlands). These are needles designed to carry out subretinal injections.

Unless damage to the retina occurs during the injection, and as long as a sufficiently small needle is used, substantially all injected material remains localised between the detached neurosensory retina and the RPE at the site of the localised retinal detachment (i.e. does not reflux into the vitreous cavity). Indeed, the typical persistence of the bleb over a short time frame indicates that there is usually little escape of the injected material into the vitreous. The bleb may dissipate over a longer time frame as the injected material is absorbed.

Visualisations of the eye, in particular the retina, for example using optical coherence tomography, may be made pre-operatively.

The volume of the medicament composition injected may, for example, be about 10-500 μL, for example about 50-500, 100-500, 200-500, 300-500, 400-500, 50-250, 100-250, 200-250 or 50-150 μL. The volume may, for example, be about 10, 50, 100, 150, 200, 250, 300, 350, 400, 450 or 500 μL. Preferably, the volume of the medicament composition injected is 100 μL. Larger volumes may increase the risk of stretching the retina, while smaller volumes may be difficult to see.

Two-Step Subretinal Injection

The polynucleotide or vector of the invention may be delivered with increased accuracy and safety by using a two-step method in which a localised retinal detachment is created by the subretinal injection of a first solution. The first solution does not comprise the polynucleotide or vector. A second subretinal injection is then used to deliver the medicament comprising the polynucleotide or vector into the subretinal fluid of the bleb created by the first subretinal injection. Because the injection delivering the medicament is not being used to detach the retina, a specific volume of solution may be injected in this second step.

In some embodiments, the subretinal injection of the vector comprises the steps:

(a) administering a solution to the subject by subretinal injection in an amount effective to at least partially detach the retina to form a subretinal bleb, wherein the solution does not comprise the polynucleotide or vector; and (b) administering a medicament composition by subretinal injection into the bleb formed by step (a), wherein the medicament comprises the polynucleotide or vector.

The volume of solution injected in step (a) to at least partially detach the retina may be, for example, about 10-1000 μL, for example about 50-1000, 100-1000, 250-1000, 500-1000, 10-500, 50-500, 100-500, 250-500 μL. The volume may be, for example, about 10, 50, 100, 200, 300, 400, 500, 600, 700, 800, 900 or 1000 μL.

The volume of the medicament composition injected in step (b) may be, for example, about 10-500 μL, for example about 50-500, 100-500, 200-500, 300-500, 400-500, 50-250, 100-250, 200-250 or 50-150 μL. The volume may be, for example, about 10, 50, 100, 150, 200, 250, 300, 350, 400, 450 or 500 μL. Preferably, the volume of the medicament composition injected in step (b) is 100 μL. Larger volumes may increase the risk of stretching the retina, while smaller volumes may be difficult to see.

The solution that does not comprise the medicament (i.e. the "solution" of step (a)) may be similarly formulated to the solution that does comprise the medicament, as described below. A preferred solution that does not comprise the medicament is balanced saline solution (BSS) or a similar buffer solution matched to the pH and osmolality of the subretinal space.

Visualising the Retina During Surgery

Under certain circumstances, for example during end-stage retinal degenerations, identifying the retina is difficult because it is thin, transparent and difficult to see against the disrupted and heavily pigmented epithelium on which it sits. The use of a blue vital dye (e.g. Brilliant Peel®, Geuder; MembraneBlue-Dual®, Dorc) may facilitate the identification of the retinal hole made for the retinal detachment procedure (i.e. step (a) in the two-step subretinal injection method of the invention) so that the medicament can be administered through the same hole without the risk of reflux back into the vitreous cavity.

The use of the blue vital dye also identifies any regions of the retina where there is a thickened internal limiting membrane or epiretinal membrane, as injection through either of these structures would hinder clean access into the subretinal space. Furthermore, contraction of either of these structures in the immediate post-operative period could lead to stretching of the retinal entry hole, which could lead to reflux of the medicament into the vitreous cavity.

Suprachoroidal Injection

The polynucleotide or vector of the invention may be delivered to the suprachoroidal space using an ab externo approach that utilises an microcatheter (see, for example, Peden et al. (2011) PLOS One 6 (2): e17140). In this method a limbal conjunctival peritomy is performed to expose bare sclera, followed by sclerotomy to expose bare choroid. A microcatheter (such as the iTrack 250A from iScience Interventional, optionally connected to an illumination system such as the iLumin laser-diode based micro-illumination system (iScience Interventional)) is introduced into the suprachoroidal space and advanced posteriorly towards the optic disc. Following manipulation of the microcatheter tip into the desired position, injection of the polynucleotide or vector forms a bleb within the retina and choroid.

Thus, in some embodiments, the polynucleotide or vector is delivered suprachoroidally by a method comprising (i) introduction of a microcatheter into the suprachoroidal space; (ii) advancing the microcatheter within said space until the tip is in the proximity of the afflicted region of the retina; and (iii) injecting the polynucleotide or vector from the microcatheter tip to create a bleb.

In some embodiments, the above administration procedures are directly carried out by a robot.

Pharmaceutical Compositions and Injected Solutions

The medicaments, for example polynucleotides or vectors, of the invention may be formulated into pharmaceutical compositions. These compositions may comprise, in addition to the medicament, a pharmaceutically acceptable carrier, diluent, excipient, buffer, stabiliser or other materials well known in the art. Such materials should be non-toxic and should not interfere with the efficacy of the active ingredient. The precise nature of the carrier or other material may be determined by the skilled person according to the route of administration, e.g. subretinal, direct retinal, suprachoroidal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution, or glycols such as ethylene glycol, propylene glycol or polyethylene glycol may be included. In some cases, a surfactant, such as pluronic acid (PF68) 0.001% may be used.

For injection at the site of affliction, the active ingredient may be in the form of an aqueous solution which is pyrogen-free, and has suitable pH, isotonicity and stability. The skilled person is well able to prepare suitable solutions using, for example, isotonic vehicles such as Sodium Chloride Injection, Ringer's Injection or Lactated Ringer's Injection. Preservatives, stabilisers, buffers, antioxidants and/or other additives may be included as required.

For delayed release, the medicament may be included in a pharmaceutical composition which is formulated for slow release, such as in microcapsules formed from biocompatible polymers or in liposomal carrier systems according to methods known in the art.

Method of Treatment

It is to be appreciated that all references herein to treatment include curative, palliative and prophylactic treatment; although in the context of the invention references to preventing are more commonly associated with prophylactic treatment. Treatment may also include arresting progression in the severity of a disease.

The treatment of mammals, particularly humans, is preferred. However, both human and veterinary treatments are within the scope of the invention.

Variants, Derivatives, Analogues, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is –12 for a gap and –4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12:387). Examples of other software that can perform sequence comparisons include, but are not limited to, the BLAST package (see Ausubel et al. (1999) ibid-Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174:247-50; FEMS Microbiol. Lett. (1999) 177:187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" of full length Complement Factor I or FHL1 are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

Codon Optimisation

Nucleotide sequences encoding Complement Factor I (CFI) and Complement Factor H-like Protein 1 (FHL1) were codon optimised using a range of approaches summarised in Table 1.

TABLE 1

| RC number | Transgene | Codon Optimisation Tool | Basic or manually edited | Size of AAV |
|---|---|---|---|---|
| RC128 | CFI | GeneArt (ThermoFisher) | Basic | 3948 bp |
| RC129 | CFI | GeneArt (ThermoFisher) | Manually edited | 3948 bp |
| RC130 | CFI | GenScript | Basic | 3948 bp |
| RC131 | CFI | GenScript | Manually edited | 3948 bp |
| RC132 | CFI | IDT | Basic | 3948 bp |
| RC133 | CFI | IDT | Manually edited | 3948 bp |
| RC134 | CFI | JCat | Basic | 3948 bp |
| RC135 | CFI | JCat | Manually edited | 3948 bp |
| RC136 | CFI | COOL | Basic | 3948 bp |
| RC137 | CFI | COOL | Manually edited | 3948 bp |
| RC138 | FHL-1 | GeneArt (ThermoFisher) | Basic | 3546 bp |
| RC139 | FHL-1 | GeneArt (ThermoFisher) | Manually edited | 3546 bp |
| RC140 | FHL-1 | GenScript | Basic | 3546 bp |
| RC141 | FHL-1 | GenScript | Manually edited | 3546 bp |
| RC142 | FHL-1 | IDT | Basic | 3546 bp |
| RC143 | FHL-1 | IDT | Manually edited | 3546 bp |
| RC144 | FHL-1 | JCat | Basic | 3546 bp |
| RC145 | FHL-1 | JCat | Manually edited | 3546 bp |
| RC146 | FHL-1 | COOL | Basic | 3546 bp |
| RC147 | FHL-1 | COOL | Manually edited | 3546 bp |

For the "basic" codon optimisation, the sequence of CFI or FHL-1 was entered into 5 online codon optimisation tools:

1. GeneArt (thermofisher.com/uk/en/home/life-science/cloning/gene-synthesis/geneart-gene-synthesis/gene-optimizer.html)
2. GenScript (genscript.com/quick_order/gene_services-_gene_synthesis)
3. IDT (eu.idtdna.com/CodonOpt)
4. JCat (jcat.de/)
5. COOL
   (cool.syncti.org/setup_input_sequence_create_wf1.php?=Start+Using+Codon+Optimization+On-Line+% 3E %3E %3E)

The standard human genetic code was used for all tools.

For tools 1-4 above, one sequence was generated from each tool.

For tool 5, default settings were used and the target expression host was set to *Homo sapiens*. In addition, 39 genes that are highly expressed in the RPE (Table 2) were input into the tool (based on Table 4 of Booij, J. C. et al. (2010) PLOS One 5: e9341).

TABLE 2

| Gene symbol | Genbank ID | HUGO |
|---|---|---|
| C6orf105 | NM_032744 | ADTRP |
| BEST1 | NM_004183 | BEST1 |
| TMEM27 | NM_020665 | TMEM27 |
| LRP8 | NM_004631 | LRP8 |
| LGI1 | NM 005097 | LGI1 |
| FAM40B | AB032996 | STRIP2 |
| ERMN | AB033015 | ERMN |
| LRAT | NM_004744 | LRAT |
| RLBP1 | NM_000326 | RLBP1 |
| DUSP6 | NM_001946 | DUSP6 |
| RBP1 | NM_002899 | RBP1 |
| SLC16A3 | NM 004207 | SLC16A3 |
| WFDC1 | NM 021197 | WFDC1 |
| KIAA0953 | AF131834 | EFR3B |
| CA14 | NM_012113 | CA14 |

TABLE 2-continued

| Gene symbol | Genbank ID | HUGO |
|---|---|---|
| RGR | NM 002921 | RGR |
| STRA6 | NM_022369 | STRA6 |
| RDH5 | NM 002905 | RDH5 |
| BMP4 | NM 001202 | BMP4 |
| CXCL14 | NM_004887 | CXCL14 |
| LHX2 | NM_004789 | LHX2 |
| C1QTNF5 | NM_015645 | C1QTNF5 |
| SLC6A20 | NM_020208 | SLC6A20 |
| SLC16A8 | NM_013356 | SLC16A8 |
| CDH3 | NM_001793 | CDH3 |
| FRZB | NM_001463 | FRZB |
| SERPINF1 | NM_002615 | SERPINF1 |
| SPOCK1 | NM_004598 | SPOCK1 |
| LMO1 | NM_002315 | LMO1 |
| RDH11 | NM_016026 | RDH11 |
| SFRP5 | NM_003015 | SFRP5 |
| SGK1 | NM_005627 | SGK1 |
| KRT18 | NM_000224 | KRT18 |
| EZR | NM_003379 | EZR |
| DHCR7 | NM_001360 | DHCR7 |
| ITGAV | NM_002210 | ITGAV |
| GALNT11 | NM_022087 | GALNT11 |
| PCP4 | NM_006198 | PCP4 |
| BASP1 | NM_006317 | BASP1 |

Tool 5 generated 70 optimised sequences for CFI and 55 for FHL-1, the top ranking sequence was used.

For the "manual" codon optimisation, the five basic CFI and FHL-1 codon optimised sequences generated above were subjected to manual optimisation to eliminate cryptic splice sites, microRNA binding sites, to remove tandem duplicate codons and to check GC content.

Cryptic Splice Site Removal

Cryptic splice sites were identified using the Fruitfly.org tool. A cut-off value of 0.4 was used for analysis, but only sequences scoring >0.75 were modified.

Splice sites were removed by changing the GT of the donor site or the AG of the acceptor site wherever possible. When not possible (e.g. for sequences encoding valine), the 5' adjacent base was changed.

All modified sequences were then analysed with Fruitfly.org tool to confirm that all splice sites had either been removed or reduced to below the 0.75 threshold.

MicroRNA Binding Site Removal

MicroRNAs were identified using the Genecards.org tool.

For CFI, the following miRNA binding sites were identified: hsa-mir-335-5p, hsa-mir-181a-5p, hsa-mir-26b-5p.

For FHL-1, the following miRNA binding sites were identified (based on the sequence of Complement Factor H, CFH): hsa-mir-146a-5p.

Each codon optimised sequence (after splice site removal if necessary) was then passed through the STarMir tool (sfold.wadsworth.org/cgi-bin/starmirtest2.pl) to see if the miRNA sites were still present. Any miRNA sites the were identified with a logistical probability of >0.75 were modified.

Tandem Duplicate Codon Removal

All sequences were manually checked for tandem duplicate codons. Where these were found, the second codon was changed to the next most commonly used codon in *Homo sapiens* (using the SnapGene codon usage table).

The wild type and codon optimised sequences are detailed below:

GT005: CFI wild type sequence:

(SEQ ID NO: 16)

ATGAAGCTTCTTCATGTTTTCCTGTTATTTCTGTGCTTCCACTTAAGGTTTTGCAAGGTCACTTATACATCT

CAAGAGGATCTGGTGGAGAAAAAGTGCTTAGCAAAAAAATATACTCACCTCTCCTGCGATAAAGTCTTCTGC

CAGCCATGGCAGAGATGCATTGAGGGCACCTGTGTTTGTAAACTACCGTATCAGTGCCCAAAGAATGGCACT

GCAGTGTGTGCAACTAACAGGAGAAGCTTCCCAACATACTGTCAACAAAGAGTTTGGAATGTCTTCATCCA

GGGACAAAGTTTTTAAATAACGGAACATGCACAGCCGAAGGAAAGTTTAGTGTTTCCTTGAAGCATGGAAAT

ACAGATTCAGAGGGAATAGTTGAAGTAAAACTTGTGGACCAAGATAAGACAATGTTCATATGCAAAAGCAGC

TGGAGCATGAGGGAAGCCAACGTGGCCTGCCTTGACCTTGGGTTTCAACAAGGTGCTGATACTCAAAGAAGG

TTTAAGTTGTCTGATCTCTCTATAAATTCCACTGAATGTCTACATGTGCATTGCCGAGGATTAGAGACCAGT

TTGGCTGAATGTACTTTTACTAAGAGAAGAACTATGGGTTACCAGGATTTCGCTGATGTGGTTTGTTATACA

CAGAAAGCAGATTCTCCAATGGATGACTTCTTTCAGTGTGTGAATGGGAAATACATTTCTCAGATGAAAGCC

TGTGATGGTATCAATGATTGTGGAGACCAAAGTGATGAACTGTGTTGTAAAGCATGCCAAGGCAAAGGCTTC

CATTGCAAATCGGGTGTTTGCATTCCAAGCCAGTATCAATGCAATGGTGAGGTGGACTGCATTACAGGGGAA

GATGAAGTTGGCTGTGCAGGCTTTGCATCTGTGGCTCAAGAAGAAACAGAAATTTTGACTGCTGACATGGAT

GCAGAAAGAAGACGGATAAAATCATTATTACCTAAACTATCTTGTGGAGTTAAAAACAGAATGCACATTCGA

AGGAAACGAATTGTGGGAGGAAAGCGAGCACAACTGGGAGACCTCCCATGGCAGGTGGCAATTAAGGATGCC

AGTGGAATCACCTGTGGGGGAATTTATATTGGTGGCTGTTGGATTCTGACTGCTGCACATTGTCTCAGAGCC

AGTAAAACTCATCGTTACCAAATATGGACAACAGTAGTAGACTGGATACACCCCGACCTTAAACGTATAGTA

ATTGAATACGTGGATAGAATTATTTTCCATGAAAACTACAATGCAGGCACTTACCAAAATGACATCGCTTTG

ATTGAAATGAAAAAAGACGGAAACAAAAAAGATTGTGAGCTGCCTCGTTCCATCCCTGCCTGTGTCCCCTGG

TCTCCTTACCTATTCCAACCTAATGATACATGCATCGTTTCTGGCTGGGGACGAGAAAAAGATAACGAAAGA

GTCTTTTCACTTCAGTGGGGTGAAGTTAAACTAATAAGCAACTGCTCTAAGTTTTACGGAAATCGTTTCTAT

GAAAAAGAAATGGAATGTGCAGGTACATATGATGGTTCCATCGATGCCTGTAAAGGGGACTCTGGAGGCCCC

TTAGTCTGTATGGATGCCAACAATGTGACTTATGTCTGGGGTGTTGTGAGTTGGGGGGAAAACTGTGGAAAA

CCAGAGTTCCCAGGTGTTTACACCAAAGTGGCCAATTATTTTGACTGGATTAGCTACCATGTAGGAAGGCCT

TTTATTTCTCAGTACAATGTATAA

RC001: FHL-1 wild type sequence:

(SEQ ID NO: 17)

ATGAGACTTCTAGCAAAGATTATTTGCCTTATGTTATGGGCTATTTGTGTAGCAGAAGATTGCAATGAACTT

CCTCCAAGAAGAAATACAGAAATTCTGACAGGTTCCTGGTCTGACCAAACATATCCAGAAGGCACCCAGGCT

ATCTATAAATGCCGCCCTGGATATAGATCTCTTGGAAATATAATAATGGTATGCAGGAAGGGAGAATGGGTT

GCTCTTAATCCATTAAGGAAATGTCAGAAAAGGCCCTGTGGACATCCTGGAGATACTCCTTTTGGTACTTTT

ACCCTTACAGGAGGAAATGTGTTTGAATATGGTGTAAAAGCTGTGTATACATGTAATGAGGGGTATCAATTG

CTAGGTGAGATTAATTACCGTGAATGTGACACAGATGGATGGACCAATGATATTCCTATATGTGAAGTTGTG

AAGTGTTTACCAGTGACAGCACCCGAGAATGGAAAAATTGTCAGTAGTGCAATGGAACCAGATCGGGAATAC

CATTTTGGACAAGCAGTACGGTTTGTATGTAACTCAGGCTACAAGATTGAAGGAGATGAAGAAATGCATTGT

TCAGACGATGGTTTTTGGAGTAAAGAGAAACCAAAGTGTGTGGAAATTTCATGCAAATCCCCAGATGTTATA

AATGGATCTCCTATATCTCAGAAGATTATTTATAAGGAGAATGAACGATTTCAATATAAATGTAACATGGGT

TATGAATACAGTGAAAGAGGAGATGCTGTATGCACTGAATCTGGATGGCGTCCGTTGCCTTCATGTGAAGAA

AAATCATGTGATAATCCTTATATTCCAAATGGTGACTACTCACCTTTAAGGATTAAACACAGAACTGGAGAT

GAAATCACGTACCAGTGTAGAAATGGTTTTTATCCTGCAACCCGGGGAAATACAGCaAAATGCACAAGTACT

GGCTGGATACCTGCTCCGAGATGTACCTTGAAACCTTGTGATTATCCAGACATTAAACATGGAGGTCTATAT

-continued

CATGAGAATATGCGTAGACCATACTTTCCAGTAGCTGTAGGAAAATATTACTCCTATTACTGTGATGAACAT

TTTGAGACTCCGTCAGGAAGTTACTGGGATCACATTCATTGCACACAAGATGGATGGTCGCCAGCAGTACCA

TGCCTCAGAAAATGTTATTTTCCTTATTTGGAAAATGGATATAATCAAAATTATGGAAGAAAGTTTGTACAG

GGTAAATCTATAGACGTTGCCTGCCATCCTGGCTACGCTCTTCCAAAAGCGCAGACCACAGTTACATGTATG

GAGAATGGCTGGTCTCCTACTCCCAGATGCATCCGTGTCAGCTTTACCCTCTGA

RC128: CFI GeneArt - Basic:

(SEQ ID NO: 18)

ATGAAGCTGCTGCATGTGTTTCTGCTGTTCCTCTGCTTCCACCTGAGGTTCTGCAAAGTGACCTACACCAGC

CAAGAGGACCTGGTGGAAAAGAAGTGCCTGGCCAAGAAGTACACCCACCTGAGCTGCGACAAGGTGTTCTGC

CAGCCTTGGCAGAGATGCATCGAGGGCACCTGTGTGTGCAAGCTGCCCTATCAGTGCCCCAAGAATGGCACA

GCCGTGTGCGCCACCAACAGAAGAAGCTTCCCTACCTACTGCCAGCAGAAAGCCTGGAATGTCTGCACCCC

GGCACCAAGTTTCTGAACAACGGCACCTGTACCGCCGAGGGCAAGTTTAGCGTGTCCCTGAAGCACGGCAAC

ACCGACTCTGAGGGCATCGTGGAAGTGAAGCTGGTGGACCAGGACAAGACCATGTTCATCTGCAAGAGCAGC

TGGTCCATGCGCGAGGCCAATGTGGCTTGTCTGGATCTGGGATTCCAGCAGGGCGCCGACACACAGAGAAGA

TTCAAGCTGAGCGACCTGAGCATCAACAGCACCGAGTGCCTGCATGTGCACTGTAGAGGCCTGGAAACAAGC

CTGGCCGAGTGCACCTTCACCAAGAGAAGGACCATGGGCTACCAGGACTTCGCCGACGTCGTGTGCTACACC

CAGAAAGCCGACTCTCCCATGGACGATTTCTTCCAGTGCGTGAACGGCAAGTACATCAGCCAGATGAAGGCC

TGCGACGGCATCAACGATTGCGGCGATCAGAGCGACGAGCTGTGCTGCAAAGCCTGTCAAGGCAAGGGCTTC

CACTGCAAGTCCGGCGTGTGTATCCCTAGCCAGTACCAGTGCAATGGCGAGGTGGACTGTATCACCGGCGAG

GATGAAGTGGGCTGTGCCGGATTTGCCAGCGTGGCCCAAGAGGAAACCGAGATCCTGACCGCCGATATGGAC

GCCGAGCGGCGGAGAATCAAAAGCCTGCTGCCTAAGCTGTCCTGCGGCGTGAAGAACCGGATGCACATCCGG

CGCAAGAGAATCGTCGGAGGCAAAAGAGCACAGCTGGGCGATCTGCCTTGGCAAGTGGCCATCAAGGATGCC

AGCGGCATCACATGTGGCGGCATCTACATCGGCGGCTGCTGGATTCTGACAGCCGCTCATTGTCTGCGGGCC

AGCAAGACCCACCGGTATCAGATCTGGACCACCGTGGTGGACTGGATTCACCCCGACCTGAAGCGGATCGTG

ATCGAGTACGTGGACCGGATCATCTTCCACGAGAACTACAACGCCGGCACCTACCAGAACGATATCGCCCTG

ATCGAGATGAAGAAGGACGGGAACAAGAAGGACTGCGAGCTGCCTAGATCTATCCCCGCCTGTGTTCCTTGG

AGCCCCTACCTGTTCCAGCCTAACGATACCTGCATCGTGTCCGGCTGGGGCAGAGAGAAGGATAACGAGAGG

GTGTTCAGCCTGCAGTGGGGCGAAGTGAAACTGATCAGCAACTGCAGCAAGTTCTACGGCAACCGGTTCTAC

GAGAAAGAAATGGAATGCGCCGGCACATACGACGGCTCCATCGATGCCTGTAAAGGCGATTCTGGCGGCCCT

CTCGTGTGCATGGATGCCAACAATGTGACCTACGTGTGGGGCGTCGTGTCCTGGGGAGAGAATTGTGGCAAG

CCTGAGTTCCCCGGCGTGTACACCAAGGTGGCCAACTACTTCGACTGGATCAGCTACCACGTGGGCAGACCC

TTTATCAGCCAGTACAACGTGTGA

RC129: CFI GeneArt - Manually optimised:

(SEQ ID NO: 19)

ATGAAGCTGCTCCATGTGTTTCTGCTCTTCCTCTGCTTCCACCTGAGGTTCTGCAAAGTGACCTACACCAGC

CAAGAGGACCTGGTGGAAAAGAAATGCCTGGCCAAGAAATACACCCACCTGAGCTGCGACAAGGTGTTCTGC

CAGCCTTGGCAGAGATGCATCGAGGGCACCTGTGTGTGCAAGCTGCCCTATCAGTGCCCCAAGAATGGCACA

GCCGTGTGCGCTACAAACAGAAGGAGCTTCCCTACCTACTGCCAGCAAAAAAGCCTGGAGTGCCTGCACCCC

GGCACCAAGTTTCTGAACAATGGCACCTGTACCGCCGAGGGCAAGTTTAGCGTGTCCCTGAAGCACGGCAAC

ACCGACTCTGAGGGCATCGTGGAAGTGAAGCTGGTGGACCAGGACAAGACCATGTTCATCTGCAAGAGCTCC

TGGTCCATGCGCGAGGCCAATGTGGCTTGTCTGGATCTGGGATTCCAGCAAGGCGCCGACACACAGAGAAGG

TTCAAGCTGAGCGACCTGAGCATCAACAGCACCGAGTGCCTGCATGTGCACTGTAGAGGCCTGGAAACAAGC

-continued

CTGGCCGAGTGCACCTTCACCAAGAGAAGGACCATGGGCTACCAGGACTTCGCCGACGTCGTGTGCTACACC

CAGAAAGCCGACTCTCCCATGGACGATTTCTTTCAGTGCGTGAACGGCAAGTACATCAGCCAGATGAAGGCC

TGCGACGGCATCAACGATTGCGGCGATCAGAGCGACGAGCTGTGCTGTAAAGCCTGTCAAGGCAAGGGCTTC

CACTGCAAGTCCGGCGTGTGTATCCCTAGCCAGTACCAGTGCAATGGCGAGGTGGACTGTATCACCGGCGAG

GATGAAGTGGGCTGTGCCGGATTTGCCAGCGTGGCCCAAGAGGAAACCGAGATCCTGACCGCCGATATGGAC

GCCGAGCGGAGGAGAATCAAAAGCCTGCTCCCTAAGCTGTCCTGCGCGTGAAGAACCGGATGCACATCCGG

CGCAAGAGAATCGTCGGAGGCAAAAGAGCACAGCTGGGCGATCTGCCTTGGCAAGTGGCCATCAAGGATGCC

AGCGGCATCACATGTGGCGGGATCTACATCGGCGGATGCTGGATTCTGACAGCCGCTCATTGTCTGCGGGCC

AGCAAGACCCACCGGTATCAGATCTGGACCACAGTGGTCGACTGGATTCACCCCGACCTGAAGCGGATCGTG

ATCGAGTACGTGGACCGGATCATTTTCCACGAGAACTACAACGCCGGCACCTACCAGAACGATATCGCCCTG

ATCGAGATGAAAAAGGACGGGAACAAGAAAGACTGCGAGCTGCCTAGATCTATCCCCGCCTGTGTTCCTTGG

AGCCCCTACCTGTTCCAGCCTAACGATACCTGCATCGTGTCCGGCTGGGGCAGAGAGAAGGATAACGAGAGG

GTGTTCAGCCTGCAGTGGGGCGAAGTGAAACTGATCAGCAACTGCAGCAAGTTCTACGGCAACCGGTTCTAC

GAGAAAGAAATGGAATGCGCCGGCACATACGACGGCTCCATCGATGCCTGTAAAGGCGATTCTGGCGGACCT

CTCGTGTGCATGGATGCCAACAATGTGACCTACGTGTGGGGCGTCGTGTCCTGGGGAGAGAATTGTGGCAAG

CCTGAGTTCCCCGGCGTGTACACCAAGGTGGCCAACTACTTCGACTGGATCAGCTACCACGTGGGCAGACCC

TTTATCAGCCAGTACAACGTGTGA

RC130: CFI Genscript - Basic:

(SEQ ID NO: 20)
ATGAAGCTGCTGCATGTCTTTCTGCTGTTTCTGTGCTTCCATCTGAGGTTCTGCAAGGTCACTTACACTAGC

CAGGAGGATCTGGTCGAGAAGAAGTGTCTGGCCAAGAAGTACACACACCTGAGCTGCGACAAGGTGTTCTGT

CAGCCTTGGCAGCGGTGCATCGAGGGCACCTGCGTGTGCAAGCTGCCTTACCAGTGCCCAAAGAACGGCACC

GCCGTGTGCGCCACAAATCGGAGATCTTTTCCAACATATTGCCAGCAGAAGAGCCTGGAGTGTCTGCACCCC

GGCACCAAGTTCCTGAACAATGGCACCTGCACAGCCGAGGGCAAGTTTTCTGTGAGCCTGAAGCACGGCAAC

ACAGATAGCGAGGGCATCGTGGAGGTGAAGCTGGTGGACCAGGATAAGACCATGTTCATCTGTAAGAGCAGC

TGGTCCATGAGGGAGGCAAACGTGGCATGCCTGGATCTGGGATTCCAGCAGGGAGCAGACACACAGAGGCGC

TTTAAGCTGTCCGACCTGTCTATCAATAGCACCGAGTGCCTGCACGTGCACTGTAGGGGCCTGGAGACATCC

CTGGCAGAGTGCACCTTCACAAAGCGGAGAACAATGGGCTACCAGGACTTTGCCGACGTGGTGTGCTATACC

CAGAAGGCCGATAGCCCTATGGACGATTTCTTTCAGTGCGTGAACGGCAAGTATATCTCCCAGATGAAGGCC

TGCGACGGCATCAATGACTGTGGCGATCAGTCTGACGAGCTGTGCTGTAAGGCCTGTCAGGGCAAGGGCTTC

CACTGCAAGAGCGGCGTGTGCATCCCTTCCCAGTACCAGTGCAACGGCGAGGTGGATTGTATCACAGGAGAG

GACGAAGTGGGATGCGCAGGATTTGCATCTGTGGCACAGGAGGAGACAGAGATCCTGACAGCCGACATGGAT

GCCGAGAGGCGCCGGATCAAGTCTCTGCTGCCTAAGCTGAGCTGTGGCGTGAAGAATCGGATGCACATCAGA

AGGAAGCGCATCGTGGGAGGCAAGCGGGCCCAGCTGGGCGATCTGCCCTGGCAGGTGGCCATCAAGGACGCC

TCTGGCATCACCTGCGGCGGCATCTACATCGGCGGCTGTTGGATTCTGACCGCAGCACACTGCCTGAGAGCA

AGCAAGACACACAGGTATCAGATCTGGACCACAGTGGTGGATTGGATTCACCCAGACCTGAAGAGAATCGTG

ATCGAGTACGTGGATAGGATCATCTTCCACGAGAACTACAATGCCGGCACATATCAGAACGACATCGCCCTG

ATCGAGATGAAGAAGGATGGCAATAAGAAGGACTGTGAGCTGCCCAGATCCATCCCTGCATGCGTGCCCTGG

AGCCCCTATCTGTTCCAGCCCAACGATACCTGCATCGTGTCCGGATGGGAAGGGAGAAGGACAATGAGCGG

GTGTTTTCTCTGCAGTGGGGCGAGGTGAAGCTGATCTCCAACTGTTCTAAGTTCTACGGCAATAGGTTTTAT

GAGAAGGAGATGGAGTGCGCCGGCACCTACGATGGCAGCATCGACGCCTGTAAGGGCGATTCCGGAGGACCA

CTGGTGTGCATGGACGCAAACAATGTGACATACGTGTGGGGAGTGGTGTCCTGGGGAGAGAACTGCGGCAAG

-continued

CCAGAGTTTCCCGGCGTGTATACCAAGGTGGCCAATTATTTTGATTGGATTTCATACCATGTCGGGAGACCA

TTCATTAGTCAGTACAACGTGTGA

RC131: CFI Genscript - Manually optimised:

(SEQ ID NO: 21)

ATGAAGCTGCTCCATGTCTTTCTGCTCTTTCTGTGCTTCCATCTGAGGTTCTGCAAGGTCACTTACACTAGC

CAGGAGGATCTGGTCGAGAAGAAATGTCTGGCCAAGAAATACACACACCTGAGCTGCGACAAGGTGTTCTGT

CAGCCTTGGCAGCGGTGCATCGAGGGCACCTGCGTGTGCAAGCTGCCTTACCAGTGCCCAAAGAACGGCACC

GCCGTGTGCGCCACAAATCGGAGATCTTTTCCAACATATTGCCAGCAAAAGAGCCTGGAGTGTCTGCACCCC

GGCACCAAGTTCCTGAACAATGGCACCTGCACAGCCGAGGGCAAGTTTTCTGTGAGCCTGAAGCACGGCAAC

ACAGATAGCGAGGGCATCGTGGAGGTGAAGCTGGTGGACCAGGATAAGACCATGTTCATCTGTAAGAGCTCC

TGGTCCATGAGGGAGGCAAACGTGGCATGCCTGGATCTGGGATTCCAGCAAGGAGCAGACACACAGAGGCGC

TTTAAGCTGTCCGATCTGAGTATCAATAGCACCGAGTGCCTGCACGTGCACTGTAGGGGCCTGGAGACATCC

CTGGCAGAGTGCACCTTCACAAAGCGGAGAACAATGGGCTACCAGGACTTTGCCGACGTGGTCTGCTATACC

CAGAAGGCCGATAGCCCTATGGACGATTTCTTTCAGTGCGTGAACGGCAAGTATATCTCCCAGATGAAGGCC

TGCGACGGCATCAATGACTGTGGCGATCAGTCTGACGAGCTGTGCTGTAAGGCCTGTCAGGGCAAGGGCTTC

CACTGCAAGAGCGGCGTGTGCATCCCTTCCCAGTACCAGTGCAACGGCGAGGTGGATTGTATCACAGGAGAG

GACGAAGTGGGATGCGCAGGATTTGCATCTGTGGCACAGGAGGAAACAGAGATCCTGACAGCCGACATGGAT

GCCGAGAGGCGCCGGATCAAGTCTCTGCTCCCTAAGCTGAGCTGTGGCGTGAAGAATCGGATGCACATCAGA

AGGAAGCGCATCGTGGGAGGCAAGCGGGCCCAGCTGGGCGATCTGCCCTGGCAGGTGGCCATCAAGGACGCC

TCTGGCATCACCTGCGGCGGGATCTACATCGGCGGATGTTGGATTCTGACCGCAGCCCACTGCCTGAGAGCA

AGCAAGACACACAGATATCAGATCTGGACCACAGTGGTCGATTGGATTCACCCAGACCTGAAGAGAATCGTG

ATCGAGTACGTGGATAGGATCATTTTCCACGAGAATTACAATGCTGGCACATATCAGAATGATATCGCTCTC

ATCGAGATGAAGAAAGATGGCAATAAGAAAGACTGTGAGCTGCCCAGATCCATCCCTGCATGCGTGCCCTGG

AGCCCCTATCTGTTCCAGCCCAACGATACCTGCATCGTGTCCGGATGGGGAAGGGAGAAGGACAATGAGCGG

GTGTTTTCTCTGCAGTGGGGCGAGGTGAAGCTGATCTCCAACTGTTCTAAGTTCTACGGCAATAGGTTTTAT

GAGAAGGAGATGGAGTGCGCCGGCACCTACGATGGCAGCATCGACGCCTGTAAGGGCGATTCCGGAGGCCCA

CTGGTGTGCATGGACGCAAACAATGTGACATACGTGTGGGGAGTGGTCTCCTGGGGAGAGAACTGCGGCAAG

CCAGAGTTTCCCGGCGTGTATACCAAGGTGGCCAATTATTTTGATTGGATTTCATACCATGTCGGGAGACCA

TTCATTAGTCAATACAACGTTTGA

RC132: CFI IDT - Basic:

(SEQ ID NO: 22)

ATGAAGCTCCTCCACGTCTTCTTGTTGTTTCTCTGTTTCCACCTGAGATTTTGCAAAGTAACTTACACCAGT

CAAGAAGACTTGGTCGAGAAGAAGTGTCTCGCCAAAAAGTATACTCACCTGAGCTGTGATAAAGTGTTCTGT

CAGCCGTGGCAGCGCTGCATTGAGGGTACATGTGTCTGTAAACTGCCTTATCAGTGTCCGAAGAACGGTACG

GCTGTCTGTGCTACTAACAGACGGTCTTTTCCTACTTATTGCCAGCAGAAGAGTTTGGAATGTCTCCACCCT

GGTACCAAGTTTCTCAACAATGGCACCTGTACTGCTGAAGGTAAATTCTCCGTCAGTCTCAAGCATGGTAAC

ACTGACAGTGAAGGGATAGTAGAGGTAAAGTTGGTTGACCAGGACAAGACGATGTTCATATGCAAGTCAAGC

TGGTCCATGCGCGAGGCGAATGTCGCTTGTCTTGATTTGGGCTTCCAGCAAGGGGCAGACACACAGAGAAGA

TTCAAATTGAGCGACCTGAGTATAAATTCAACCGAGTGCCTCCATGTACATTGCAGAGGGCTCGAGACTTCA

CTTGCCGAATGTACATTTACGAAGAGGCGGACTATGGGATATCAGGACTTTGCCGACGTAGTATGTTATACT

CAGAAAGCAGACAGTCCTATGGATGACTTTTTTCCAATGCGTCAACGGCAAATACATCAGTCAAATGAAAGCG

TGCGACGGTATCAACGATTGTGGTGACCAGTCTGATGAGCTTTGCTGTAAAGCATGTCAAGGAAAGGGGTTC

-continued

```
CATTGCAAGAGTGGTGTATGTATTCCCTCACAATATCAGTGCAATGGGGAAGTCGATTGCATAACAGGTGAG

GATGAGGTGGGCTGCGCGGGATTTGCTTCTGTGGCGCAAGAGGAGACTGAGATCCTTACAGCGGATATGGAC

GCCGAACGAAGACGCATCAAATCTCTCCTTCCCAAACTTTCATGCGGCGTCAAAAACCGAATGCATATACGC

AGGAAGAGAATTGTTGGGGGAAAGCGGGCACAGCTGGGCGACCTCCCCTGGCAAGTTGCAATAAAGGATGCA

AGTGGGATAACGTGCGGGGGCATCTACATCGGGGGGTGCTGGATCTTGACTGCCGCCCACTGTCTTAGAGCC

TCTAAGACCCATAGGTACCAAATCTGGACAACTGTAGTTGACTGGATACATCCGGACCTTAAACGCATAGTT

ATTGAATACGTTGACCGCATAATATTTCATGAGAATTATAACGCGGGTACCTATCAGAATGACATCGCCCTC

ATCGAGATGAAAAAAGACGGGAATAAAAAGGACTGCGAGCTGCCGCGCTCTATACCTGCGTGTGTCCCCTGG

AGTCCTTATCTTTTCCAACCTAACGATACGTGTATAGTGAGCGGCTGGGGCCGGGAGAAGGACAATGAACGA

GTTTTTTCCTTGCAATGGGGAGAAGTGAAGCTTATTTCCAATTGTTCAAAGTTTTATGGAAATAGATTTTAT

GAAAAAGAAATGGAGTGTGCGGGCACTTATGACGGGTCAATTGATGCTTGCAAAGGTGATAGCGGGGGCCCA

CTTGTCTGCATGGACGCTAACAACGTGACTTATGTGTGGGGTGTTGTGTCCTGGGGCGAAAACTGTGGCAAG

CCCGAGTTTCCCGGCGTATACACCAAAGTAGCTAATTATTTCGACTGGATTAGTTATCATGTTGGGCGGCCA

TTTATATCCCAGTATAATGTCTAA
```

RC133: CFI IDT - Manually optimised:

(SEQ ID NO: 23)

```
ATGAAGCTCCTGCACGTCTTCTTGCTGTTTCTCTGTTTCCACCTGAGATTTTGCAAAGTAACTTACACCAGT

CAAGAAGACTTGGTCGAGAAGAAATGTCTCGCCAAAAAGTATACTCACCTGAGCTGTGATAAAGTGTTCTGT

CAGCCGTGGCAGCGCTGCATTGAGGGTACATGTGTCTGTAAACTGCCTTATCAGTGTCCGAAGAACGGCACG

GCTGTCTGTGCTACTAACAGACGGTCTTTTCCTACTTATTGCCAGCAAAAGAGTTTGGAATGTCTCCACCCT

GGTACCAAGTTTCTCAACAATGGCACCTGTACTGCTGAAGGCAAATTCTCCGTCAGTCTCAAGCATGGTAAC

ACTGATTCTGAAGGGATAGTAGAAGTAAAGTTGGTTGACCAGGACAAGACGATGTTCATATGCAAGTCAAGC

TGGTCCATGCGCGAGGCGAATGTCGCTTGTCTTGATTTGGGCTTCCAGCAAGGGGCAGACACACAGAGAAGA

TTCAAATTGAGCGACCTGAGTATAAATTCAACCGAGTGCCTCCATGTACATTGCAGAGGGCTCGAGACTTCT

CTTGCTGAGTGTACATTTACGAAGAGGCGGACTATGGGATATCAGGACTTTGCTGACGTAGTGTGTTATACT

CAGAAAGCAGACAGTCCTATGGATGACTTTTTCCAATGCGTCAACGGCAAATACATCAGTCAAATGAAAGCG

TGCGACGGTATCAACGATTGTGGTGACCAGTCTGATGAGCTTTGCTGTAAAGCATGTCAAGGAAAGGGGTTC

CATTGCAAGAGTGGTGTATGTATTCCCTCACAATATCAGTGCAATGGGGAAGTCGATTGCATAACAGGCGAG

GATGAGGTGGGCTGCGCGGGATTTGCTTCTGTGGCGCAAGAGGAAACTGAGATCCTTACAGCGGATATGGAC

GCCGAACGAAGACGCATCAAATCTCTCCTTCCCAAACTTTCATGCGGCGTCAAAAACCGAATGCATATACGC

AGGAAGAGAATTGTTGGGGGAAAGCGGGCACAGCTGGGCGACCTCCCCTGGCAAGTTGCAATAAAGGATGCA

AGTGGGATAACGTGCGGGGGCATCTACATCGGGGGCTGCTGGATCTTGACTGCCGCTCACTGTCTTAGAGCC

TCTAAGACCCATAGATACCAAATCTGGACAACTGTAGTTGACTGGATACATCCGGACCTTAAACGCATAGTT

ATTGAATACGTTGACCGCATAATCTTTCATGAGAATTATAACGCGGGCACATACCAAAATGACATCGCCCTG

ATCGAGATGAAAAAGGACGGGAATAAAAAGGACTGCGAGCTGCCGCGCTCTATACCTGCGTGTGTCCCCTGG

AGTCCTTATCTTTTCCAACCTAACGATACGTGTATAGTGAGCGGCTGGGGCCGGGAGAAGGACAATGAACGA

GTTTTTTCCTTGCAATGGGGAGAAGTGAAGCTTATTTCCAATTGTTCAAAGTTTTATGGAAATAGATTTTAT

GAAAAAGAAATGGAGTGTGCGGGCACTTATGACGGGTCAATTGATGCTTGCAAAGGTGATAGCGGGGGCCCA

CTTGTCTGCATGGACGCTAACAATGTGACTTATGTGTGGGGTGTTGTGTCCTGGGGCGAAAACTGTGGCAAG
```

-continued

CCCGAGTTTCCCGGCGTATACACCAAAGTAGCTAATTATTTCGACTGGATTAGTTATCATGTTGGGCGGCCA

TTTATATCCCAGTATAATGTCTAA

RC134: CFI JCat - Basic:

(SEQ ID NO: 24)

ATGAAGCTGCTGCACGTGTTCCTGCTGTTCCTGTGCTTCCACCTGCGCTTCTGCAAGGTGACCTACACCAGC

CAGGAGGACCTGGTGGAGAAGAAGTGCCTGGCCAAGAAGTACACCCACCTGAGCTGCGACAAGGTGTTCTGC

CAGCCCTGGCAGCGCTGCATCGAGGGCACCTGCGTGTGCAAGCTGCCCTACCAGTGCCCCAAGAACGGCACC

GCCGTGTGCGCCACCAACCGCCGCAGCTTCCCCACCTACTGCCAGCAGAAGAGCCTGGAGTGCCTGCACCCC

GGCACCAAGTTCCTGAACAACGGCACCTGCACCGCCGAGGGCAAGTTCAGCGTGAGCCTGAAGCACGGCAAC

ACCGACAGCGAGGGCATCGTGGAGGTGAAGCTGGTGGACCAGGACAAGACCATGTTCATCTGCAAGAGCAGC

TGGAGCATGCGCGAGGCCAACGTGGCCTGCCTGGACCTGGGCTTCCAGCAGGGCGCCGACACCCAGCGCCGC

TTCAAGCTGAGCGACCTGAGCATCAACAGCACCGAGTGCCTGCACGTGCACTGCCGCGGCCTGGAGACCAGC

CTGGCCGAGTGCACCTTCACCAAGCGCCGCACCATGGGCTACCAGGACTTCGCCGACGTGGTGTGCTACACC

CAGAAGGCCGACAGCCCCATGGACGACTTCTTCCAGTGCGTGAACGGCAAGTACATCAGCCAGATGAAGGCC

TGCGACGGCATCAACGACTGCGGCGACCAGAGCGACGAGCTGTGCTGCAAGGCCTGCCAGGGCAAGGGCTTC

CACTGCAAGAGCGGCGTGTGCATCCCCAGCCAGTACCAGTGCAACGGCGAGGTGGACTGCATCACCGGCGAG

GACGAGGTGGGCTGCGCCGGCTTCGCCAGCGTGGCCCAGGAGGAGACCGAGATCCTGACCGCCGACATGGAC

GCCGAGCGCCGCCGCATCAAGAGCCTGCTGCCCAAGCTGAGCTGCGGCGTGAAGAACCGCATGCACATCCGC

CGCAAGCGCATCGTGGGCGGCAAGCGCGCCCAGCTGGGCGACCTGCCCTGGCAGGTGGCCATCAAGGACGCC

AGCGGCATCACCTGCGGCGGCATCTACATCGGCGGCTGCTGGATCCTGACCGCCGCCCACTGCCTGCGCGCC

AGCAAGACCCACCGCTACCAGATCTGGACCACCGTGGTGGACTGGATCCACCCCGACCTGAAGCGCATCGTG

ATCGAGTACGTGGACCGCATCATCTTCCACGAGAACTACAACGCCGGCACCTACCAGAACGACATCGCCCTG

ATCGAGATGAAGAAGGACGGCAACAAGAAGGACTGCGAGCTGCCCCGCAGCATCCCCGCCTGCGTGCCCTGG

AGCCCCTACCTGTTCCAGCCCAACGACACCTGCATCGTGAGCGGCTGGGGCCGCGAGAAGGACAACGAGCGC

GTGTTCAGCCTGCAGTGGGGCGAGGTGAAGCTGATCAGCAACTGCAGCAAGTTCTACGGCAACCGCTTCTAC

GAGAAGGAGATGGAGTGCGCCGGCACCTACGACGGCAGCATCGACGCCTGCAAGGGCGACAGCGGCGGCCCC

CTGGTGTGCATGGACGCCAACAACGTGACCTACGTGTGGGGCGTGGTGAGCTGGGGCGAGAACTGCGGCAAG

CCCGAGTTCCCCGGCGTGTACACCAAGGTGGCCAACTACTTCGACTGGATCAGCTACCACGTGGGCCGCCCC

TTCATCAGCCAGTACAACGTGTAA

RC135: CFI JCat - Manually optimised:

(SEQ ID NO: 25)

ATGAAGCTGCTCCACGTGTTCCTGCTCTTCCTGTGCTTCCACCTGCGCTTCTGCAAGGTGACCTACACCAGC

CAGGAGGACCTGGTGGAGAAGAAATGCCTGGCCAAGAAATACACCCACCTGAGCTGCGACAAGGTGTTCTGC

CAGCCCTGGCAGCGCTGCATCGAGGGCACCTGCGTGTGCAAGCTGCCCTACCAGTGCCCCAAGAACGGCACC

GCCGTGTGCGCCACCAACCGCCGGAGCTTCCCCACCTACTGCCAGCAAAAGAGCCTGGAGTGCCTGCACCCC

GGCACCAAGTTCCTGAACAATGGCACCTGCACCGCCGAGGGCAAGTTCAGCGTGAGCCTGAAGCACGGCAAC

ACCGACAGCGAGGGCATCGTGGAGGTGAAGCTGGTGGACCAGGACAAGACCATGTTCATCTGCAAGAGCTCC

TGGAGCATGCGCGAGGCCAACGTGGCCTGCCTGGACCTGGGCTTCCAGCAAGGCGCCGACACCCAGCGCCGG

TTCAAGCTGAGCGACCTGAGCATCAACAGCACCGAGTGCCTGCACGTGCACTGCCGCGGCCTGGAGACCAGC

CTGGCCGAGTGCACCTTCACCAAGCGCCGGACCATGGGCTACCAGGACTTCGCCGACGTGGTCTGCTACACC

CAGAAGGCTGACTCTCCCATGGACGATTTCTTTCAGTGCGTGAACGGCAAGTACATCAGCCAGATGAAGGCC

TGCGACGGCATCAACGACTGCGGCGACCAGAGCGACGAGCTGTGCTGTAAGGCCTGCCAGGGCAAGGGCTTC

CACTGCAAGAGCGGCGTGTGCATCCCCAGCCAGTACCAGTGCAACGGCGAGGTGGACTGCATCACCGGCGAG

-continued

GACGAGGTGGGCTGCGCCGGCTTCGCCAGCGTGGCCCAGGAGGAAACCGAGATCCTGACCGCCGACATGGAC

GCCGAGCGCAGAAGGATCAAGAGCCTGCTCCCCAAGCTGAGCTGCGGCGTGAAGAACCGCATGCACATCCGC

AGAAAGCGCATCGTGGGCGGGAAGCGCGCCCAGCTGGGCGACCTGCCCTGGCAGGTGGCCATCAAGGACGCC

AGCGGCATCACCTGCGGCGGAATCTACATCGGCGGGTGCTGGATCCTGACCGCCGCTCACTGCCTGCGCGCC

AGCAAGACCCACCGCTACCAGATCTGGACCACAGTGGTCGACTGGATCCACCCCGACCTGAAGCGCATCGTG

ATCGAGTACGTGGACCGCATCATTTTCCACGAGAACTACAACGCCGGCACCTACCAGAACGACATCGCCCTG

ATCGAGATGAAGAAAGATGGAAACAAGAAAGACTGCGAGCTGCCCCGCAGCATCCCCGCCTGCGTGCCCTGG

AGCCCCTACCTGTTCCAGCCCAACGACACCTGCATCGTGAGCGGCTGGGGCCGCGAGAAGGACAACGAGCGC

GTGTTCAGCCTGCAGTGGGGCGAGGTGAAGCTGATCAGCAACTGCAGCAAGTTCTACGGCAACCGCTTCTAC

GAGAAGGAGATGGAGTGCGCCGGCACCTACGACGGCAGCATCGACGCCTGCAAGGGCGACAGCGGCGGGCCC

CTGGTGTGCATGGACGCCAACAATGTGACCTACGTGTGGGGCGTGGTCAGCTGGGGCGAGAACTGCGGCAAG

CCCGAGTTCCCCGGCGTGTACACCAAGGTGGCCAACTACTTCGACTGGATCAGCTACCACGTGGGCCGCCCC

TTTATCTCTCAATACAACGTCTAA

RC136: CFI COOL - Basic: see SEQ ID NO: 10, above.
RC137: CFI COOL - Manually optimised:

(SEQ ID NO: 26)

ATGAAACTGCTCCATGTCTTCCTCCTGTTCCTGTGCTTCCACCTCCGTTTCTGTAAAGTCACCTACACTAGC

CAGGAGGATCTGGTGGAGAAGAAATGCCTGGCCAAGAAATATACCCACCTGAGCTGCGACAAAGTGTTCTGC

CAGCCCTGGCAACGCTGCATTGAAGGCACTTGTGTGTGCAAGCTGCCCTACCAGTGCCCCAAGAACGGCACG

GCCGTGTGTGCCACCAACAGGAGAAGCTTCCCCACCTACTGCCAGCAAAAGAGCCTGGAATGCCTCCACCCT

GGCACCAAGTTTCTGAACAATGGGACCTGCACAGCCGAGGGGAAATTCAGCGTCTCCCTCAAGCACGGCAAT

ACAGACTCCGAGGGCATTGTGGAAGTGAAGCTGGTGGACCAGGACAAGACCATGTTCATCTGCAAAAGCTCC

TGGTCCATGCGGGAGGCCAATGTCGCCTGCCTGGACCTGGGCTTCCAGCAAGGCGCTGATACACAGCGCAGA

TTTAAACTCAGTGACCTCAGCATCAACAGCACTGAGTGTCTGCACGTGCACTGCCGGGGCCTGGAGACCAGC

CTGGCTGAGTGCACCTTCACCAAGCGCAGGACCATGGGCTACCAGGATTTTGCAGATGTGGTCTGCTACACC

CAGAAGGCAGACAGCCCCATGGATGACTTCTTTCAGTGTGTCAATGGCAAGTACATTTCCCAGATGAAGGCT

TGTGACGGGATCAATGATTGCGGGGATCAGAGCGATGAGCTCTGCTGTAAGGCCTGCCAAGGGAAGGGCTTT

CACTGCAAGTCTGGGGTGTGCATCCCTTCTCAGTATCAGTGCAACGGAGAGGTGGACTGCATCACTGGGGAG

GACGAGGTGGGCTGTGCTGGCTTCGCCTCTGTGGCCCAGGAGGAAACAGAGATCCTCACAGCTGACATGGAT

GCAGAGCGGAGGCGCATCAAGAGTCTGCTCCCAAAGCTCTCCTGCGGCGTTAAGAATCGCATGCACATCCGG

AGGAAGCGGATCGTTGGAGGCAAACGGGCTCAGCTGGGGGACTTGCCGTGGCAGGTGGCCATCAAAGATGCC

TCCGGAATCACCTGTGGTGGCATCTACATCGGCGGGTGCTGGATCCTGACCGCCGCTCACTGCCTTCGGGCC

AGCAAGACCCATCGCTACCAGATCTGGACCACAGTGGTCGATTGGATTCACCCCGACCTGAAGAGGATTGTC

ATTGAGTATGTCGACCGCATCATTTTCCATGAAAACTACAATGCCGGGACGTATCAGAACGACATCGCCCTC

ATCGAGATGAAGAAAGATGGGAACAAGAAAGACTGTGAGCTGCCCTCGCTCCATCCCCGCCTGTGTACCATGG

TCTCCGTACCTGTTCCAGCCAAATGACACATGCATCGTGAGCGGCTGGGGCCGCGAGAAAGACAACGAGAGG

GTCTTCTCCCTGCAGTGGGGTGAAGTCAAGCTGATCAGCAACTGCTCCAAGTTCTACGGCAACCGCTTCTAT

GAGAAGGAGATGGAGTGCGCCGGCACCTATGACGGCAGCATTGACGCGTGCAAGGGAGACAGTGGGGGCCCC

CTGGTCTGCATGGACGCCAACAATGTGACCTACGTGTGGGGAGTTGTGTCCTGGGGCGAGAACTGTGGCAAG

CCTGAGTTCCCGGGCGTGTACACAAAGGTGGCAAACTATTTTGACTGGATCTCCTATCACGTTGGCAGGCCC

TTCATTAGCCAGTATAATGTATAA

RC138: FHL-1 GeneArt - Basic:

(SEQ ID NO: 27)

ATGAGACTGCTGGCCAAGATCATCTGCCTGATGCTGTGGGCCATCTGCGTGGCCGAGGATTGCAATGAGCTG

CCTCCTCGGAGAAACACCGAGATCCTGACAGGCTCTTGGAGCGACCAGACATACCCTGAGGGAACCCAGGCC

ATCTACAAGTGCAGACCCGGCTACAGAAGCCTGGGCAACATCATCATGGTCTGCCGGAAAGGCGAGTGGGTC

GCCCTGAATCCTCTGCGGAAGTGCCAGAAAAGACCCTGCGGACACCCTGGCGATACCCCTTTCGGAACCTTT

ACACTGACCGGCGGCAACGTGTTCGAGTACGGCGTGAAAGCCGTGTACACCTGTAACGAGGGCTACCAGCTG

CTGGGCGAGATCAACTACAGAGAGTGCGATACCGACGGCTGGACCAACGACATCCCTATCTGCGAGGTGGTC

AAGTGCCTGCCTGTGACAGCCCCTGAGAACGGCAAGATTGTGTCCAGCGCCATGGAACCCGACAGAGAGTAC

CACTTTGGCCAGGCCGTCAGATTCGTGTGCAACAGCGGCTACAAGATCGAGGGCGACGAGGAAATGCACTGC

AGCGACGATGGCTTCTGGTCCAAAGAAAAGCCTAAGTGCGTGGAAATCAGCTGCAAGAGCCCCGACGTGATC

AACGGCAGCCCTATCAGCCAGAAGATTATCTACAAAGAGAACGAGCGGTTCCAGTACAAGTGTAACATGGGC

TACGAGTACAGCGAGAGGGGCGACGCCGTGTGTACAGAATCTGGATGGCGACCTCTGCCTAGCTGCGAGGAA

AAGAGCTGCGACAACCCTTACATCCCCAACGGCGACTACAGCCCACTGCGGATCAAACACAGAACCGGCGAC

GAGATCACCTACCAGTGCCGGAATGGCTTCTACCCTGCCACCAGAGGCAATACCGCCAAGTGTACAAGCACC

GGCTGGATCCCTGCTCCTCGGTGTACACTGAAGCCCTGCGACTACCCCGATATCAAGCACGGCGGACTGTAC

CACGAGAACATGCGGAGGCCTTACTTCCCTGTGGCCGTGGGCAAGTACTACAGCTACTACTGCGACGAGCAC

TTCGAGACACCCAGCGGCAGCTACTGGGATCACATCCACTGTACCCAGGACGGCTGGTCACCAGCTGTGCCT

TGCCTGAGAAAGTGCTACTTCCCCTACCTGGAAAACGGCTACAACCAGAACTACGGCCGGAAGTTCGTGCAG

GGCAAGAGCATCGATGTGGCCTGCCATCCTGGATACGCCCTGCCTAAGGCTCAGACCACCGTGACCTGCATG

GAAAATGGCTGGTCCCCAACACCTCGGTGCATCCGGGTGTCCTTCACACTGTAA

RC139: FHL-1 GeneArt - Manually optimised:

(SEQ ID NO: 28)

ATGAGACTGCTCGCCAAGATCATTTGCCTGATGCTGTGGGCCATCTGCGTGGCCGAGGATTGCAATGAGCTG

CCTCCCCGGAGAAACACCGAGATCCTGACAGGCTCTTGGAGCGACCAGACATACCCTGAGGGAACCCAGGCC

ATCTACAAGTGCAGACCCGGCTACAGAAGCCTGGGCAACATCATTATGGTCTGCCGGAAAGGCGAGTGGGTC

GCCCTGAATCCTCTGCGGAAGTGCCAGAAAAGACCCTGCGGACACCCTGGCGATACCCCTTTCGGAACCTTT

ACACTGACCGGCGGGAACGTGTTCGAGTACGGCGTGAAAGCCGTGTACACCTGTAACGAGGGCTACCAGCTG

CTCGGCGAGATCAACTACAGAGAGTGCGATACCGACGGCTGGACCAACGACATCCCTATCTGCGAGGTGGTC

AAGTGCCTGCCTGTGACAGCCCCTGAGAACGGCAAGATTGTGTCCAGCGCCATGGAACCCGACAGAGAGTAC

CACTTTGGCCAGGCCGTCAGATTCGTGTGCAACAGCGGCTACAAGATCGAGGGCGACGAGGAAATGCACTGC

AGCGACGATGGCTTCTGGTCCAAAGAAAAGCCTAAGTGCGTGGAAATCAGCTGCAAGAGCCCCGACGTGATC

AACGGCAGCCCTATCAGCCAGAAGATTATCTACAAAGAGAACGAGCGGTTCCAGTACAAGTGTAACATGGGC

TACGAGTACAGCGAGAGGGGCGACGCCGTGTGTACAGAATCTGGATGGCGACCTCTGCCTAGCTGCGAGGAA

AAGAGCTGCGACAACCCTTACATCCCCAACGGCGACTACAGCCCACTGCGGATCAAACACAGAACCGGCGAC

GAGATCACCTACCAGTGCCGGAATGGCTTCTACCCTGCCACCAGAGGCAATACCGCCAAGTGTACAAGCACC

GGCTGGATCCCTGCTCCTCGGTGTACACTGAAGCCCTGCGACTACCCCGATATCAAGCACGGCGGACTGTAC

CACGAGAACATGCGGAGGCCTTACTTCCCTGTGGCCGTGGGCAAGTACTATAGCTACTATTGCGACGAGCAC

TTCGAGACACCCAGCGGCAGCTACTGGGATCACATCCACTGTACCCAGGACGGCTGGTCACCAGCTGTGCCT

-continued

TGCCTGAGAAAGTGCTACTTCCCCTACCTGGAAAACGGCTACAACCAGAACTACGGCCGGAAGTTCGTGCAG

GGCAAGAGCATCGATGTGGCCTGCCATCCTGGATACGCCCTGCCTAAGGCTCAGACCACAGTGACCTGCATG

GAAAATGGCTGGTCCCCAACACCTCGGTGCATCCGGGTGTCCTTCACACTGTAA

RC140: FHL-1 Genscript - Basic:

(SEQ ID NO: 29)

ATGCGGCTGCTGGCCAAGATCATCTGCCTGATGCTGTGGGCCATCTGCGTGGCCGAGGACTGTAACGAGCTG

CCCCCTCGGAGAAATACAGAGATCCTGACCGGCTCTTGGAGCGATCAGACATATCCTGAGGGCACCCAGGCC

ATCTACAAGTGCAGGCCAGGCTATCGCTCCCTGGGCAACATCATCATGGTGTGCAGGAAGGGAGAGTGGGTG

GCCCTGAATCCTCTGAGGAAGTGCCAGAAGAGGCCATGTGGACACCCAGGCGACACCCCTTTCGGCACCTTT

ACACTGACCGGCGGCAACGTGTTCGAGTACGGCGTGAAGGCCGTGTATACATGCAACGAGGGCTACCAGCTG

CTGGGCGAGATCAATTACAGAGAGTGTGACACAGATGGCTGGACCAACGATATCCCAATCTGCGAGGTGGTG

AAGTGTCTGCCAGTGACCGCCCCCGAGAATGGCAAGATCGTGAGCTCCGCCATGGAGCCCGACAGGGAGTAT

CACTTCGGCCAGGCCGTGCGCTTCGTGTGCAACTCTGGCTACAAGATCGAGGGCGATGAGGAGATGCACTGT

AGCGACGATGGCTTCTGGTCCAAGGAGAAGCCCAAGTGCGTGGAGATCAGCTGTAAGTCCCCAGACGTGATC

AATGGCTCTCCCATCAGCCAGAAGATCATCTATAAGGAGAACGAGAGGTTTCAGTACAAGTGCAATATGGGC

TACGAGTATTCCGAGAGGGGCGATGCCGTGTGCACCGAGTCTGGCTGGAGACCACTGCCCTCCTGCGAGGAG

AAGTCTTGTGACAACCCATATATCCCCAATGGCGATTACTCTCCCCTGCGGATCAAGCACAGAACAGGCGAC

GAGATCACCTATCAGTGCCGGAACGGCTTCTACCCTGCCACAAGAGGCAATACCGCCAAGTGTACAAGCACC

GGATGGATCCCTGCACCAAGGTGCACCCTGAAGCCTTGTGACTATCCAGATATCAAGCACGGCGGCCTGTAT

CACGAGAATATGAGGCGCCCTTACTTCCCAGTGGCCGTGGGCAAGTACTATAGCTACTATTGCGACGAGCAC

TTTGAGACCCCTTCCGGCTCTTACTGGGACCACATCCACTGTACACAGGATGGATGGTCCCCAGCAGTGCCT

TGCCTGAGGAAGTGTTACTTCCCATATCTGGAGAACGGCTACAACCAGAATTATGGCCGCAAGTTTGTGCAG

GGCAAGAGCATCGATGTGGCATGCCACCCAGGATACGCACTGCCTAAGGCACAGACCACAGTGACATGCATG

GAGAATGGCTGGTCTCCCACCCCTCGGTGTATCAGAGTGAGCTTTACACTGTGA

RC141: FHL-1 Genscript - Manually optimised:

(SEQ ID NO: 30)

ATGCGGCTGCTCGCCAAGATCATTTGCCTGATGCTGTGGGCCATCTGCGTGGCCGAGGACTGTAACGAGCTG

CCCCCTCGGAGAAATACAGAGATCCTGACCGGCTCTTGGAGCGATCAGACATATCCTGAGGGCACCCAGGCC

ATCTACAAGTGCAGGCCAGGCTATCGCTCCCTGGGCAACATCATTATGGTGTGCAGGAAGGGAGAGTGGGTG

GCCCTGAATCCTCTGAGGAAGTGCCAGAAGAGGCCATGTGGACACCCAGGCGACACCCCTTTCGGCACCTTT

ACACTGACCGGCGGGAACGTGTTCGAGTACGGCGTGAAGGCCGTGTATACATGCAACGAGGGCTACCAGCTG

CTCGGCGAGATCAATTACAGAGAGTGTGACACAGATGGCTGGACCAACGATATCCCAATCTGCGAGGTGGTC

AAGTGTCTGCCAGTGACCGCCCCCGAGAATGGCAAGATCGTGAGCTCCGCCATGGAGCCCGACAGGGAGTAT

CACTTCGGCCAGGCCGTGCGCTTCGTGTGCAACTCTGGCTACAAGATCGAGGGCGATGAGGAAATGCACTGT

AGCGACGATGGCTTCTGGTCCAAGGAGAAGCCCAAGTGCGTGGAGATCAGCTGCAAGTCCCCAGACGTGATC

AATGGCTCTCCCATCAGCCAGAAGATCATTTATAAGGAGAACGAGAGGTTTCAGTACAAGTGCAATATGGGC

TACGAGTATTCCGAGAGGGGCGATGCCGTGTGCACCGAGTCTGGCTGGAGACCACTGCCCTCCTGCGAGGAA

AAGTCTTGTGACAACCCATATATCCCCAATGGCGATTACTCTCCCCTGCGGATCAAGCACAGAACAGGCGAC

GAGATCACCTATCAGTGCCGGAACGGCTTCTACCCTGCCACAAGAGGCAATACCGCCAAGTGTACAAGCACC

GGATGGATCCCTGCACCAAGGTGCACCCTGAAGCCTTGTGACTATCCAGATATCAAGCACGGCGGGCTGTAT

CACGAGAATATGAGGCGCCCTTACTTCCCAGTGGCCGTGGGCAAGTACTATAGCTACTATTGCGACGAGCAC

TTTGAGACCCCTTCCGGCTCTTACTGGGACCACATCCACTGTACACAGGATGGATGGTCCCCAGCAGTGCCT

-continued

TGCCTGAGGAAGTGTTACTTCCCATATCTGGAGAACGGCTACAACCAGAATTATGGCCGCAAGTTTGTGCAG

GGCAAGAGCATCGATGTGGCATGCCACCCAGGATACGCACTGCCTAAGGCACAGACCACAGTGACATGCATG

GAGAATGGCTGGTCTCCCACCCCTCGGTGTATCAGAGTGAGCTTTACACTGTGA

RC142: FHL-1 IDT - Basic:

(SEQ ID NO: 31)

ATGAGACTGCTTGCGAAAATTATATGCCTGATGCTTTGGGCTATTTGCGTTGCGGAAGACTGTAACGAACTC

CCGCCCCGCCGAAATACAGAGATCCTCACAGGCAGTTGGAGCGACCAAACGTACCCTGAAGGTACGCAGGCC

ATATATAAGTGTAGGCCAGGCTACAGATCACTTGGTAACATAATAATGGTATGTCGGAAAGGAGAGTGGGTC

GCTCTCAACCCTCTTAGGAAATGTCAAAAAAGACCCTGTGGGCATCCGGGAGATACGCCTTTCGGGACATTC

ACTCTCACGGGCGGAAACGTATTCGAATATGGCGTGAAGGCAGTGTATACCTGCAATGAAGGGTATCAGCTG

CTTGGGGAAATTAATTATAGGGAATGTGACACGGATGGGTGGACAAACGATATTCCAATATGCGAAGTAGTT

AAATGCCTGCCCGTTACTGCACCGGAGAATGGCAAAATAGTCAGTAGTGCAATGGAGCCGGATCGCGAGTAT

CATTTTGGTCAGGCCGTGCGGTTCGTATGTAATTCTGGGTACAAGATCGAAGGTGACGAAGAGATGCATTGC

TCAGATGACGGCTTTTGGAGTAAAGAAAAGCCTAAGTGTGTTGAAATCAGCTGTAAGAGTCCAGACGTGATT

AACGGTTCCCCGATCTCTCAGAAGATAATTTACAAGGAAAACGAACGATTCCAATATAAGTGTAACATGGGC

TACGAGTATTCCGAGCGAGGTGACGCAGTATGTACGGAAAGCGGGTGGCGACCTCTGCCCTCCTGCGAGGAA

AAGAGCTGTGATAATCCGTATATCCCCAACGGTGACTATAGCCCACTGCGCATAAAACATCGGACGGGAGAT

GAGATTACATACCAATGCCGCAATGGTTTTTACCCCGCCACCCGAGGGAACACGGCAAAGTGCACTTCTACG

GGGTGGATTCCAGCTCCTAGGTGCACTCTTAAACCCTGCGACTACCCAGATATCAAGCATGGTGGACTGTAT

CATGAGAATATGAGGAGACCATACTTTCCAGTTGCAGTGGGCAAGTACTATAGCTATTACTGTGATGAGCAC

TTTGAAACTCCGTCTGGGAGCTACTGGGATCATATCCATTGTACGCAAGACGGCTGGAGTCCAGCAGTTCCA

TGCTTGCGGAAATGTTATTTTCCCTACCTCGAAAACGGATATAATCAGAACTATGGGAGGAAGTTTGTTCAA

GGCAAAAGCATTGATGTGGCATGTCACCCCGGTTATGCCCTGCCCAAGGCGCAAACCACAGTAACTTGCATG

GAGAATGGATGGAGCCCCACACCCAGATGTATACGAGTATCCTTCACGCTTTGA

RC143: FHL-1 IDT - Manually optimised:

(SEQ ID NO: 32)

ATGAGACTGCTTGCGAAAATTATATGCCTGATGCTTTGGGCTATTTGCGTTGCGGAAGACTGTAACGAACTC

CCGCCCCGCCGAAATACAGAGATCCTCACAGGCAGTTGGAGCGACCAAACGTACCCTGAAGGCACGCAGGCC

ATATATAAGTGTAGGCCAGGCTACAGATCACTTGGTAACATAATCATGGTGTGTCGGAAAGGAGAGTGGGTC

GCTCTCAACCCTCTTCGCAAATGTCAAAAAAGACCCTGTGGGCATCCGGGAGATACGCCTTTCGGGACATTC

ACTCTCACGGGCGGAAACGTATTCGAATATGGCGTGAAGGCAGTGTATACCTGCAATGAAGGGTATCAGCTG

CTTGGGGAAATTAATTATAGGGAATGTGACACGGATGGGTGGACAAACGATATTCCAATATGCGAAGTAGTT

AAATGCCTGCCCGTTACTGCACCGGAGAATGGCAAAATAGTCAGTAGCGCAATGGAGCCGGATCGCGAGTAT

CATTTTGGTCAGGCCGTGCGGTTCGTATGTAATTCTGGGTACAAGATCGAAGGTGACGAAGAGATGCATTGC

TCAGATGACGGCTTTTGGAGCAAGGAAAAGCCTAAGTGTGTTGAAATCAGCTGTAAGAGTCCAGACGTGATT

AACGGTTCCCCGATCTCTCAGAAGATAATTTACAAGGAAAACGAACGATTCCAATATAAGTGTAACATGGGC

TACGAGTATTCCGAGCGAGGTGACGCAGTATGTACGGAAAGCGGGTGGCGACCTCTGCCCTCCTGCGAGGAA

AAGAGCTGTGATAATCCGTATATCCCCAACGGCGACTATAGCCCACTGCGCATAAAACATCGGACGGGAGAT

GAGATTACATACCAATGCCGCAATGGTTTTTACCCCGCCACCCGAGGGAACACGGCAAAGTGCACTTCTACG

GGGTGGATTCCAGCTCCTAGGTGCACTCTTAAACCCTGCGACTACCCAGATATCAAGCATGGTGGACTGTAT

CATGAGAATATGAGGAGACCATACTTTCCAGTTGCAGTGGGCAAGTACTATAGCTATTACTGTGATGAGCAC

TTTGAAACTCCGTCTGGGAGCTACTGGGATCATATCCATTGTACGCAAGACGGCTGGAGTCCAGCAGTTCCA

TGCTTGCGGAAATGTTATTTTCCCTACCTCGAAAACGGATATAATCAGAATTACGGCAGGAAATTTGTGCAA

-continued

GGCAAAAGCATTGATGTGGCATGTCACCCCGGTTATGCCCTGCCCAAGGCGCAAACCACAGTAACTTGCATG

GAGAATGGATGGAGCCCCACACCCAGATGTATACGAGTATCCTTCACGCTTTGA

RC144: FHL-1 JCat - Basic (SEQ ID NO: 33)
ATGCGCCTGCTGGCCAAGATCATCTGCCTGATGCTGTGGGCCATCTGCGTGGCCGAGGACTGCAACGAGCTG

CCCCCCCGCCGCAACACCGAGATCCTGACCGGCAGCTGGAGCGACCAGACCTACCCCGAGGGCACCCAGGCC

ATCTACAAGTGCCGCCCCGGCTACCGCAGCCTGGGCAACATCATCATGGTGTGCCGCAAGGGCGAGTGGGTG

GCCCTGAACCCCCTGCGCAAGTGCCAGAAGCGCCCCTGCGGCCACCCCGGCGACACCCCCTTCGGCACCTTC

ACCCTGACCGGCGGCAACGTGTTCGAGTACGGCGTGAAGGCCGTGTACACCTGCAACGAGGGCTACCAGCTG

CTGGGCGAGATCAACTACCGCGAGTGCGACACCGACGGCTGGACCAACGACATCCCCATCTGCGAGGTGGTG

AAGTGCCTGCCCGTGACCGCCCCCGAGAACGGCAAGATCGTGAGCAGCGCCATGGAGCCCGACCGCGAGTAC

CACTTCGGCCAGGCCGTGCGCTTCGTGTGCAACAGCGGCTACAAGATCGAGGGCGACGAGGAGATGCACTGC

AGCGACGACGGCTTCTGGAGCAAGGAGAAGCCCAAGTGCGTGGAGATCAGCTGCAAGAGCCCCGACGTGATC

AACGGCAGCCCCATCAGCCAGAAGATCATCTACAAGGAGAACGAGCGCTTCCAGTACAAGTGCAACATGGGC

TACGAGTACAGCGAGCGCGGCGACGCCGTGTGCACCGAGAGCGGCTGGCGCCCCCTGCCCAGCTGCGAGGAG

AAGAGCTGCGACAACCCCTACATCCCCAACGGCGACTACAGCCCCCTGCGCATCAAGCACCGCACCGGCGAC

GAGATCACCTACCAGTGCCGCAACGGCTTCTACCCCGCCACCCGCGGCAACACCGCCAAGTGCACCAGCACC

GGCTGGATCCCCGCCCCCCGCTGCACCCTGAAGCCCTGCGACTACCCCGACATCAAGCACGGCGGCCTGTAC

CACGAGAACATGCGCCGCCCCTACTTCCCCGTGGCCGTGGGCAAGTACTACAGCTACTACTGCGACGAGCAC

TTCGAGACCCCCAGCGGCAGCTACTGGGACCACATCCACTGCACCCAGGACGGCTGGAGCCCCGCCGTGCCC

TGCCTGCGCAAGTGCTACTTCCCCTACCTGGAGAACGGCTACAACCAGAACTACGGCCGCAAGTTCGTGCAG

GGCAAGAGCATCGACGTGGCCTGCCACCCCGGCTACGCCCTGCCCAAGGCCCAGACCACCGTGACCTGCATG

GAGAACGGCTGGAGCCCCCACCCCCCGCTGCATCCGCGTGAGCTTCACCCTGTAA

RC145: FHL-1 JCat - Manually optimised (SEQ ID NO: 34)
ATGCGCCTGCTCGCCAAGATCATTTGCCTGATGCTGTGGGCCATCTGCGTGGCCGAGGACTGCAACGAGCTG

CCCCCTCGCCGGAACACCGAGATCCTGACCGGCAGCTGGAGCGACCAGACCTACCCCGAGGGCACCCAGGCC

ATCTACAAGTGCCGCCCCGGCTACCGCAGCCTGGGCAACATCATTATGGTGTGCCGCAAGGGCGAGTGGGTG

GCCCTGAACCCCCTGCGCAAGTGCCAGAAGCGCCCCTGCGGCCACCCCGGCGACACCCCCTTCGGCACCTTC

ACCCTGACCGGCGGCAACGTGTTCGAGTACGGCGTGAAGGCCGTGTACACCTGCAACGAGGGCTACCAGCTG

CTCGGCGAGATCAACTACCGCGAGTGCGACACCGACGGCTGGACCAACGACATCCCCATCTGCGAGGTGGTC

AAGTGCCTGCCCGTGACCGCCCCCGAGAACGGCAAGATCGTGAGCTCCGCCATGGAGCCCGACCGCGAGTAC

CACTTCGGCCAGGCCGTGCGCTTCGTGTGCAACAGCGGCTACAAGATCGAGGGCGACGAGGAGATGCACTGC

AGCGACGATGGCTTCTGGAGCAAGGAGAAGCCCAAGTGCGTGGAGATCAGCTGCAAGAGCCCCGACGTGATC

AACGGCAGCCCCATCAGCCAGAAGATCATTTACAAGGAGAACGAGCGCTTCCAGTACAAGTGCAACATGGGC

TACGAGTACAGCGAGCGCGGCGACGCCGTGTGCACCGAGAGCGGCTGGCGCCCCCTGCCCAGCTGCGAGGAA

AAGAGCTGCGACAACCCCTACATCCCCAACGGCGACTACAGCCCCCTGCGCATCAAGCACCGCACCGGCGAC

GAGATCACCTACCAGTGCCGCAACGGCTTCTACCCCGCCACCCGCGGCAACACCGCCAAGTGCACCAGCACC

GGCTGGATCCCCGCCCCCCGCTGCACCCTGAAGCCCTGCGACTACCCCGACATCAAGCACGGCGGGCTGTAC

CACGAGAACATGCGCCGGCCCTACTTCCCCGTGGCCGTGGGCAAGTACTATAGCTACTATTGCGACGAGCAC

TTCGAGACCCCCAGCGGCAGCTACTGGGACCACATCCACTGCACCCAGGACGGCTGGAGCCCCGCCGTGCCC

TGCCTGCGCAAGTGCTACTTCCCCTACCTGGAGAACGGCTACAACCAGAACTACGGCCGCAAGTTCGTGCAG

-continued

```
GGCAAGAGCATCGACGTGGCCTGCCACCCCGGCTACGCCCTGCCCAAGGCCCAGACCACAGTGACCTGCATG

GAGAACGGCTGGAGCCCCACCCCCCGCTGCATCCGCGTGAGCTTCACCCTGTAA
```

RC146: FHL-1 COOL - Basic: see SEQ ID NO: 12, above.
RC147: FHL-1 COOL - Manually optimised:

(SEQ ID NO: 35)

```
ATGCGCCTCCTGGCCAAGATCATTTGCCTCATGCTGTGGGCCATCTGCGTGGCTGAGGACTGCAATGAGCTG

CCGCCCAGGAGAAACACAGAGATCCTGACAGGGAGCTGGTCTGACCAGACCTACCCTGAGGGCACCCAGGCG

ATCTACAAGTGCCGGCCGGGCTACAGGAGCCTGGGGAACATCATTATGGTGTGTAGAAAGGGCGAATGGGTG

GCCCTCAACCCCCTGAGGAAGTGCCAGAAGCGGCCCTGTGGCCACCCCGGGGACACACCCTTCGGGACCTTC

ACCCTGACCGGCGGGAATGTGTTTGAGTACGGCGTGAAGGCTGTCTACACATGCAACGAGGGGTACCAGCTG

CTCGGCGAGATTAACTACGGGAGTGTGACACCGATGGGTGGACCAACGACATTCCCATCTGTGAGGTGGTC

AAGTGTCTCCCCGTGACAGCCCCAGAAAATGGCAAAATTGTGAGCTCCGCCATGGAGCCTGACCGCGAATAT

CACTTTGGGCAGGCCGTGAGGTTTGTGTGCAACTCGGGCTACAAAATTGAAGGTGATGAGGAAATGCACTGC

AGCGATGACGGCTTCTGGTCCAAGGAGAAGCCCAAATGTGTGGAGATCTCCTGCAAGTCTCCCGACGTGATC

AACGGCAGCCCAATCAGCCAGAAGATTATCTACAAAGAGAACGAGCGCTTCCAGTACAAGTGTAACATGGGC

TATGAGTATTCAGAGAGGGGAGATGCCGTCTGCACTGAGAGCGGCTGGAGACCACTGCCTAGCTGCGAGGAA

AAGAGTTGTGACAACCCTTACATCCCAAATGGCGACTACTCCCCTCTGCGGATCAAACACCGGACCGGGGAT

GAAATCACCTATCAGTGCCGCAATGGATTCTACCCGGCCACCCGCGGCAACACCGCCAAATGCACCAGCACA

GGCTGGATCCCCGCCCCCCGCTGTACGCTGAAGCCTTGCGACTATCCAGACATCAAGCACGGAGGCCTGTAC

CACGAAAACATGCGGAGGCCTTATTTCCCTGTGGCAGTGGGGAAGTACTATAGCTACTATTGCGACGAGCAC

TTCGAGACCCCCTCTGGCTCCTACTGGGACCACATCCACTGCACACAGGACGGCTGGTCTCCAGCTGTGCCC

TGCCTGAGGAAATGCTACTTCCCCTACCTGGAGAACGGATACAACCAGAACTATGGCCGCAAGTTCGTGCAG

GGCAAGAGCATCGATGTGGCCTGCCACCCTGGCTACGCCCTGCCCAAGGCCCAGACAACTGTGACCTGCATG

GAGAATGGTTGGAGCCCCACCCCGCGCTGCATCCGGGTGTCCTTCACGCTCTGA
```

Generation of Plasmids

All 10 codon optimised sequences were synthesised and cloned by them into an AAV vector backbone. The vector also comprised AAV-2 left and right inverted terminal repeats (ITRs), which flank a modified CBA/CAG promoter (chicken beta-actin with CMV enhancer; "CBA"). The promoter drives expression of the codon optimised FHL1 or CFI. In addition, the transgene was followed downstream by a modified Woodchuck hepatitis virus post-transcriptional regulatory element (WPRE) sequence and a Bovine growth hormone poly-A (bGH polyA) sequence provided 3' to the cDNA.

Transfection

All 20 plasmids were transfected into ARPE19 cells using the following procedure:

Day 1: ARPE19 cells were dissociated and counted using a ViCell. Cells were seeded in a 48 well plate at $6 \times 10^4$ cells per well in 500 µL DMEM, 10% FBS per well.

Day 2: Confluency was checked and was found to be between 70-80%. Cells were then transfected with 0.25 µg plasmid DNA using PEI at a 1:3 DNA:PEI ratio in duplicate:

1. 2×0.25 µg DNA was diluted in 2×5 µL PBS.
2. 2× 0.75 UL PEI was diluted in 2×5 µL PBS.
3. PEI mix was added dropwise to DNA mix, mixed and then incubated at room temperature for 20 minutes.
4. 2×250 pl DMEM/Glutamax/10% FBS was added to the mixture.
5. Media was removed from the cells and replaced with 250 µL DNA/PEI complexes per well.

Day 3: Media was removed and replaced with 125 µL serum-free DMEM/Glutamax.

Day 5: Media was harvested, centrifuged at 14000 rpm for 10 minutes at 4° C. then supernatant was transferred to a fresh tube.

Western Blot

Supernatants from the transfection were analysed by Western blot (primary antibodies to CFI and FHL-1: goat antiserum CFI 1:3000; Quidel A312 1:3000; and secondary antibody rabbit anti-goat HRP 1:5000 were used).

Figure 2:
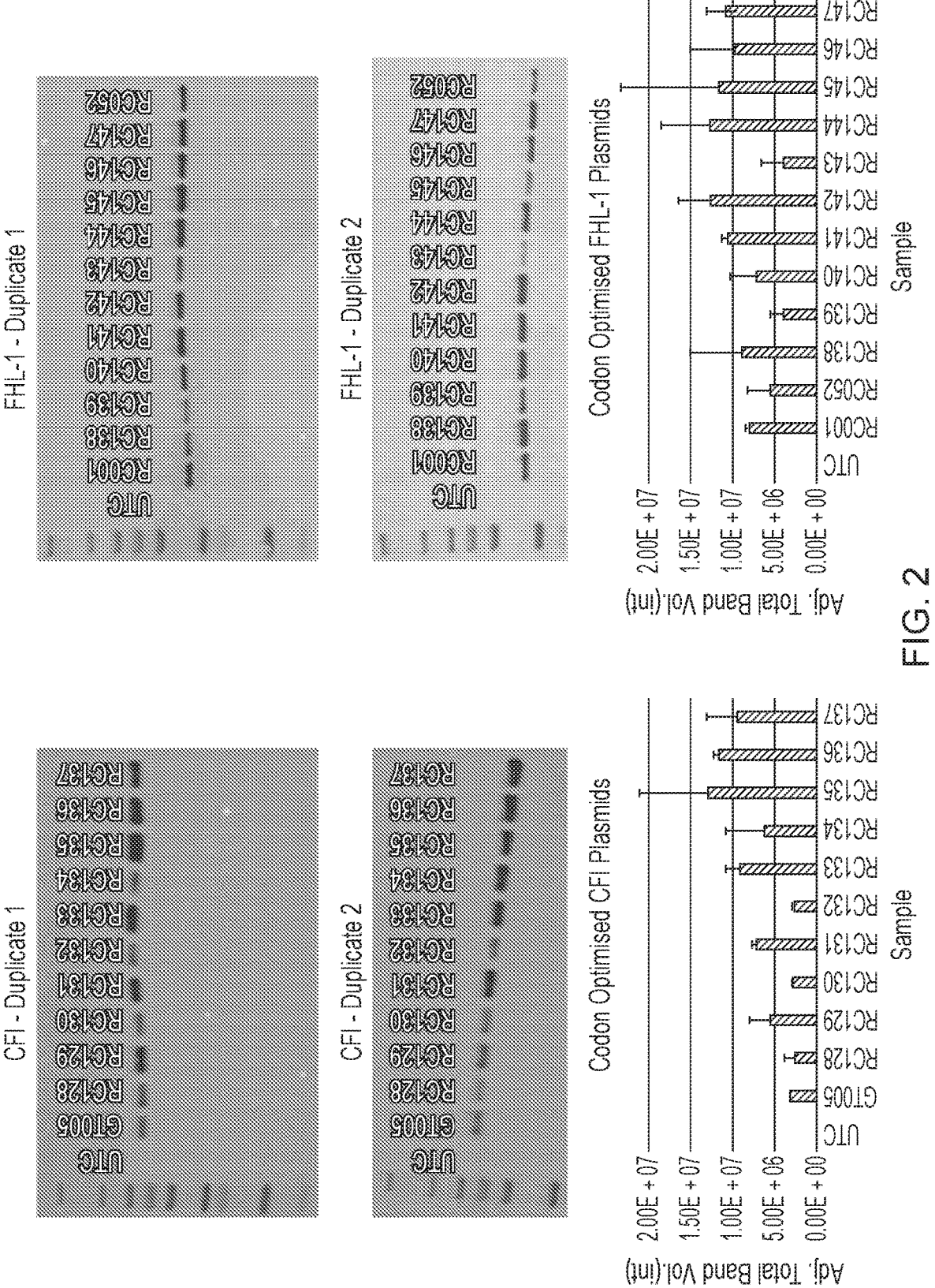

The Western blot analyses are shown in FIG. 2.

CFI ELISA

Supernatants from the transfection were analysed by ELISA for CFI using the following procedure:

Day 1: An ELISA plate was coated with 50 µL per well sheep anti-CFI polyclonal antibody diluted 1:4000 in 1× coating buffer. Plates stored at 4° C. overnight.

Day 2: The plate was washed 3 times with 200 µL per well PBS-Tween (0.05%) then blotted on a tissue. 200 µL 1% BSA fraction V in PBS-Tween (0.05%) was applied to each well and allowed to block for 2 hours at room temperature.

Samples and standard curve were prepared during the blocking incubation. A standard curve was made from purified CFI protein (Sigma C5938-1 MG) diluted into DMEM 2% FBS. Samples were diluted 1:10, 1:20 and 1:40 in DMEM 2% FBS.

After 2 hours blocking, the plate was washed 3 times, as described above, then 50 µL sample or standard was loaded onto each well and incubated at room temperature for 1 hour.

After 1 hour the plate was washed as above, then anti-CFI (Ox21) antibody was diluted 1:2000 in DMEM 5% FBS and 50 μL was applied to each well and incubated at room temperature for 1 hour.

After 1 hour, the plate was washed as above then donkey anti-mouse-HRP antibody was diluted 1:5000 in DMEM 5% FBS, and 50 μL was applied to each well and incubated at room temperature for 1 hour.

After 1 hour, the plate was washed as above, then 100 μL TMB reagent was applied to each well and incubated at room temperature in the dark for approximately 15 minutes. Once sufficient blue colour had been obtained, 100 μL 1 M sulphuric acid was added to each well to stop the reaction.

The A450 was then recorded with and data were processed and transferred to Microsoft Excel for analysis.

Figure 3:
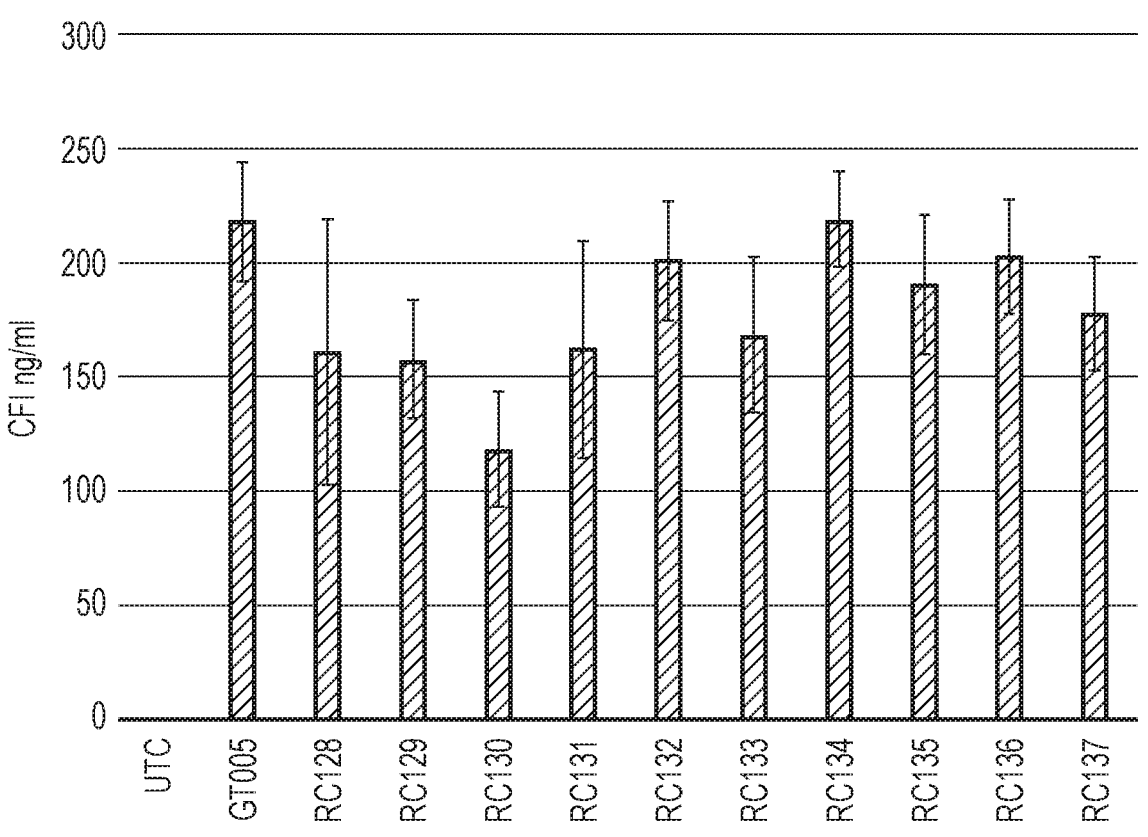

The CFI ELISA results are shown in FIG. 3.

FHL1 ELISA

Supernatants from the transfection were analysed by ELISA for FHL1 using the following procedure:

Day 1: An ELISA plate was coated with 50 μL per well anti-FHL-1 antibody (Biorad, AbD33594.1) diluted to 5 μg/mL in 100 mM Carbonate/Bicarbonate buffer, pH 9.6. Plates were stored at 4° C. overnight.

Day 2: The plate was washed 3 times with 200 μL per well PBS-Tween (0.05%) then blotted on a tissue. 200 μL 1% BSA fraction V in PBS-Tween (0.05%) was applied to each well and allowed to block for 2 hours at room temperature.

Samples and standard curve were prepared during the blocking incubation. A standard curve was made from FHL1-His protein diluted with DMEM+2% FBS. Samples were diluted 1:5, 1:10 and 1:30 in blocking solution.

After 2 hours blocking, the plate was washed 3 times, as described above then 50 μL sample or standard was loaded onto each well and incubated at room temperature for 1 hour.

After 1 hour, the plate was washed as above, then anti-CFH antibody (Ox24, Santa Cruz Biotechnologies, sc-53067) was diluted 1:3000 in DMEM 5% FBS and 50 μL was applied to each well and incubated at room temperature for 1 hour.

After 1 hour, the plate was washed as above then donkey anti-mouse-HRP antibody was diluted 1:5000 in DMEM 5% FBS and 50 μL was applied to each well and incubated at room temperature for 1 hour.

After 1 hour, the plate was washed as above, then 100 μL TMB reagent was applied to each well and incubated at room temperature in the dark for approximately 15 minutes. Once sufficient blue colour had been obtained, 100 μL 1 M sulphuric acid was added to each well to stop the reaction.

The A450 was then recorded with and data were processed and transferred to Microsoft Excel for analysis.

Figure 4:
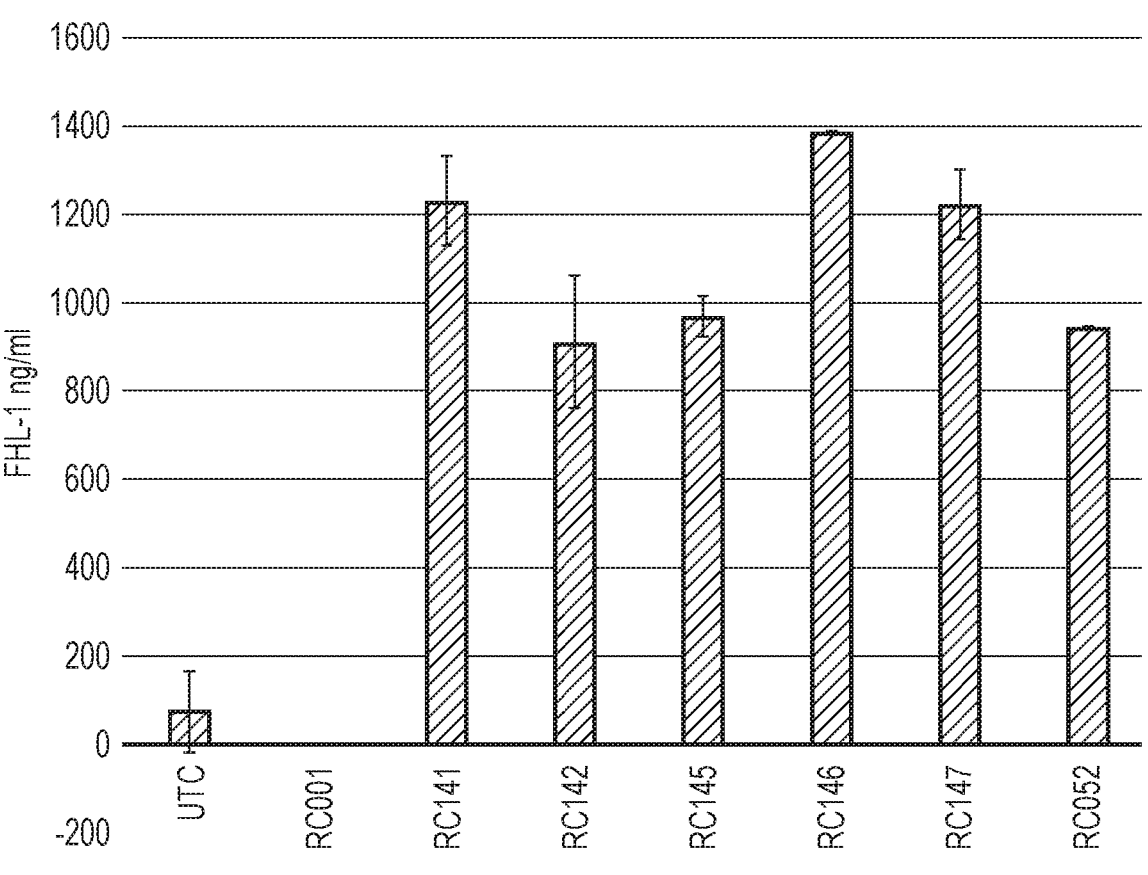

The FHL1 ELISA results are shown in FIG. 4.

Production of AAV2 Vectors

The best four (CFI) and five (FHL1) sequences were taken forward to studies using AAV.

HEK293 cells were transfected with the selected codon optimised plasmids along with pRepCap and pHelper as per a typical triple transfection protocol, specifically:

Day 1: HEK293 cells were dissociated and counted using a ViCell. Cells were seeded in a 10 cm dish at 6×10⁵ cells per cm² in 10 mL DMEM 10% FBS per dish.

Day 2: Confluency was checked and was found to be between 70-80%.

Media was replaced with 10 mL DMEM/Glutamax with 5% FBS.

After 4 hours the cells were transfected with 5 μg plasmid using PEI at a 1:3 DNA:PEI ratio.

Day 3:15 mM butyrate was added to the 11 mL media in each plate.

Day 5: Supernatant was harvested and centrifuged at 1000 rpm for 10 minutes to remove cell debris.

The supernatant was transferred to a fresh tube and 1/5 vol. AAVanced (AAV110A-1, Cambridge Bioscience) reagent was added (2.75 mL in 11 mL).

The mixture was then stored at 4° C.

Day 8: The supernatant/AAVanced mixture was centrifuged at 1000 rpm for 30 minutes at 4° C.

The supernatant was discarded and the pellet resuspended in 500 μL PBS. This was then transferred to a 1.5 mL tube and centrifuged for 3 minutes at 1500 g.

The supernatant was discarded and the remaining pellet resuspended in 1/100 original volume (i.e. 100 μL per 11 mL supernatant).

The vector was stored at −80° C.

Transduction of ARPE19 Cells

ARPE19 cells were transduced with the vectors comprising the codon optimised transgenes.

Day 1: ARPE19 cells were dissociated and counted a ViCell then seeded at 1×10⁵ cells per well in 200 μL DMEM/Glutamax+10% FBS.

Day 2: Vector was added to the cells.

Day 3: Media was replaced with serum-free media.

Day 4: The supernatant was harvested, centrifuged at 14000 rpm for 10 minutes at 4° C., then transferred to a fresh tube.

Total protein concentration was assessed by Bradford Assay.

CFI ELISA

Supernatants from the transduction were analysed by ELISA for CFI according to the protocol above.

Figure 5:
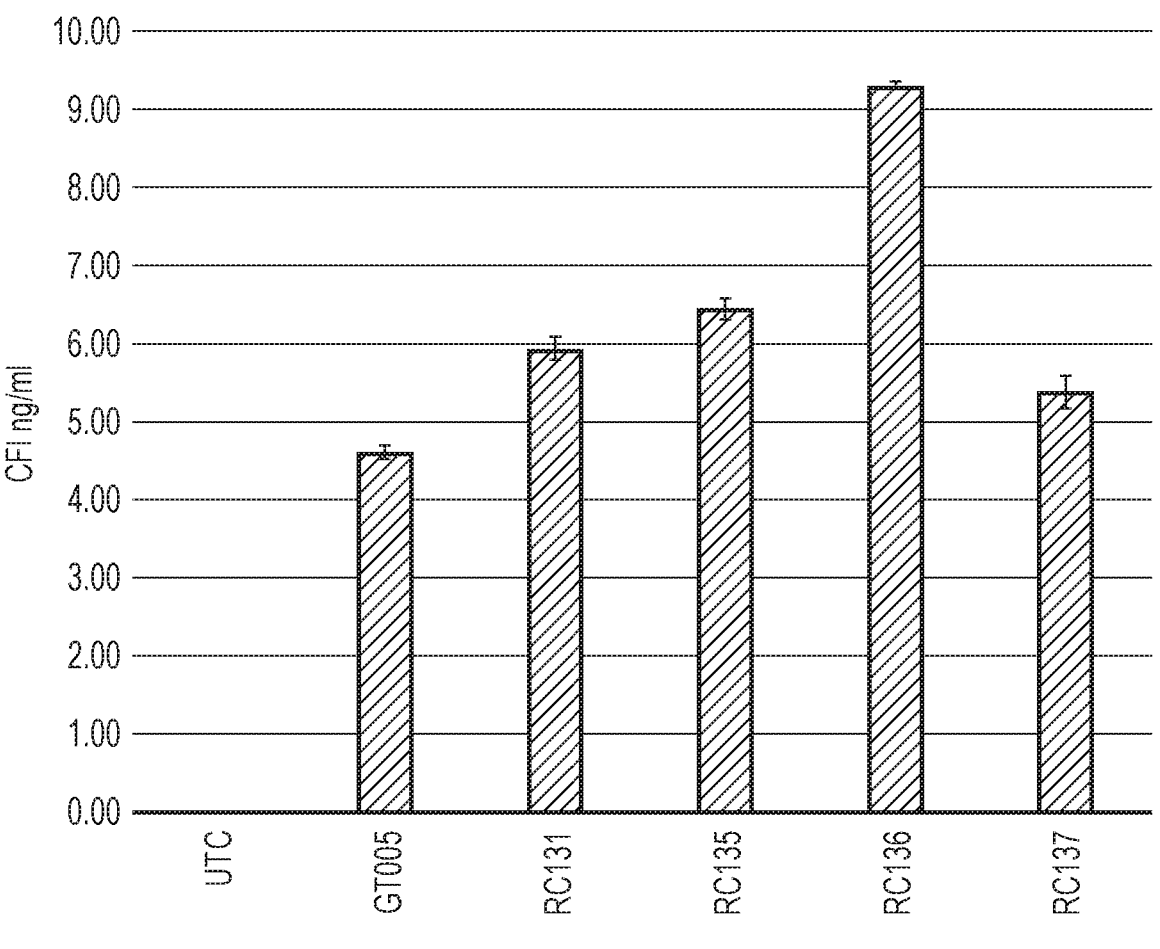

The CFI ELISA results are shown in FIG. 5.

FHL-1 ELISA

Supernatants from the transduction were analysed by ELISA for FHL1 according to the protocol above.

Figure 6:
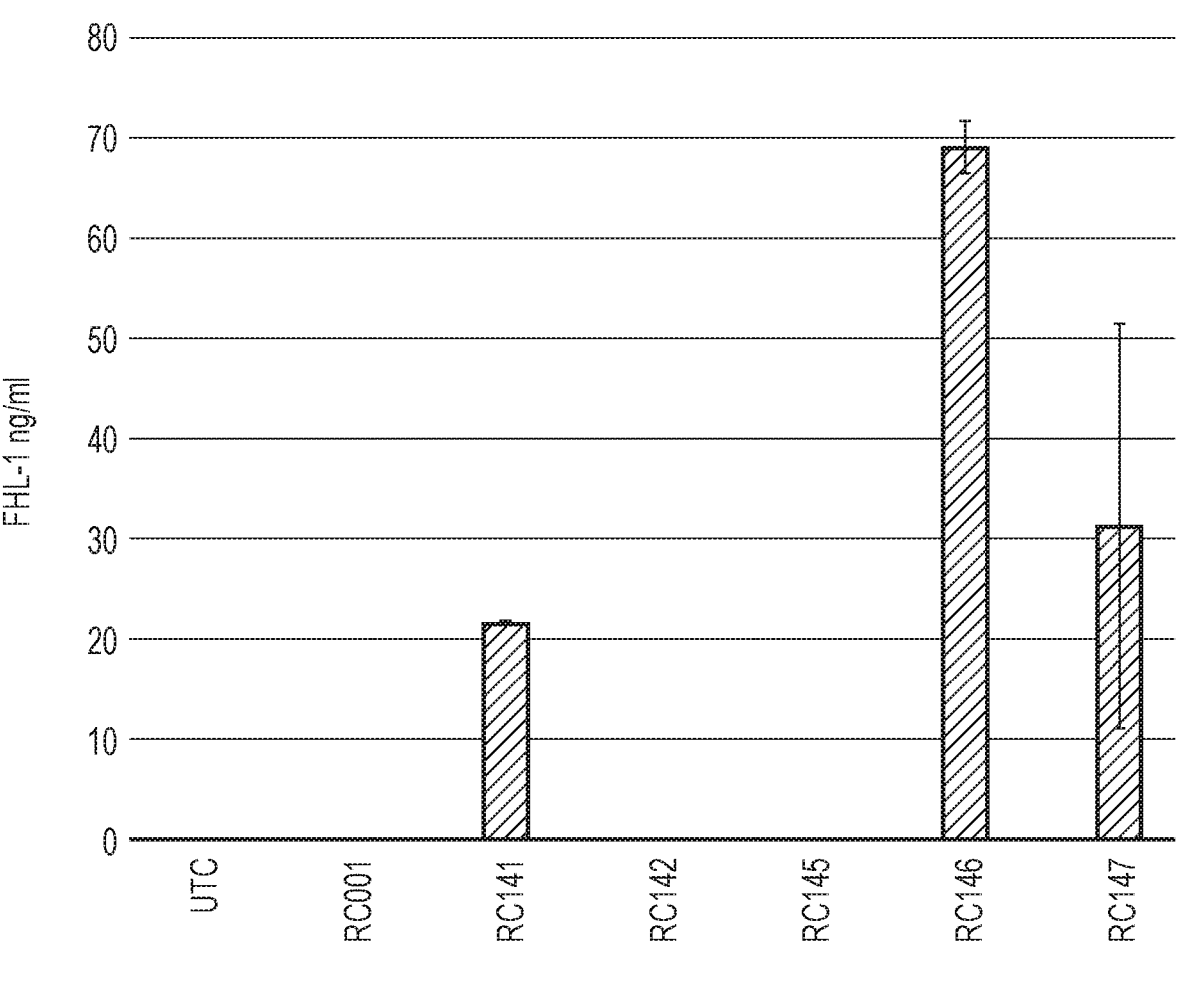

The FHL1 ELISA results are shown in FIG. 6.

CONCLUSIONS

RC136 (CFI; SEQ ID NO: 10) and RC146 (FHL-1; SEQ ID NO: 12) each give higher expression of the transgene than the wild type sequences and other codon-optimised sequences tested.

All publications mentioned in the above specification are herein incorporated by reference. Various modifications and variations of the disclosed agents, compositions, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. An AAV vector particle comprising AAV2 capsid proteins and a polynucleotide comprising a nucleotide sequence encoding Complement Factor H-like Protein 1 (FHL1) and having at least 95% sequence identity to SEQ ID NO: 12 over the entire length of SEQ ID NO:12.

2. The AAV vector particle of claim 1, wherein the nucleotide sequence encoding FHL1 comprises the nucleotide sequence set forth in SEQ ID NO: 12.

3. The AAV vector particle of claim 1, wherein the nucleotide sequence encoding FHL1 is operably linked to a CMV promoter; a WPRE regulatory element; and/or a poly-A signal.

4. An ex vivo cell transduced with the AAV vector particle of claim 1.

5. A pharmaceutical composition comprising the AAV vector particle of claim 1 in combination with a pharmaceutically acceptable carrier, diluent or excipient.

6. The AAV vector particle of claim 3, wherein the nucleotide sequence encoding FHL1 has at least 98% sequence identity to SEQ ID NO: 12 over the entire length of SEQ ID NO: 12.

* * * * *